US010443081B2

(12) United States Patent
Schmitt et al.

(10) Patent No.: US 10,443,081 B2
(45) Date of Patent: *Oct. 15, 2019

(54) METHODS FOR THE EXPRESSION OF PEPTIDES AND PROTEINS

(71) Applicant: Numaferm GmbH, Duesseldorf (DE)

(72) Inventors: Lutz Schmitt, Neuss (DE); Christian Schwarz, Duesseldorf (DE); Sander Hendrikus Joannes Smits, Duesseldorf (DE)

(73) Assignee: Numaferm GmbH, Duesseldorf (DE)

( * ) Notice: Subject to any disclaimer, the term of this patent is extended or adjusted under 35 U.S.C. 154(b) by 339 days.

This patent is subject to a terminal disclaimer.

(21) Appl. No.: 14/785,216

(22) PCT Filed: Apr. 17, 2014

(86) PCT No.: PCT/EP2014/057887

§ 371 (c)(1),
(2) Date: Oct. 16, 2015

(87) PCT Pub. No.: WO2014/170430

PCT Pub. Date: Oct. 23, 2014

(65) Prior Publication Data

US 2016/0138066 A1 May 19, 2016

(30) Foreign Application Priority Data

Apr. 17, 2013 (EP) .................................... 13164098

(51) Int. Cl.

| | |
|---|---|
| ***C12P 21/02*** | (2006.01) |
| ***C07K 14/00*** | (2006.01) |
| ***C07K 14/195*** | (2006.01) |
| ***C07K 14/245*** | (2006.01) |
| ***C07K 14/475*** | (2006.01) |
| ***C07K 14/56*** | (2006.01) |
| ***C07K 14/575*** | (2006.01) |
| ***C12N 9/10*** | (2006.01) |
| ***C12N 9/88*** | (2006.01) |
| ***C07K 14/47*** | (2006.01) |

(52) U.S. Cl.

CPC .............. *C12P 21/02* (2013.01); *C07K 14/00* (2013.01); *C07K 14/195* (2013.01); *C07K 14/245* (2013.01); *C07K 14/47* (2013.01); *C07K 14/475* (2013.01); *C07K 14/4711* (2013.01); *C07K 14/4713* (2013.01); *C07K 14/56* (2013.01); *C07K 14/57509* (2013.01); *C12N 9/13* (2013.01); *C12N 9/88* (2013.01); *C07K 2319/00* (2013.01); *C07K 2319/036* (2013.01); *C07K 2319/35* (2013.01); *C12Y 208/01008* (2013.01); *C12Y 406/01001* (2013.01)

(58) Field of Classification Search

None

See application file for complete search history.

(56) References Cited

FOREIGN PATENT DOCUMENTS

| | | | |
|---|---|---|---|
| CN | 101595219 | A | 12/2009 |
| CN | 101792729 | A | 8/2010 |
| EP | 2583975 | A1 | 4/2013 |

OTHER PUBLICATIONS

Linhartová, I., et al. 2010 FEMS Microbiol Rev 34: 1076-1112 (Year: 2010).*

Umelo-Njaka et al., "Expression and testing of *Pseudomonas aeruginosa* vaccine candidate proteins prepared with the *Caulobacter crescentus* S-layer protein expression system," *Vaccine* 19:1406-1415, 2001.

Schwarz et al., "Secretion of slow-folding proteins by a Type 1 secretion system," *Bioengineered* 3(5):289-292, 2012.

Singh et al., "Solubilization and Refolding of Bacterial Inclusion Body Proteins," *Journal of Bioscience and Bioengineering* 99(4):303-310, 2005.

Abts et al., "Easy and Rapid Purification of Highly Active Nisin," *International Journal of Peptides* 2011, 9 pages, 2011.

Bakkes et al., "The Rate of Folding Dictates Substrate Secretion by the *Escherichia coli* Hemolysin Type 1 Secretion System," *J Biol Chem* 285(52):40573-40580, 2010.

Database UniProt: accessed from EBI Accession No. UNIPROT:H4XVI8, 2 pages, 2012.

Kanonenberg et al., "Type I secretion systems—a story of appendices," *Research in Microbiology* 164:596-604, 2013.

Lecher et al., "An RTX Transporter Tethers Its Unfolded Substrate during Secretion via a Unique N-Terminal Domain," *Structure* 20:1778-1787, 2012.

Park et al., "Identification of the minimal region in lipase ABC transporter recognition domain of *Pseudomonas fluorescens* for secretion and fluorescence of green fluorescent protein," Microbial *Cell Factories* 11:60, 12 pages, 2012.

Schwarz et al., "Using an *E. coli* Type 1 secretion system to secrete the mammalian, intracellular protein IFABP in its active form," *Journal of Biotechnology* 159:155-161, 2012.

Thomas et al., "The Type 1 secretion pathway—The hemolysin system and beyond," *Biochimica et Biophysical Acta—Molecular Cell Research*, 11 pages, 2013.

* cited by examiner

*Primary Examiner* — Marsha Tsay

(74) *Attorney, Agent, or Firm* — Seed IP Law Group LLP

(57) ABSTRACT

The present invention lies in the field of molecular biology, recombinant peptide and protein expression and relates to methods comprising nucleic acid sequences comprising allocrites of T1SSs or fragments thereof for the efficient production of recombinant Pe OIs and Pr OI. The allocrites or fragments thereof improve the expression of PeOI and Pr OI as IB and function as IB-tags.

14 Claims, 16 Drawing Sheets

Specification includes a Sequence Listing.

A

B

C

METHODS FOR THE EXPRESSION OF PEPTIDES AND PROTEINS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 440097_402USPC_SEQUENCE_LISTING.txt. The text file is 80.2 KB was created on Jan. 26, 2016, and is being submitted electronically via EFS-Web.

FIELD OF THE INVENTION

The present invention lies in the field of molecular biology, recombinant peptide and protein expression and relates to methods comprising nucleic acid sequences of substrates/allocrites of Type 1 secretion systems or fragments thereof for the efficient production of recombinant peptides and proteins of interest. The allocrites or fragments thereof improve the expression of peptides and protein of interest as inclusion bodies (IB) and function as IB-tags.

BACKGROUND OF THE INVENTION

In recent years recombinant protein/enzyme production for use in industrial processes has become more and more important and it is expected that soon many industrial processes will involve recombinant technologies. Currently, bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper industries, textiles, food industries, personal care and cosmetics industries, sugar refining, wastewater treatment, production of alcoholic beverages and as catalysts for the generation of new pharmaceuticals.

However, the expression of recombinant peptides and proteins is still limited, as large efforts are required in order to obtain the desired peptides and proteins with a native fold, in high amounts and high purity.

Generally, product purification is expensive and especially the final step to 100% purity tends to increase the costs exponentially because proteins with similar characteristics are difficult to separate from one another (Hacking, A. J. (1986) Economic aspects of biotechnology, Cambridge University Press).

In many cases it is useful to express a protein or peptide in insoluble form, particularly when the peptide of interest (PeOI) or protein of interest (PrOI) is rather short, normally soluble, and/or subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion peptide/protein by including in the fusion peptide at least one solubility tag (i.e., an inclusion body (IB) tag) that induces IB formation. Typically, the fusion protein is designed to include at least one cleavable peptide linker so that the PeOI or PrOI can be subsequently recovered from the fusion protein. The fusion protein may be designed to include a plurality of IB-tags, cleavable peptide linkers, and regions encoding the PeOI or PrOI.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptides typically used include, but are not limited to chloramphenicol acetyltransferase (Dykes et al., (1988) Eur. J. Biochem., 174:411), β-galactosidase (Schellenberger et al., (1993) Int. J. Peptide Protein Res., 41:326; Shen et al., (1984) Proc. Nat. Acad. Sci. USA 281:4627; and Kempe et al., (1985) Gene, 39:239), glutathione-S-transferase (Ray et al., (1993) Bio/Technology, 11:64 and Hancock et al. (WO94/04688)), the N-terminus of L-ribulokinase (U.S. Pat. No. 5,206,154 and Lai et al., (1993) Antimicrob. Agents & Chemo.), 37:1614, bacteriophage T4 gp55 protein (Gramm et al., (1994) Bio/Technology, 12:1017), bacterial ketosteroid isomerase protein (Kuliopulos et al., (1994) J Am. Chem. Soc. 116:4599 and in U.S. Pat. No. 5,648,244), ubiquitin (Pilon et al., (1997) Biotechnol. Prog., 13:374-79), bovine prochymosin (Haught et al., (1998) Biotechnol. Bioengineer. 57:55-61), and bactericidal/permeability-increasing protein ("BP1"; Better, M. D. and Gavit, P D., U.S. Pat. No. 6,242,219). The art is replete with specific examples of this technology, see for example U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. Nos. 5,215,896; 5,302,526; 5,330,902; and U.S. Patent Application Publication No. 2005/221444, describing fusion tags containing amino acid compositions specifically designed to increase insolubility of the chimeric protein or peptide.

However, the methods known in the art do not provide any solution to refold the PeOI or PrOI. Thus, there is still need in the art for methods that allow improved production of a recombinant PeOI and PrOI.

The present inventors found that methods comprising nucleic acid sequences comprising hemolysin A (HlyA) or lipase A (LipA) gene fragments overcome the above need in the art. Both genes are part of a Type 1 secretion system (TISS), which mostly occur in Gram-negative bacteria and export their cognate substrates in a single step from the cytosol to the extracellular medium without the formation of periplasmic substrate intermediates. Among the family of TISS the Hly TISS described by Bakkes et al. involving HlyA as transport substrate is of particular interest, as it carries so-called GG repeats with the consensus sequence GGxGxDxUx (SEQ ID NO: 67(x: any amino acid residue, U: large, hydrophobic amino acid residue) (Ostolaza, H. et al., (1995) Eur J Biochem 228, 39-44). These GG repeats bind $Ca^{2+}$ ions with high affinity. This binding event happens after the secretion of the TISS allocrite to the exterior, where the $Ca^{2+}$ concentration is high (up to the mM range) compared to the $Ca^{2+}$ concentration inside the cells (high nM). $Ca^{2+}$ binding to the GG repeats catalyzes the folding of the allocrites into the native, active conformation and $Ca^{2+}$ ions act as a folding helper/chaperone (Jumpertz, T. et al., Microbiology 156, 2495-2505, doi:mic.0.038562-0 [pii]). Further components of the HlyA TISS of *E.coli* are the inner membrane protein HlyB, which is an ATP binding cassette (ABC) transporter, the outer membrane protein (OMP) TolC and the membrane fusion protein (MFP) HlYD in the inner membrane.

SUMMARY OF THE INVENTION

In a first aspect, the present invention relates to a method for production of a recombinant PeOI or PrOI, wherein the method comprises (a) introducing a nucleic acid molecule encoding a fusion protein comprising at least one PeOI or PrOI, and at least one allocrite of a T1SS or a fragment thereof, into a host cell, wherein the host cell does not express a heterologous ABC transporter, a heterologous MFP and/or a heterologous OMP of the T1SS; (b) cultivating the host cell under conditions that allow expression of the fusion protein, wherein the fusion protein is expressed in the form of IB; (c) isolating the recombinant fusion protein from said host cells; and (d) subjecting the recombinant fusion protein to conditions that allow the PeOI or PrOI to fold into a functional three-dimensional conformation.

In various embodiments, the allocrit of a T1SS is selected from the group consisting of of HlyA, CyaA, EhxA, LktA, PlLktA, PasA, PvxA, MmxA, LtxA, ApxIA, ApxIIA, ApxIIIA, ApxIVA, ApxI, ApxII, AqxA, VcRtxA, VvRtxA, MbxA, RTX cytotoxin, RtxL1, RtxL2, FrhA, LipA, TliA, PrtA, PrtSM, PrtG, PrtB, PrtC, AprA, AprX, ZapA, ZapE, Sap, HasA, colicin V, LapA, ORF, RzcA, RtxA, XF2407, XF2759, RzcA, RsaA, Crs, CsxA, CsxB, SlaA, SwmA, Sll1951, NodO, PlyA, PlyB, FrpA, FrpC and fragments thereof.

In preferred embodiments, the allocrit of a T1SS may be HlyA comprising or consisting of the amino acid sequence as set forth in SEQ ID NO:2, a fragment thereof or a polypeptide that has at least 80% sequence identity to the amino acid sequence of SEQ ID NO:2 or the fragment thereof.

In more preferred embodiments, the fragment of HlyA consists of the amino acid sequence as set forth in SEQ ID NO:4 or a polypeptide that has at least 80% sequence identity to the amino acid sequence of SEQ ID NO:4.

In various embodiments, the expression medium comprises 20.0 mM or less of $Ca^{2+}$.

In further embodiments, the present invention relates to a method wherein the expression of the endogenous ABC transporter gene, the endogenous MFP gene and/or the endogenous OMP gene of the T1SS or the activity of the corresponding gene products in the host cell is inhibited or the transport is inefficient.

In other various embodiments, the host cell does not express endogenous ABC transporter, endogenous MFP and/or endogenous OMP of the T1SS.

In still further embodiments, the recombinant peptide or protein may be exposed to a refolding buffer, wherein the refolding buffer comprises at least 0.01 mM of $Ca^{2+}$.

In various embodiments of the methods of the invention, (I) the host cell is a prokaryotic cell; and/or (II) the expression is performed in minimal culture medium; and/or (III) the recombinant fusion peptide or protein is purified using a method selected from affinity chromatography, ion exchange chromatography, reverse phase chromatography, size exclusion chromatography, and combinations thereof; and/or (IV) the method comprises the additional step (e) contacting of the recombinant fusion protein with a protease suitable for cleavage of the fusion protein to yield the allocrite and the PeOI or PrOI as separate molecules; and/or (V) the method comprises a step (e) as defined in (IV) followed by purification of the PeOI or PrOI.

In still other embodiments, the present invention may also relate to a method wherein the at least one PeOI or PrOI is selected from the group consisting of Nisin, HCRF, IFABP, IFNA2, MBP, peptide 101, peptide 102, peptide 103, MAB-40 Mab-42, Fuzeon®, salmon Calcitonin, human Calcitonin, peptides 1, 238, 239, 240 or 241.

Moreover, the nucleic acid molecule encoding the fusion protein further comprises a regulatory nucleotide sequence that modulates expression of the fusion protein in further embodiments.

It is understood that all combinations of the above disclosed embodiments are also intended to fall within the scope of the present invention.

BRIEF DESCRIPTION OF THE DRAWINGS

FIG. 2B shows cell lysate samples of *E. coli* expressing fusion proteins of HlyA1 and indicated PrOI or PeOI, wherein the PrOI or PeOI are C-terminally fused to HlyA1, analyzed by SDS-PAGE and visualized by CBB staining. FIG. 2C depicts a SDS-PAGE (15%) of soluble and insoluble fractions after cell disruption of cells producing IFABP wt (encoded by plasmid pQE-IFABP wt) or HlyA1-IFABP wt (encoded by pIAR_207). A soluble degradation product of HlyA1-IFABP wt is indicated. FIG. 2D shows the expression of peptides 238, 239, 240 and 241 fused to HlyA1 and demonstrates that the expression of peptides 240 and 241 fails without the fusion protein HlyA1.

Nisin refolded with $Ca^{2+}$. C and D: LipA1-Nisin was refolded in the presence of EDTA and analyzed as described in A and B.

Figure 6:
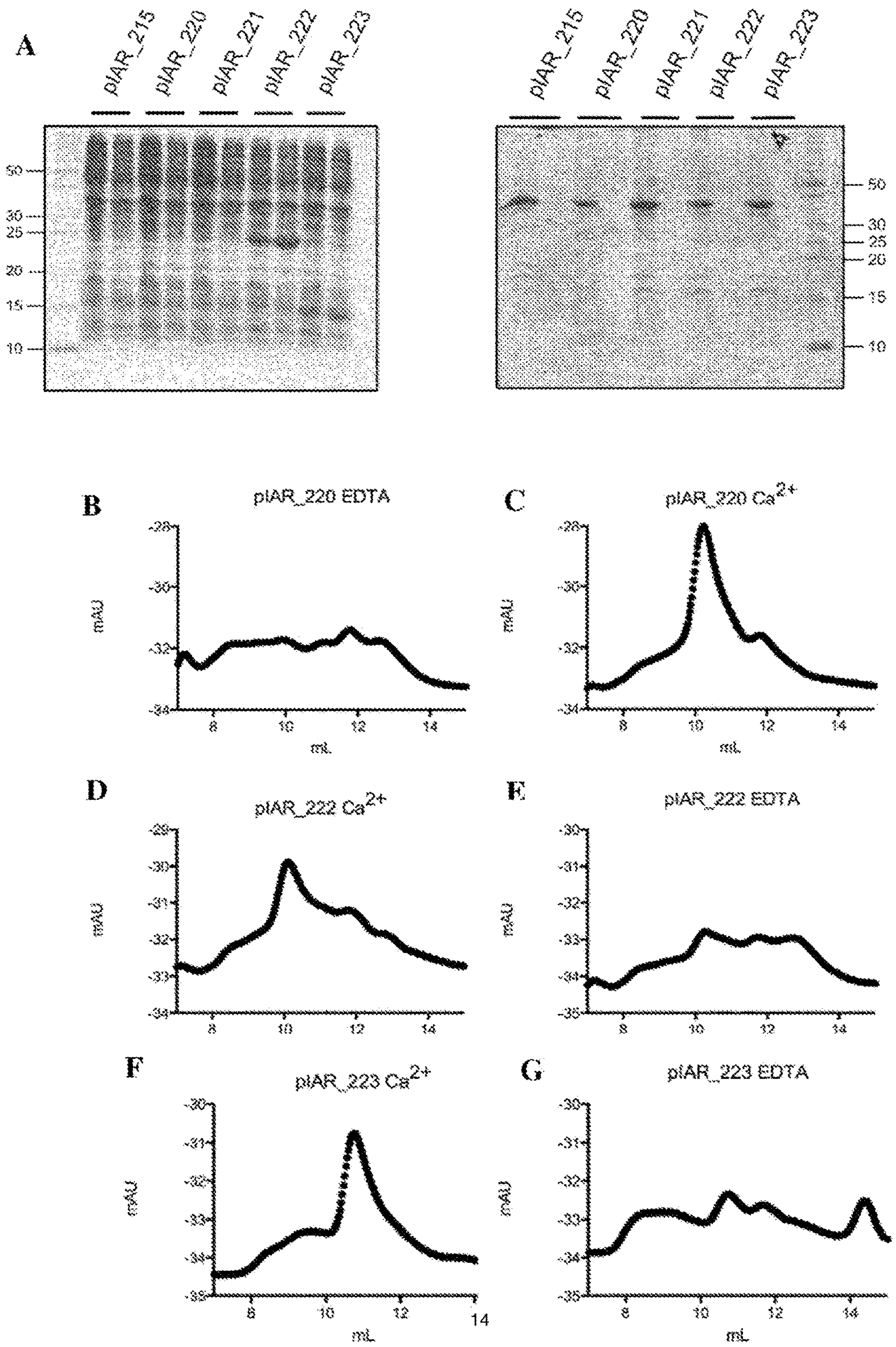

FIG. 6 shows expression analyses of peptides encoded by pIAR_215, pIAR_220, pIAR_221, pIAR_222 and pIAR_223 and refolding experiments of expressed peptides (encoded by pIAR_220, pIAR_222 and pIAR_223) in the presence of $Ca^{2+}$ and EDTA. The indicated proteins were produced as IBs in *E. coli* and isolated IBs were refolded in the presence of $Ca^{2+}$ or EDTA. A: SDS-PAGE analysis of indicated samples. B-G: SEC analysis of refolded indicated proteins.

Figure 7:
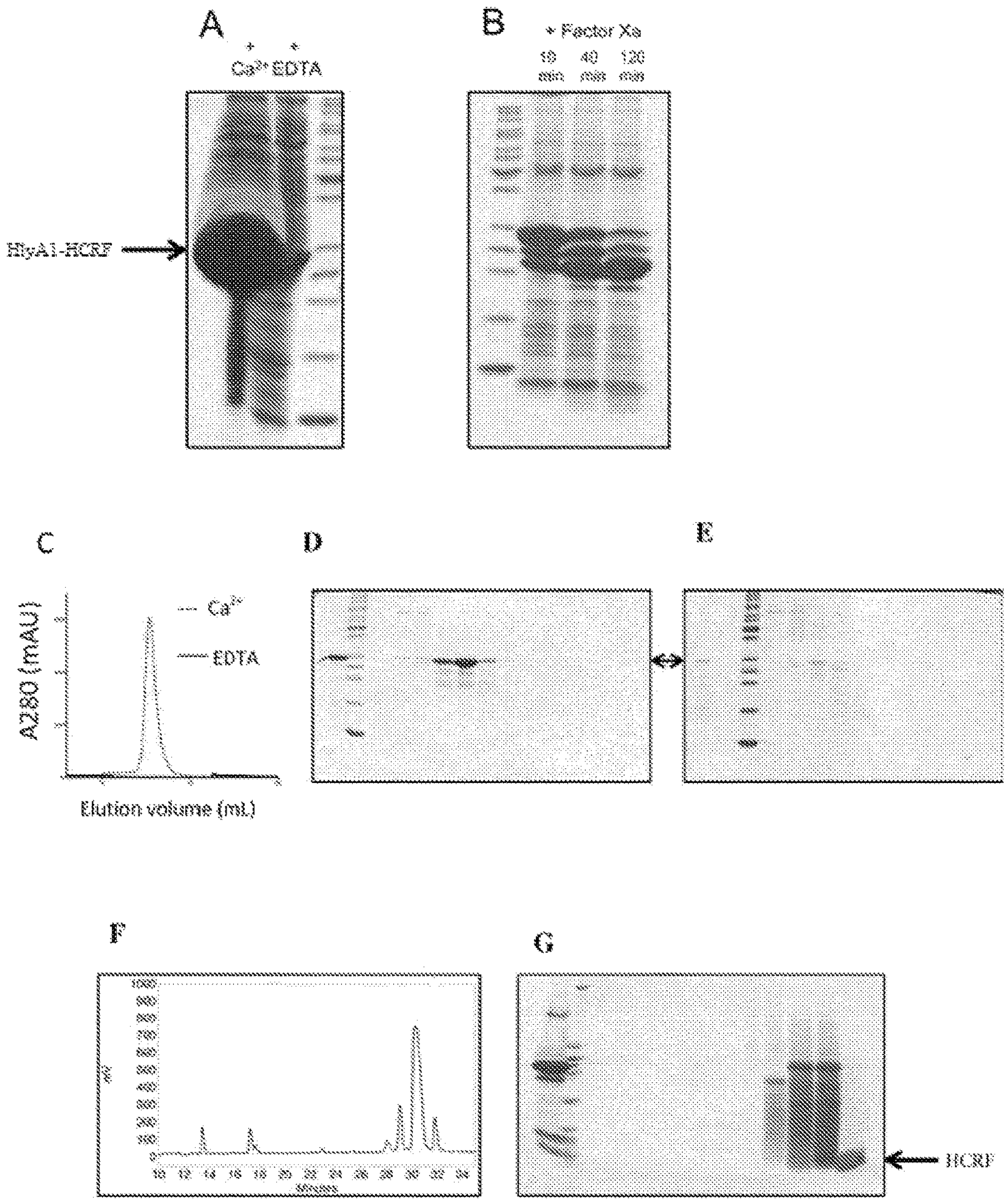

FIG. 7 shows the production of HCRF. A: IBs of HlyA1-HCRF, encoded by plasmid pIAR_202, were refolded either in the presence of $Ca^{2+}$ or EDTA. B: HlyA1-HCRF, refolded in the presence of $Ca^{2+}$, was incubated with Factor Xa for 10 min, 40 min and 120 min. HlyA1-HCRF, refolded in buffer containing either $Ca^{2+}$ or EDTA, was applied to SEC analysis and elution fractions were analyzed by SDS-PAGE. C: Elution chromatograms of the above mentioned SEC analysis. D: CBB stained SDS-PAGE gel after SEC analysis of HlyA1-HCRF refolded in the presence $Ca^{2+}$. E: CBB stained SDS-PAGE gel after SEC analysis of HlyA1-HCRF refolded in the presence of EDTA. HlyA1-HCRF was refolded in the presence of $Ca^{2+}$, incubated with Factor Xa for 2 h and the digestion mixture was purified by HPLC. F: HPLC chromatogram. G: CBB stained SDS-PAGE gel of HPLC elution fractions.

Figure 8:
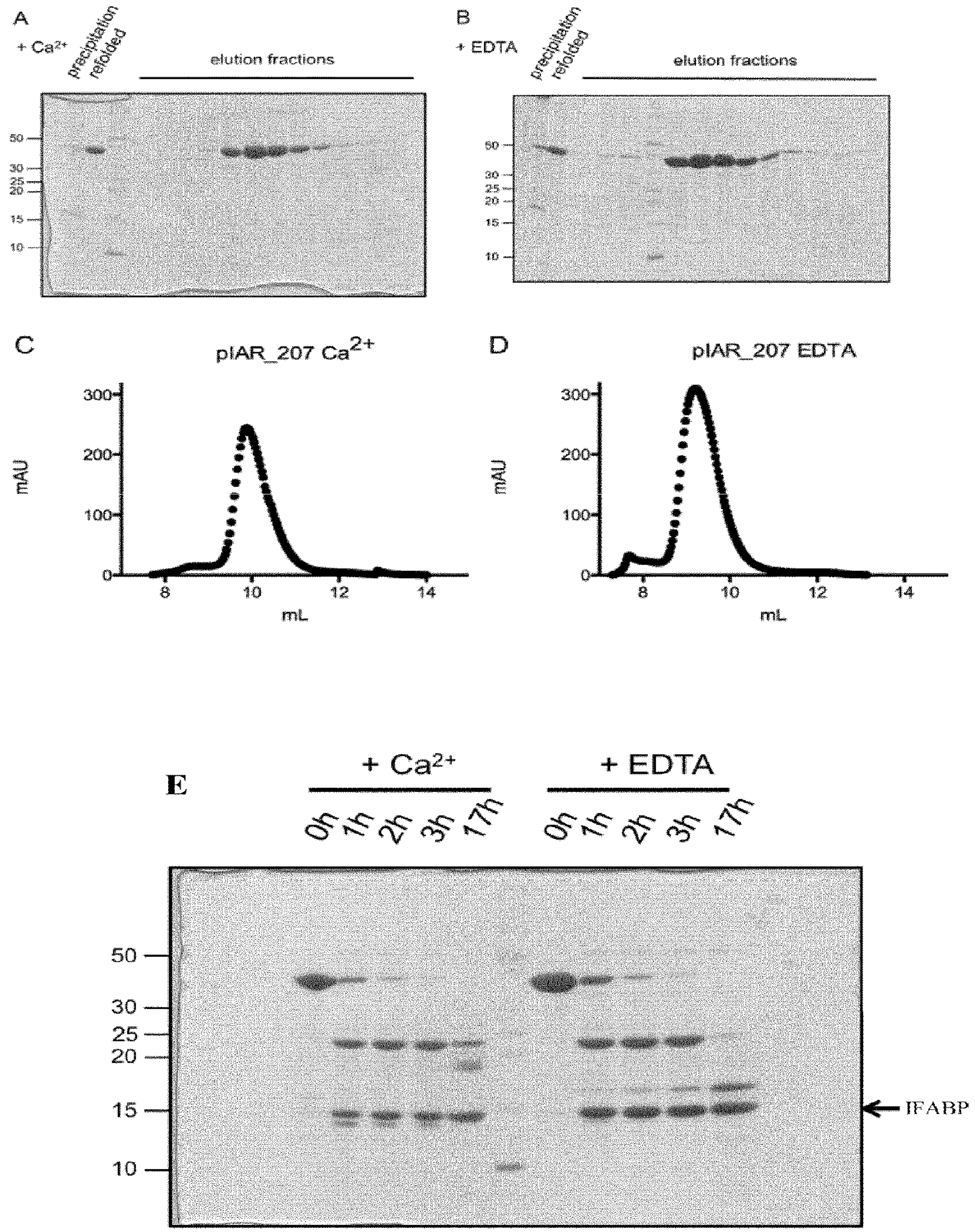
Figure 8:
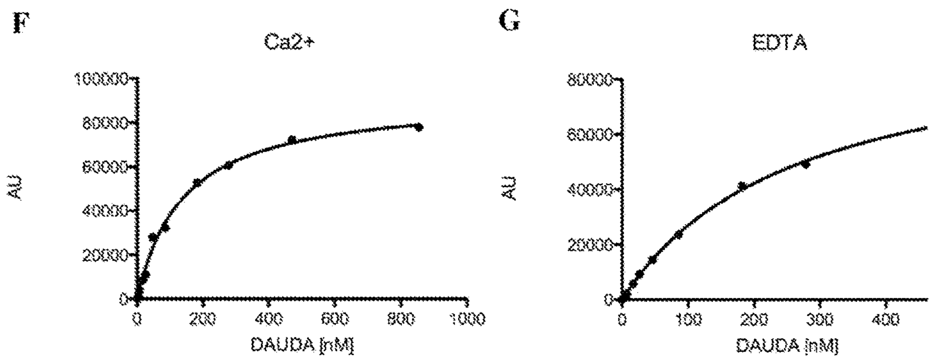

FIG. 8 shows the production and functional studies of HlyA1-IFABP. SEC analyses of refolded HlyA1-IFABP. A and C: SDS-PAGE gel of elution fractions from SEC analysis of HlyA1-IFABP refolded with $Ca^{2+}$ and elution chromatogram of the SEC. B and D: SDS-PAGE gel of elution fractions from SEC analysis of HlyA1-IFABP refolded with EDTA and elution chromatogram of the SEC. E: Purified HlyA1-IFABP in the presence of either $Ca^{2+}$ or EDTA were incubated with Factor Xa and protein samples were analyzed by SDS-PAGE at indicated time points. The arrow indicates the position of IFABP. F and G: Functional studies of HlyA1-IFABP using titration experiments with DAUDA. F: HlyA1-IFABP was refolded in the presence of $Ca^{2+}$ and purified by SEC. DAUDA was titrated to HlyA1-IFABP, the fluorescence signal at 500 nm was recorded and plotted against the DAUDA concentration. The black lane represents the curve of the theoretical fit. G: Same experiments as in F were repeated with HlyA1-IFABP purified in the presence of EDTA.

Figure 9:
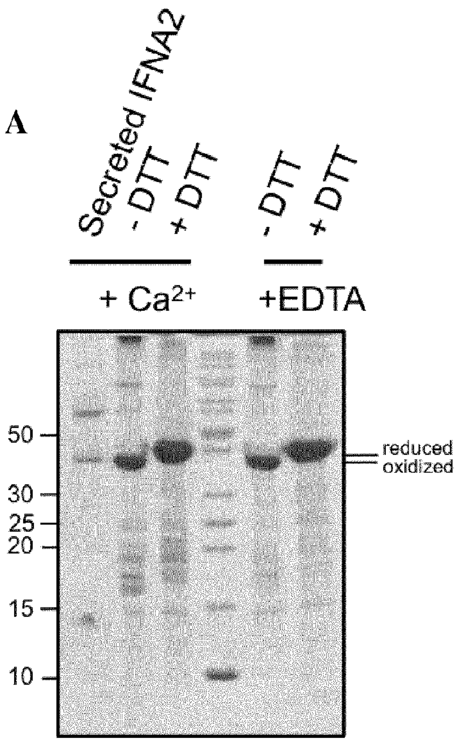
Figure 9:
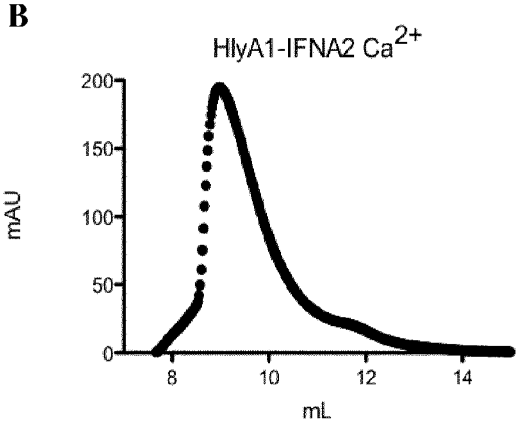
Figure 9:
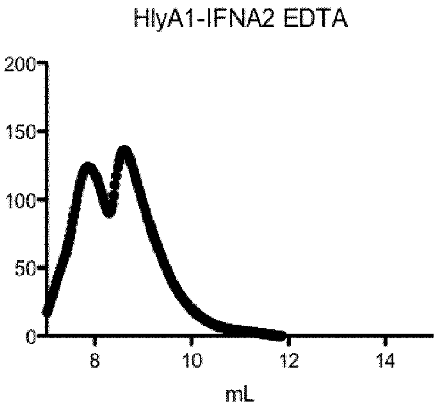

FIG. 9 shows the production of HlyA1-IFNA2. A: SDS-PAGE analyses of HlyA1-IFNA2 refolded in the presence of 0.5 M arginine. Secreted IFNA2-HlyA1 served as reference for oxidized protein containing disulfide bonds (left lane). In the absence of DTT, HlyA1-IFNA2 migrates on the same running height as the reference. In contrast, HlyA1-IFNA2 in the presence of DTT migrates slower. These results indicate the formation of disulfide bonds within refolded HlyA1-IFNA2. B and C: SEC analyses of HlyA1-IFNA2 after refolding in the presence of $Ca^{2+}$ and EDTA, respectively. B: Refolding in the presence of $Ca^{2+}$. C: Refolding in the presence of EDTA.

Figure 10:
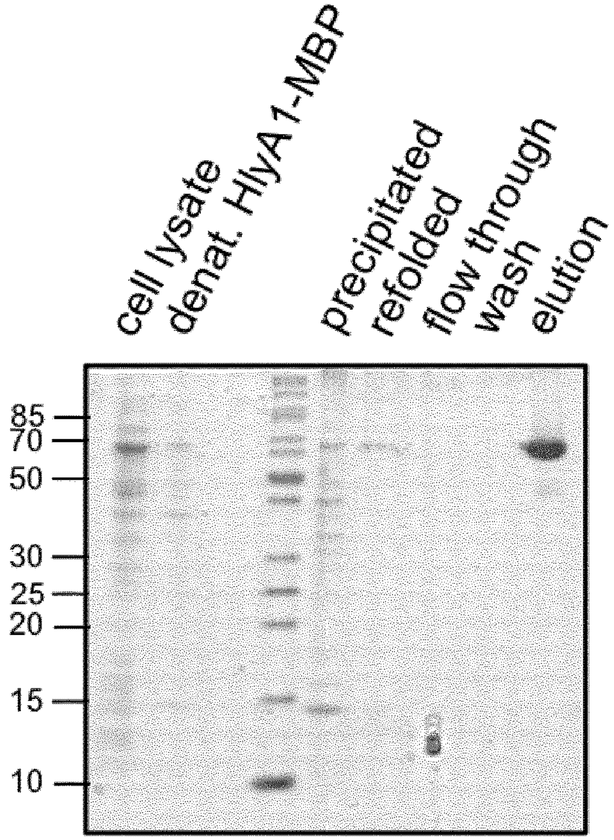

FIG. 10 shows a binding experiment of refolded HlyA1-MBP and amylose resin. HlyA1-MBP was expressed in *E. coli* (lane "cell lysate") and IBs of HlyA1-MBP were prepared (lane "denat. HlyA1-MBP"), denaturated and refolded in the presence of $Ca^{2+}$. Some HlyA1-MBP precipitated during refolding (lane "precipitated") and soluble HlyA1-MBP (lane "refolded") was loaded to amylose resin. HlyA1-MBP bound to amylose and no protein remained within the "flow through". After washing, HlyA1-MBP was eluted by maltose (lane "elution").

Figure 11:
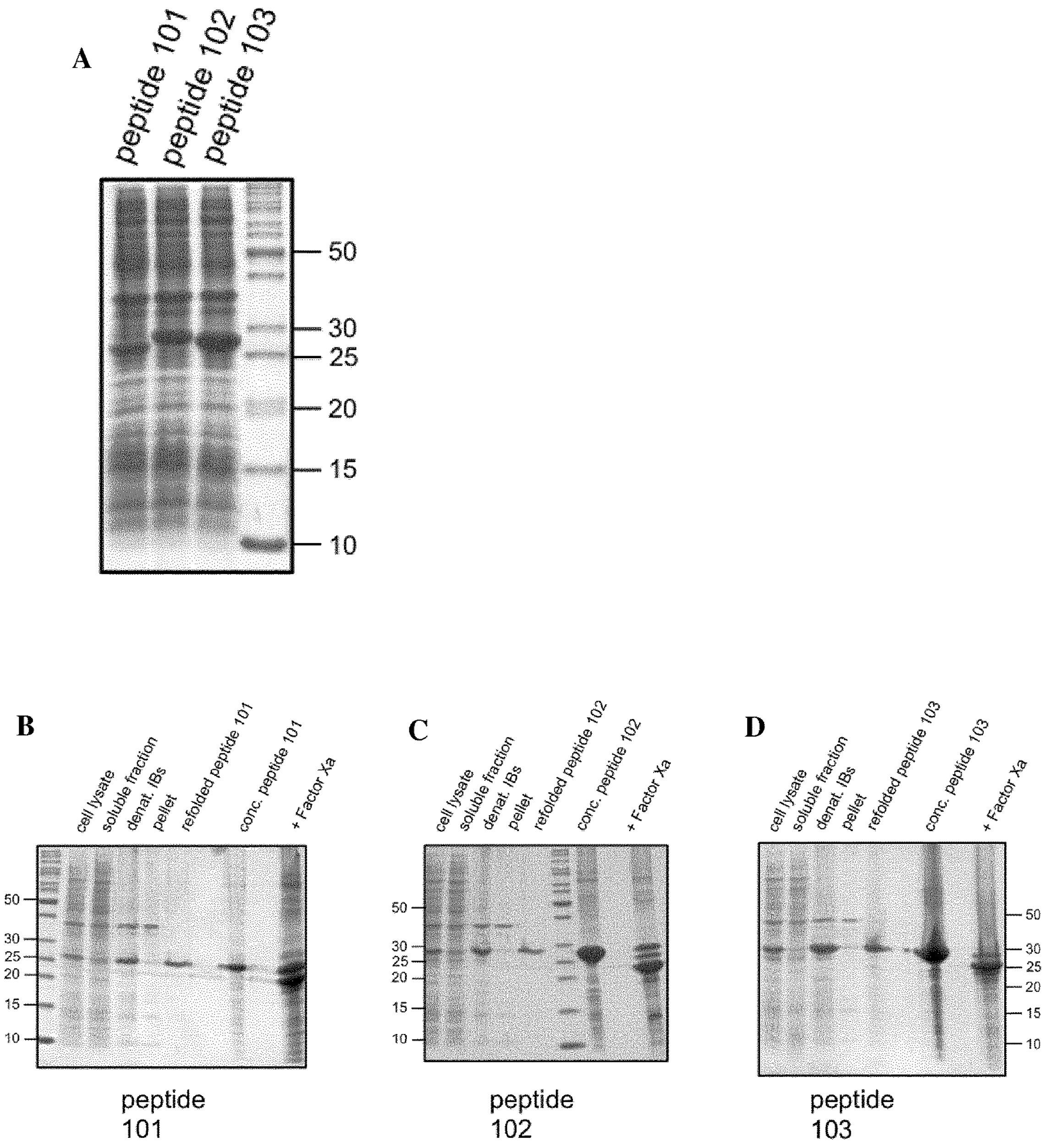

FIG. 11 shows the production of peptides 101, 102 and 103. A: Expression of HlyA1 fused to peptides 101, 102 and 103. B-D: Purification scheme of HlyA1 fused to peptide 101, 102 and 103. Cells expressing the corresponding fusion proteins were broken and cell lysates (lane "cell lysates") were centrifuged. No visible fusion proteins were in the soluble fraction (lane "soluble fraction") and fusion proteins aggregated as IBs. IBs were denaturated (lane "denat. IBs") and refolded in the presence of $Ca^{2+}$. Fusion proteins were efficiently refolded with $Ca^{2+}$ ("refolded peptide 10X") and no proteins precipitated ("pellet"). Renaturated fusion proteins were incubated with Factor Xa and peptides 101, 102 and 103 were separated from HlyA1 (lane "Factor Xa"). An unspecific cleavage product occurred in all cases (see lane "+Factor Xa").

Figure 12:
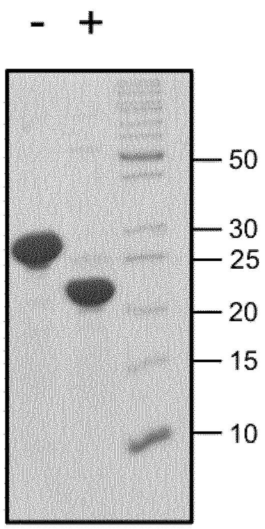

FIG. 12 shows Factor Xa digestion experiments with peptide 103 fused to HlyA1-R210D (encoded by plasmid pIAR_112). Refolded IBs (lane "–") were incubated with Factor Xa ("+") and samples were analysed by SDS-PAGE. No unspecific cleavage product occurred (compared to the results shown in FIG. 11).

Figure 13:
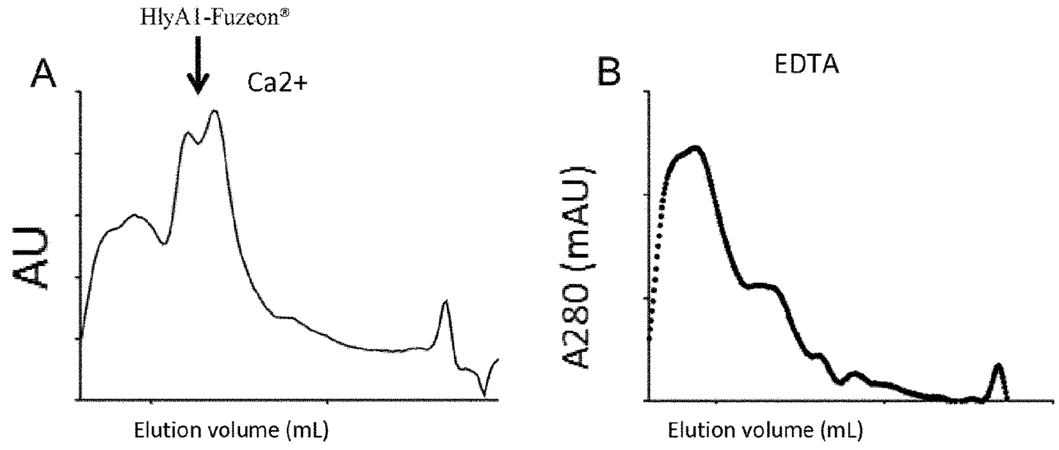
Figure 13:
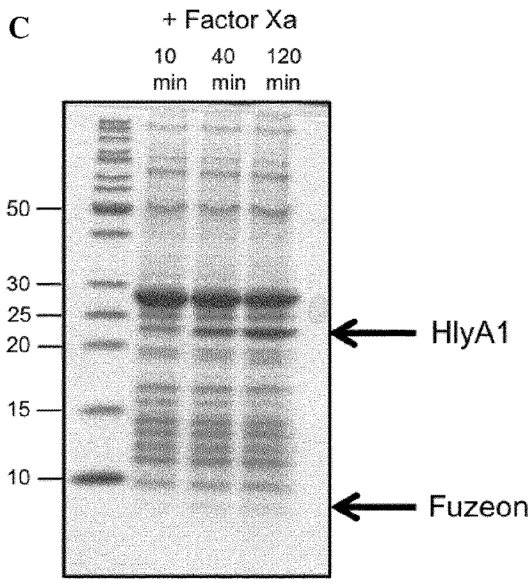

FIG. 13 shows the production of Fuzeon®. HlyA1-Fuzeon® was refolded in the presence of $Ca^{2+}$ (A) or EDTA (B) and loaded onto a Superdex 75 16/60 column. The arrow indicates the position of HlyA1-Fuzeon®. C: HlyA1-Fuzeon® was refolded in the presence of $Ca^{2+}$ and incubated with Factor Xa for 10 min, 40 min and 120 min. The arrows indicate the position of the cleavage products HlyA1 and Fuzeon®.

Figure 14:
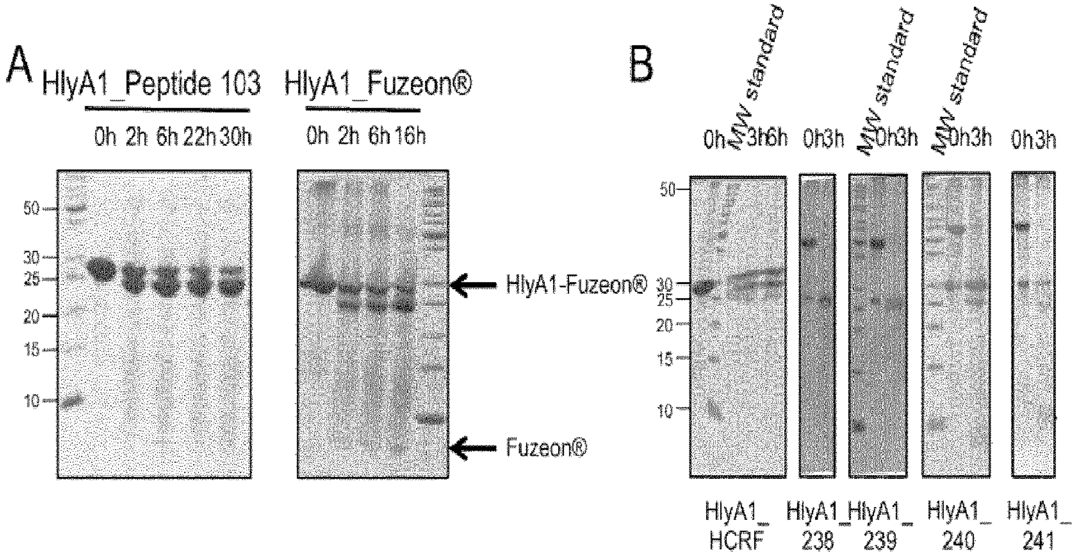

FIG. 14 shows experiments of IBs of HlyA1 M88A-Met-peptide 103 that were denaturated and incubated with CNBr for indicated periods. Samples were analyzed by SDS-PAGE. The cleavage product HlyA1 M88A-Met is visible on the gel. No unspecific cleavage products were obtained. Since peptide 103 was not stained by CBB (presumably due to its relative small molecular weight), it was purified by HPLC and de-novo sequenced by mass spectrometry. Using such method, peptide 103 was identified.

Figure 15:
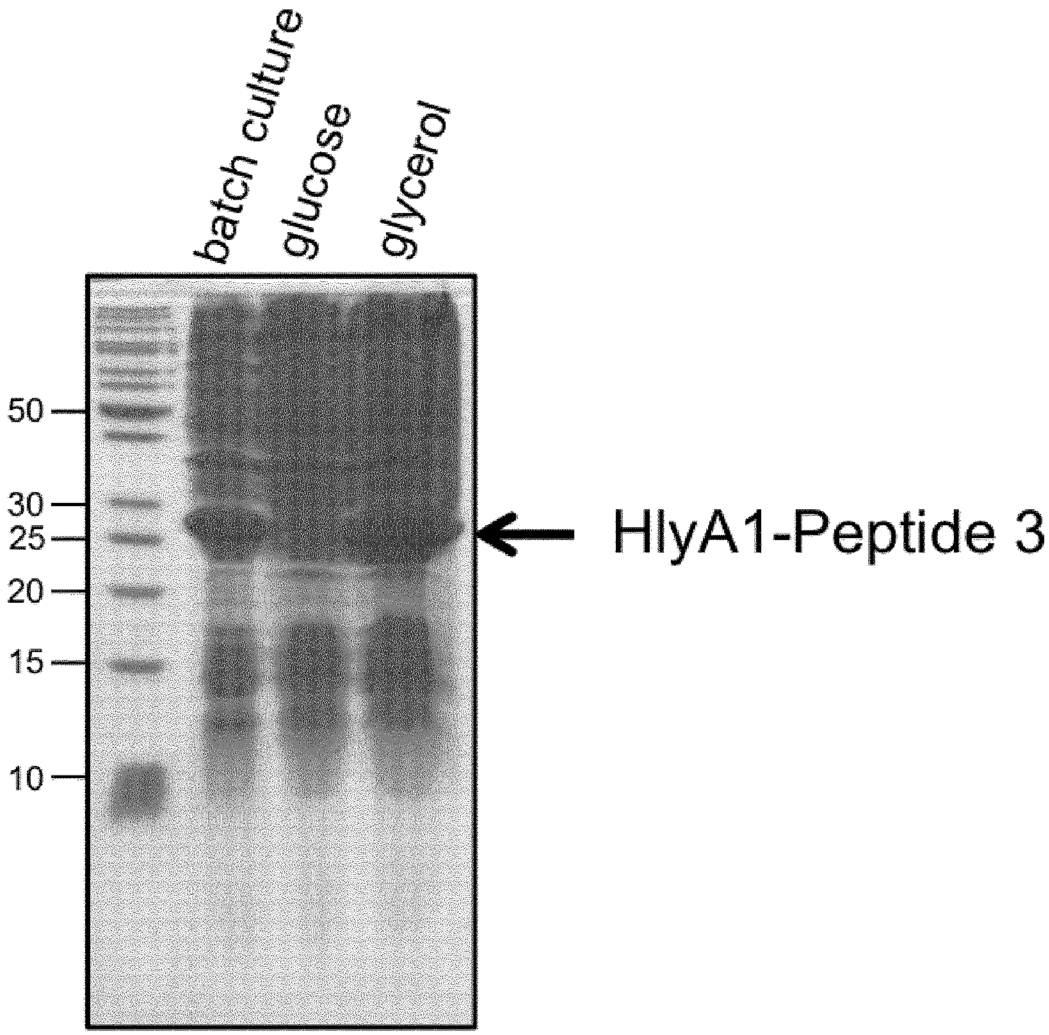

FIG. 15 shows the expression analyses of HlyA1 M88A-Met-peptide 3 in batch cultures and fermentation. *E. coli* cells carrying plasmid pIAR_115 were incubated in batch cultures (left lane), or by fermentation with glucose (middle lane) or glycerol (right lane) as feed. High cell densities (>50) were obtained by fermentation with glucose and glycerin as feed. However, glucose seems to repress the expression of the fusion protein under the used conditions. In the presence of glycerol, in contrast, high cell densities and high expression levels were achieved.

DETAILED DESCRIPTION OF THE INVENTION

The terms used herein have, unless explicitly stated otherwise, the following meanings.

"At least one", as used herein, relates to one or more, in particular 1, 2, 3, 4, 5, 6, 7, 8, 9, 10 or more.

"Isolated" or "isolating", as interchangeably used herein in relation to a molecule, means that said molecule has been at least partially separated from other molecules that are naturally associated with said molecule. "Isolated" may mean that the molecule has been purified to separate it from other molecules and components, such as other proteins and nucleic acids and cellular debris which may originate from a host cell.

"Nucleic acid" as used herein includes all natural forms of nucleic acids, such as DNA and RNA.

Preferably, the nucleic acid molecules are DNA. "Nucleic acid sequence identity" as used herein, means that the residue at a given position is identical to that at a corresponding position of a reference nucleic acid. The preferred nucleic acid sequence identity of the present invention is 80%, more preferred 90% or still more preferred 95%.

The term "fragment", as used herein in connection with a nucleic acid molecule, relates to a nucleic acid sequence which is compared to its reference nucleic acid sequence shortened by one or more 3' or 5' terminal nucleotides. The shortening occurs at the 3'-end, the 5'-end or both so that a contiguous strand of nucleotides of the reference sequence remains. The fragment has preferably a length of at least 20, more preferably at least 50 nucleotides.

The term "peptide" is used throughout the specification to designate a polymer of amino acid residues connected to each other by peptide bonds. A peptide according to the present invention has 2-100 amino acid residues.

The terms "protein" and "polypeptide" are used interchangeably throughout the specification to designate a polymer of amino acid residues connected to each other by peptide bonds. A protein or polypeptide according to the present invention has preferably 100 or more amino acid residues.

The terms "protein of interest", "PrOI" or "peptide of interest", "PeOI", as used herein, relate to any gene product that is expressed via recombinant expression. The term "a peptide or protein of interest" as disclosed herein covers any naturally or non-naturally occurring peptide or protein. In some embodiments, the PeOI or PrOI is a non-natural/synthetic peptide or protein. Synthetic in this connection means that the sequence of the peptide or protein has been artificially designed. Thus, a sequence encoding for a PeOI or PrOI may comprise a nucleic acid sequence encoding for one, two or more naturally occurring peptides or proteins. These naturally occurring peptides or proteins may have been further modified, e.g., by mutagenesis of the encoding sequence.

The term "an N-terminal fragment" relates to a peptide or protein sequence which is in comparison to a reference peptide or protein sequence C-terminally truncated, such that a contiguous amino acid polymer starting from the N-terminus of the peptide or protein remains. In some embodiments, such fragments may have a length of at least 10 amino acids.

The term "a C-terminal fragment" relates to a peptide or protein sequence which is in comparison to a reference peptide or protein sequence N-terminally truncated, such that a contiguous amino acid polymer starting from the C-terminus of the peptide or protein remains. In some embodiments, such fragments may have a length of at least 10 amino acids.

The term "fusion protein" as used herein concerns peptides and proteins which are N- or C-terminally connected to each other. Such fusion proteins may be encoded by nucleic acid sequences which are operably fused to each other. In certain embodiments, a fusion protein refers to at least one PeOI or PrOI C-terminally fused to a polypeptide chain according to the invention, for example a polypeptide chain comprising HlyA or a fragment thereof or a homolog thereof.

Generally, the skilled person understands that for putting the present invention into practice any nucleotide sequence described herein may or must comprise an additional start and/or stop codon or that a start and/or stop codon of any of the sequences described herein may or must be deleted depending on the nucleic acid construct used. The skilled person will base this decision, e.g., on whether a nucleic acid sequence comprised in the nucleic acid molecule of the present invention is to be translated and/or is to be translated as a fusion protein.

The term "introducing" in relation to a nucleic acid molecule, as used herein, refers to the uptake and incorporation of exogenous DNA into a host cell. Such uptake of the nucleic acid molecule may depend on the natural competence of the host cell or on transfection methods such as electroporation or calcium chloride transformation which are well known in the art.

The term "host cell" as used herein relates to an organism that harbors the nucleic acid molecule or a vector encoding the recombinant PeOI or PrOI. In preferred embodiments the host cell is a prokaryotic cell. In more preferred embodiments the host cell is *E. coli* which may include but is not limited to BL21, DH1, DH5α, DM1, HB101, JM101-110, K12, Rosetta(DE3)pLysS, SURE, TOP10, XL1-Blue, XL2-Blue and XL10-Blue strains.

The terms "expression" or "expressed", as interchangeably used herein, relate to a process in which information from a gene is used for the synthesis of a gene product. In cell-based expression systems the expression comprises transcription and translation steps.

The term "recombinant expression", as used herein, relates to transcription and translation of an exogenous gene in a host organism. Exogenous DNA refers to any deoxyribonucleic acid that originates outside of said organism. The term "heterologous" as used herein in relation to proteins refers to a protein that is expressed from an exogenous DNA. This also includes proteins that are expressed from nucleic acid sequences which are identical to endogenous nucleic acid sequences and that were artificially duplicated.

The term "production", as used herein in relation to a recombinant peptide or protein, means that a recombinant peptide or protein is expressed in a host cell and is subsequently isolated from other molecules of the host cell.

"Culturing", "cultivating" or "cultivation", as used herein, relates to the growth of a host cell in a specially prepared culture medium under supervised conditions. The terms "conditions suitable for recombinant expression" or "conditions that allow expression" relate to conditions that allow for production of the PrOI in host cells using methods known in the art, wherein the cells are cultivated under defined media and temperature conditions. The medium may be a nutrient, minimal, selective, differential, or enriched medium. Preferably, the medium is a minimal culture medium. Growth and expression temperature of the host cell may range from 4° C. to 45° C. Preferably, the growth and expression temperature range from 30° C. to 39° C. The term "expression medium" as used herein relates to any of the above media when they are used for cultivation of a host cell during expression of a protein.

The term "subjecting" as used herein means that various components, for instance proteins and a buffer, are brought into contact.

The terms "inclusion body" or "IB", as interchangeably used herein, relate to nuclear or cytoplasmic aggregates of substances, for instance proteins. IB s are undissolved and have a non-unit lipid membrane. In the method of the present invention, the IBs mainly consist of the fusion protein comprising at least one PeOI or PrOI and at least one allocrite of a T1SS or a fragment thereof.

The terms "substrate" or "allocrite", as interchangeably used herein, relate to a solute that may be cargo of a T1SS.

The substrate or allocrite is a protein that contains specific peptide sequence motives, such as GG repeats and the secretion signal, that allow the transportation via the T1SS.

The terms type 1 secretion system" or "T1SS" as interchangeably used herein relate to a protein complex which consists of three protein subunits: an ABC transporter protein, a MFP, and an OMP. The ABC transporters are transmembrane proteins that utilize the energy of adenosine triphosphate (ATP) hydrolysis to carry out certain biological processes including translocation of various substrates across membranes. Proteins of the MFP family function as auxiliary proteins or 'adaptors', connecting a primary porter in the cytoplasmic membrane of a Gram-negative bacterium with an outer membrane factor protein that serves a porin or channel function in the outer membrane. Therefore, the tripartite protein complex allows the transport of various molecules, such as ions, drugs and proteins to pass the inner and outer membrane of Gram-negative bacteria. A subgroup of T1SS substrates are RTX (repeats in toxins) toxins.

The term "functional three-dimensional conformation" as used herein in relation to proteins refers to the structure of a protein which allows said protein to have a specific activity such as substrate catalysis, protein specific localization or interaction with other proteins that is at least 5%, 10%, 20%, 40% or 50%, or more preferably at least 80%, or even more preferably 100% of the activity of the same protein in its native conformation. A functional three-dimensional conformation usually requires that the protein is soluble. The native conformation of a protein is its properly folded and/or assembled form, which is operative and functional. The native state of a biomolecule may possess all four levels of biomolecular structure, with the secondary through quaternary structure being formed from weak interactions along the covalently-bonded backbone. This is in contrast to the denatured state, in which these weak interactions are disrupted, leading to the loss of these forms of structure and retaining only the biomolecule's primary structure.

The term "inhibiting", as used herein, relates to a detectable and significant reduction of protein activity or gene expression activity caused by an effector molecule. Methods to detect protein activity or gene expression are known in the art.

The present invention relates to methods comprising nucleic acid sequences of substrates/allocrites of Type 1 secretion systems or fragments thereof for the efficient production of recombinant peptides and proteins of interest. The allocrites or fragments thereof improve the expression of peptides and protein of interest as inclusion bodies (IB) and function as IB-tags. Importantly, the allocrites and fragments thereof allow the efficient renaturation of the inclusion bodies into a functional three-dimensional conformation. Therefore, the allocrites or fragments thereof combine the advantages of IB-tags and solubility-tags without the corresponding disadvantages.

Figure 1:
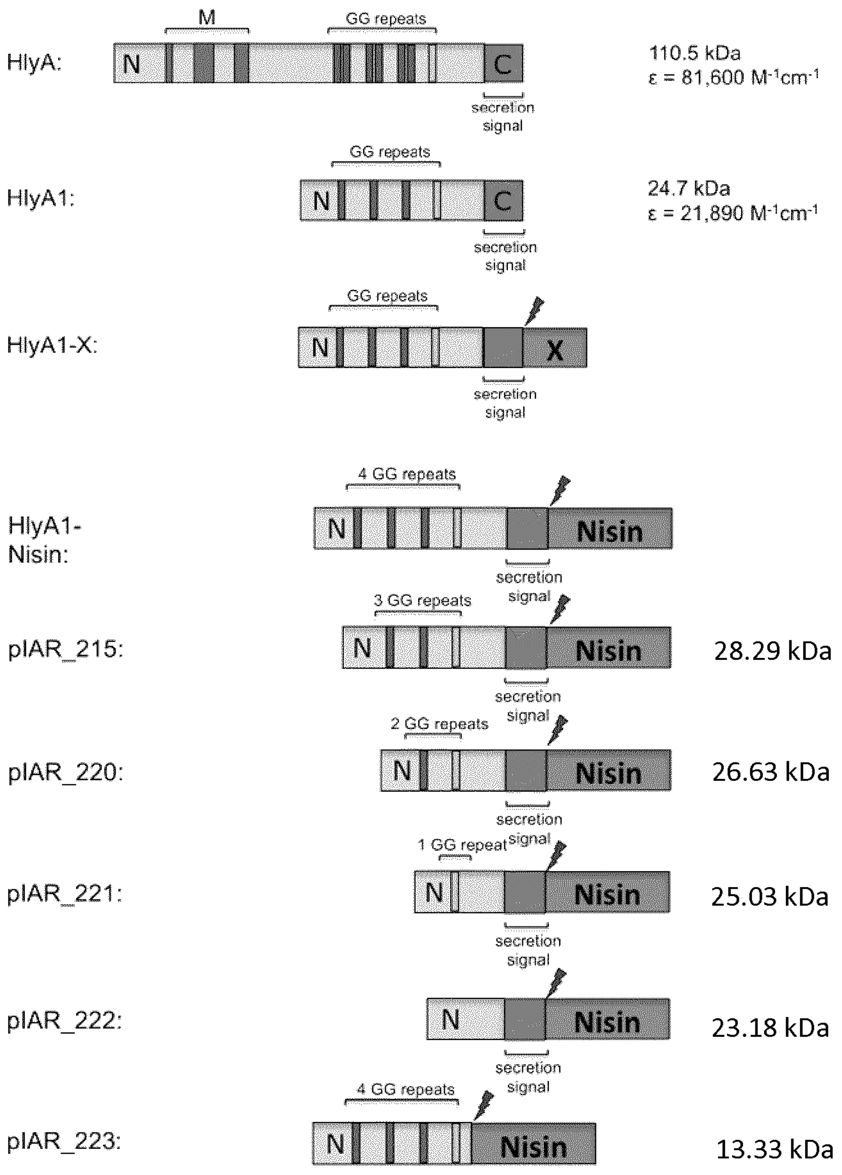
FIG. 1 shows a schematic presentation of some of the used plasmid constructs.

The HlY secretion system is a protein secretion system, which mostly occurs in Gram-negative bacteria. This secretion system belongs to the family of TISS, which transport their substrates in an ATP driven manner in a single step from the cytosol to the extracellular space without an intermediate station in the periplasm. The HlY secretion system comprises HlYB, which represents an ABC transporter, the MFP HlYD, and the universal OMP TolC. The −110 kDa hemolytic toxin HlYA is a transport substrate of the HlY secretion system. On genetic level, the components necessary for HlYA-specific secretion are organized in an operon structure. The nucleic acid sequence encoding for HlYC also forms part of this operon but is not required for HlYA secretion through the HlY secretion system. HlYC catalyzes acylation of HlYA, which renders HlYA hemolytic. HlYA is a protein, which consists of 1024 amino acid residues and requires for its export via the HlY secretion system its C-terminus comprising about 40-60 amino acids called secretion signal. Furthermore, HlYA is characterized by a domain comprising several glycine rich (GG) repeats (GGXGXDXUX (SEQ ID NO: 67), wherein X can be any amino acid, U is a hydrophobic, large amino acid located N-terminal of the secretion signal). GG repeats are the characteristic of the repeats in toxin (RTX) family. The GG repeats bind $Ca^{2+}$ which induces their folding. Hence, in absence of $Ca^{2+}$ the domain comprising the GG repeats is unstructured. The amino acid sequence of one HlYA protein is set forth in SEQ ID NO:2, as encoded by the nucleotide sequence set forth in SEQ ID NO: 1. A fragment of HlYA, which was expressed in enhanced levels compared to the wildtype HlYA and lacks the N-terminal part of HlYA (FIG. 1) was named HlYA1. The amino acid sequence of HlYA1is set forth in SEQ ID NO: 4 whereas the encoding nucleotide sequence is set forth in SEQ ID NO:3.

The present invention is based on the inventors' surprising finding that a PeOI or PrOI fused to at least one allocrite of a T1SS or a fragment thereof leads to the expression of the fusion protein in form of IB even if the non-conjugated PeOI or PrOI alone is expressed in a soluble form. Further, it was found by the present inventors that $Ca^{2+}$ induces the folding of the denaturated IB of the fusion proteins consisting of the allocrite and the PeOI or PrOI into a soluble and functional three-dimensional conformation. Therefore, the allocrites or fragments thereof are bifunctional tags combining the advantages of IB-tags (high yield, high initial purity, immunity against proteolytic degradation) and solubility-tags (soluble, bioactive products) without the corresponding disadvantages (inclusions body-tags: aggregated, non-active products; solubility-tags: rather low yields, low purity, prone to proteolytic degradation).

Thus, in a first aspect, the present invention relates to a method for production of a recombinant PeOI or PrOI, wherein the method comprises: (a) introducing a nucleic acid molecule encoding a fusion protein comprising at least one PeOI or PrOI, and at least one allocrite of a T1SS or a fragment thereof, into a host cell; (b) cultivating the host cell under conditions that allow expression of the fusion protein, wherein the fusion protein is expressed in the form of IB; (c) isolating the recombinant fusion protein from said host cells. Further embodiments may comprise step (d) of subjecting the recombinant fusion protein to conditions that allow the PeOI or PrOI to fold into a functional three-dimensional conformation. In various other embodiments of the first aspect, the host cell does not express a heterologous ABC transporter, a heterologous MFP and/or a heterologous OMP of the T1SS.

In various embodiments, this aspect of the invention also includes allocrites of a TISS that are selected from the group consisting of HlyA, CyaA, EhxA, LktA, PlLktA, PasA, PvxA, MmxA, LtxA, ApxIA, ApxIIA, ApxIIIA, ApxIVA, Apxl, ApxII, AqxA, VcRtxA, VvRtxA, MbxA, RTX cytotoxin, RtxL1, RtxL2, FrhA, LipA, TliA, PrtA, PrtSM, PrtG, PrtB, PrtC, AprA, AprX, ZapA, ZapE, Sap, HasA, colicin V, LapA, ORF, RzcA, RtxA, XF2407, XF2759, RzcA, RsaA, Crs, CsxA, CsxB, SlaA, SwmA, S111951, NodO, PlyA, PlyB, FrpA, FrpC, FrpC-like or other TISS allocrites as described in Linhartova et al. (Linhartova, I. et al., FEMS Microbiol Rev 34, 1076-1112, FMR231 [pii] 10.1111/j.1574-6976.2010.00231.x) and fragments thereof. In various preferred embodiments, the allocrites are characterized by the presence of at least one GG repeat of the consensus sequence GGxGxDxUx (SEQ ID NO: 67) (wherein X can be any amino acid, U is a hydrophobic, large amino acid). In more preferred embodiments the allocrit of a TISS is HlyA comprising or consisting of the amino acid sequence as set forth in SEQ ID NO:2, a fragment thereof or a polypeptide that has at least 80% sequence identity to the amino acid sequence of SEQ ID NO: 2 or the fragment thereof. In other various embodiments the fragment of HlyA consists of the amino acid sequence as set forth in SEQ ID NO:4 or a polypeptide that has at least 80% sequence identity to the amino acid sequence of SEQ ID NO:4.

In various embodiments, this aspect of the invention also includes homologs of the afore-mentioned sequences of SEQ ID Nos. 1-4. The term "homologous" or "homolog" as used herein refers to a polynucleotide or polypeptide sequence that has a highly similar sequence to or high sequence identity (e.g. 70%, 80%, 90%, 95%, 97.5%, 99% or more) with another polynucleotide or polypeptide sequence or part thereof. With regard to the above nucleic acid molecule, the term homologs thus includes nucleic acid sequences that have at least 70, preferably 80, more preferably 90, even more preferably 95, 97.5 or 99% sequence identity to the nucleotide sequence of the first nucleic acid sequence as defined above. The sequence identity may occur over a continuous stretch of nucleotides or may be discontinuous.

In various embodiments of the first aspect of the invention, the allocrite of a T1SS can be fused to the C-terminus of the PeOI or PrOI. In other various embodiments of the first aspect, the allocrite can be fused to the N-terminus of the PeOI or PrOI.

In one embodiment, the expression medium comprises 20.0 mM or less of $Ca^{2+}$. In a more preferred embodiment the $Ca^{2+}$ concentration in the expression medium is 0.1 mM or less.

In various embodiments, the expression of the endogenous ABC transporter gene, the endogenous MFP gene and/or the endogenous OMP gene of the T1SS or the activity of the corresponding gene products in the host cell is inhibited. In various embodiments, the host cell does not express endogenous ABC transporter, endogenous MFP and/or endogenous OMP of the T1SS. Methods to inhibit the expression of genes such as their deletion or insertion of nucleotide sequences destroying the integrity of the promoter sequence or the gene itself are known in the art. A preferred gene expression activity after deletion or disruption may be less than 35%, 30%, 25%, 20%, 15%, 10% or 5% of the activity measured in untreated cells. In other various embodiments of the invention, the endogenous ABC transporter, the endogenous MFP and/or the endogenous OMP of the type 1 secretion system are inhibited by antibodies or small molecule inhibitors. In preferred embodiments of the invention, the ABC transporter activity is inhibited by orthovanadate or an ATP homologous inhibitor such as 8-azido-ATP. Such ATP mimetics are known in the art. The preferred protein activity after inhibitor treatment may be less than 35%, 30%, 25%, 20%, 15%, 10% or 5% of the activity measured in untreated cells. In other embodiments of the invention, the transport is inhibited or blocked by the allocrite itself, for example by over-expressing the allocrites or the attachment of fusion peptides and proteins.

In other embodiments, the recombinant peptide or protein is exposed to a refolding buffer, wherein the refolding buffer comprises at least 0.01, more preferably 0.01-40 mM of $Ca^{2+}$.

In various embodiments of the methods of the invention, (I) the host cell is a prokaryotic cell; and/or (II) the expression is performed in minimal culture medium; and/or (III) the recombinant fusion peptide or protein is purified using a method selected from affinity chromatography, ion exchange chromatography, reverse phase chromatography, size exclusion chromatography, and combinations thereof; and/or (IV) the method comprises the additional step (e) of contacting the recombinant fusion protein with a protease suitable for cleavage of the fusion protein to yield the allocrite and the PeOI or PrOI as separate molecules; and/or (V) the method comprises a step (e) as defined in (IV) followed by purification of the PeOI or PrOI.

In still another embodiment, the present invention may also relate to a method wherein the at least one PeOI or PrOI is selected from the group consisting of Nisin, HCRF, IFABP, IFNA2, MBP, peptide 101, peptide 102, peptide 103, MAB-40 Mab-42, Fuzeon®, salmon Calcitonin, human Calcitonin, Inhibitor peptide 1, 238, 239, 240 or 241.

The nucleic acid molecule encoding the fusion protein further comprises a regulatory nucleotide sequence that modulates expression of the fusion protein in various embodiments. A preferred regulatory nucleic acid sequence is set forth in SEQ ID NO:39. The term "regulatory nucleotide sequence" as used herein relates to a nucleic acid sequences which are located 5' of a gene and enhance the expression activity of said gene.

The terms "affinity tag" as used herein relates to entities, which are coupled to the PeOI or PrOI and allow enrichment of the tagged PeOI or PrOI using an affinity tag receptor. The term "affinity chromatography" as used herein relates to the complex formation of the tagged peptide or protein and the receptor. In certain embodiments affinity tags may be selected from the group consisting of the Strep-tag® or Strep-tag® II, the myc-tag, the FLAG-tag, the His-tag, the small ubiquitin-like modifier (SUMO) tag, the covalent yet dissociable NorpD peptide (CYD) tag, the heavy chain of protein C (HPC) tag, the calmodulin binding peptide (CBP) tag, or the HA-tag or proteins such as Streptavidin binding protein (SBP), maltose binding protein (MBP), and glutathione-S-transferase.

The term "protease cleavage site" refers to peptide sequence which can be cleaved by a selected protease thus allowing the separation of peptide or protein sequences which are interconnected by a protease cleavage site. In certain embodiments the protease cleavage site is selected from the group consisting of a Factor Xa-, a tobacco edge virus (TEV) protease-, a enterokinase-, a SUMO Express protease-, an IgA-Protease-, an Arg-C proteinase-, an Asp-N endopeptidases-, an Asp-N endopeptidase+N-terminal Glu-, a caspase1-, a caspase2-, a caspase3-, a caspase4, a caspase5, a caspase6, a caspase7, a caspase8, a caspase9, a caspase10, a chymotrypsin-high specificity, a chymotrypsin-low specificity-, a clostripain (Clostridiopeptidase B)-, a glutamyl endopeptidase-, a granzymeB-, a pepsin-, a proline-endopeptidase-, a proteinase K-, a staphylococcal peptidase I-, a Thrombin-, a Trypsin-, and a Thermolysin-cleavage site.

The term chemical cleavage refers to the cleavage of peptide bonds caused by a chemical compound. Such compounds may include, but are not limited to cyanogen bromid (CNBr) cleaving C-terminal to methionine residues, BNPS-skatole, NCS or TFA cleaving C-terminal to tryptophane residues and $Ni^{2+}$ ions cleaving C-terminal to the tetrapeptide S/TXHZ (SEQ ID NO: 68) (X and Z can be any amino acid residues, except X =proline) (Kopera et al., (2012), Plos One 7(5)).

"Fused", as used in the context of this invention, means that the resulting peptides or proteins are directly connected to each other or linked to each other by one or more amino acids, peptides or proteins, e.g., one or more protease cleavage sites and/or affinity tags.

If the PeOI or PrOI comprises two or more naturally occurring peptides or proteins, the two or more peptides or proteins may be separated by protease cleavage sites.

Generally, any peptide or protein may be chosen as PeOI or PrOI. In certain embodiments, the PrOI is a protein which does not form a homo-dimer or homo-multimer. The avoidance of self-interacting peptides or proteins may be advantageous if the recombinant peptide or protein is to be secreted into the cell culture supernatant, because the formation of larger protein complexes may disturb an efficient protein export. However, the PrOI may also be a peptide or protein, which is a subunit of a larger peptide or protein complex. Such a peptide or protein may be isolated after expression and optionally secretion and be suitable for an in vitro reconstitution of the multi peptide or protein complex. In certain embodiments, the PeOI or PrOI is a peptide having less than 100 amino acid residues. If these peptides comprise pre- and/or pro-sequences in their native state after translation the nucleic acid sequence encoding for the PeOI may be engineered to be limited to the sequence encoding the mature peptide. One exemplary peptide is insulin, e.g., human insulin. The secretion of over-expressed peptides and proteins is especially advantageous where the peptide or protein is harmful to the host cell. For this reason, the present invention is particularly advantageous for expression of lipases and proteases which are known to be toxic to the host cell and thus the expression of these proteins by the inventive systems and methods represents a specific embodiment of the present invention.

In various embodiments, the PeOI or PrOI is an enzyme.

The International Union of Biochemistry and Molecular Biology has developed a nomenclature for enzymes, the EC numbers; each enzyme is described by a sequence of four numbers preceded by "EC". The first number broadly classifies the enzyme based on its mechanism.

The complete nomenclature can be browsed at world wide web dot chem dot qmul dot ac dot uk/iubmb/enzyvme/.

Accordingly, a PeOI or PrOI according to the present invention may be chosen from any of the classes EC 1 (Oxidoreductases), EC 2 (Transferases), EC 3 (Hydrolases), EC 4 (Lyases), EC 5 (Isomerases), and EC 6 (Ligases), and the subclasses thereof.

In certain embodiments, the PeOI or PrOI is cofactor dependent or harbors a prosthetic group. For expression of such peptides or proteins, in some embodiments, the corresponding cofactor or prosthetic group may be added to the culture medium during expression.

In certain cases, the PeOI or PrOI is a dehydrogenase or an oxidase.

In case the PeOI or PrOI is a dehydrogenase, in some embodiments, the PeOI or PrOI is chosen from the group consisting of alcohol dehydrogenases, glutamate dehydrogenases, lactate dehyrogenases, cellobiose dehydrogenases, formate dehydrogenases, and aldehydes dehydrogenases.

In case the PeOI or PrOI is an oxidase, in some embodiments, the PeOI or PrOI is chosen from the group consisting of cytochrome P450 oxidoreductases, in particular P450 BM3 and mutants thereof, peroxidases, monooxygenases, hydrogenases, monoamine oxidases, aldehydes oxidases, xanthin oxidases, amino acid oxidases, and NADH oxidases.

In further embodiments, the PeOI or PrOI is a transaminase or a kinase.

In case the PeOI or PrOI is a transaminase, in some embodiments, the PeOI or PrOI is chosen from the group consisting of alanine aminotransferases, aspartate aminotransferases, glutamate-oxaloacetic transaminases, histidinol-phosphate transaminases, and histidinol-pyruvate transaminases.

In various embodiments, if the PeOI or PrOI is a kinase, the PeOI or PrOI is chosen from the group consisting of nucleoside diphosphate kinases, nucleoside monophosphate kinases, pyruvate kinase, and glucokinases.

In some embodiments, if the PeOI or PrOI is a hydrolase, the PeOI or PrOI is chosen from the group consisting of lipases, amylases, proteases, cellulases, nitrile hydrolases, halogenases, phospholipases, and esterases.

In certain embodiments, if the PeOI or PrOI is a lyase, the PeOI or PrOI is chosen from the group consisting of aldolases, e.g., hydroxynitrile lyases, thiamine-dependent enzymes, e.g., benzaldehyde lyases, and pyruvate decarboxylases.

In various embodiments, if the PeOI or PrOI is an isomerase, the PeOI or PrOI is chosen from the group consisting of isomerases and mutases.

In some embodiments, if the PeOI or PrOI is a ligase, the PeOI or PrOI may be a DNA ligase.

In certain embodiments, the PeOI or PrOI may be an antibody. This may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like.

Also contemplated herein are therapeutically active PeOIs and PrOI, e.g., a cytokine.

Thus, in certain embodiments the PeOI or PrOI is selected from the group consisting cytokines, in particular human or murine interferons, interleukins, colony-stimulating factors, necrosis factors, e.g., tumor necrosis factor, and growth factors.

In some embodiments, if the PeOI or PrOI is an interferon, the PeOI or PrOI may be selected from the group consisting of interferon alpha, e.g., alpha-1, alpha-2, alpha-2a, and alpha-2b, alpha-2, alpha-8, alpha-16, alpha 21, beta, e.g., beta-1, beta-1a, and beta-1b, or gamma.

In further embodiments, the PeOI or PrOI is an antimicrobial peptide, in particular a peptide selected from the group consisting of bacteriocines and lantibiotics, e.g., nisin, cathelicidins, defensins, and saposins.

In further embodiments, the PeOI or PrOI is an adhesive peptide with distinct surface specificities, for example for steel, aluminum and other metals or specificities towards other surfaces like carbon, ceramic, minerals, plastics, wood and other materials or other biological materials like cells, or adhesive peptides that function in aqueous environments and under anaerobe conditions.

In further embodiments, the PeOI or PrOI has a length ranging from 2-100 amino acids, wherein said amino acids are selected from the group of the 20 proteinogenic amino acids. More preferably, said PeOI or PrOI are selected from the group of peptides or proteins consisting of DYKDDDD-KMASMTGGQQMGHHHHHH (SEQ ID NO: 45), MGSSAAAAAAAASGPGGYGPENQGPSGPGGYG-PGGP (SEQ ID NO:46), ENREVPPGFTALIKTLRKCKII (SEQ ID NO:47), NLVSGLIEARKYLEWLHRKLKNCKV (SEQ ID NO:48), HHHHHHIEGRAMSILKSPIDERSILK (SEQ ID NO:49), HHHHHHIEGRPPGPPGPPGPPGPPG-PPGPPGPPGPPG (SEQ ID NO:50), HHHHHHIEGRGAP- GAPGSQGAPGLQ (SEQ ID NO:51), GGGRGD-MGSSAAAAAAAASGPGGYGPENQGPSGPGGYGPG GPRGDGGG (SEQ ID NO:52).

Also disclosed herein are PeOIs or PrOI, which are therapeutically active peptides or proteins. In certain embodiments, the PeOI or PrOI is a therapeutically active peptide. In some embodiments, a therapeutically active peptide may be selected from the group consisting of Fuzeon/T20, human calcitonin, salmon calcitonin, human corticotropin release factor, Mab40, Mab42, peptides associated with Alzheimer's disease, exenatide, glatiramer/copaxone, teriparatide/forsteo, romiplostim/nplate, pramlintitde/symlin, thymalfasin/zadaxin, enfuvirtide, andrenocorticotropin hormones (ACTH), brain natriuretic peptide, nesiritide/natrecor, corticoliberin, sermorelin, somatorelin, secretin (human and porcin), terlipressin, sinapultide, teduglutide, vx-001, vasoactive intestinal peptide, avipdadil, linaclotide, and teduglutide.

In certain embodiments, the PeOI or PrOI is a type I secretion substrate. More than 1000 proteins are annotated or have been described as type I secretion substrates in the literature. Many of them have interesting characteristics for the biotechnological usage, in particular hydrolases like proteases and lipases. Suitable proteases and lipases have been described by Baumann et al. (1993) EMBO J 12, 3357-3364; and Meier et al. (2007) J. BIOL. CHEM.: 282(43), pp. 31477-31483. The content of each of these documents is incorporated by reference herein in its entirety.

Of course, the nucleic acid sequence encoding for the at least one PeOI or PrOI may be subjected to mutagenesis and thus lead to a mutated PeOI or PrOI on protein level.

The term "mutation" as used herein relates to a variation in the nucleotide and/or amino acid sequence of a given nucleotide sequence or protein and includes substitutions, deletions, truncations, and insertions. In one specific example, the mutation is a point mutation, i.e. the replacement of one or more nucleotides and/or amino acids in a given sequence. It is understood that if the term "mutation" is used in relation to a protein sequence, that the nucleotide sequence encoding the protein can comprise multiple mutations or modifications, including silent mutations that, for example, serve the purpose to increase expression efficiency (codon-optimization) without changing the amino acid sequence. In the present invention, the mutation is preferably the substitution of one or two amino acids by other amino acids. Alternatively or in addition, the nucleic acid molecule may comprise nucleotide exchanges which do not alter the encoded protein sequence, so called silent mutations. In some embodiments, the mutations, e.g., silent mutations increase the expression and/or secretion efficiency of the peptide or protein encoded by the nucleic acid molecule. Importantly, mutations may be induced throughout the nucleic acid molecule of the present invention. Thus, the mutations may not be limited to sequences encoding for a peptide or protein. Accordingly, also non-coding sequence stretches may be subjected to mutagenesis. This type of mutation also falls within the scope of the term silent mutation. The mutagenesis of non-coding sequences may be advantageous, e.g., for the achievement of an improved expression and/or secretion of a peptide or protein encoded by a different sequence stretch within the nucleic acid molecule.

The term "mutagenesis" as used herein means that the experimental conditions are chosen such that the amino acid naturally occurring at a given sequence position of a protein sequence can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the invention.

The term "random mutagenesis" means that no predetermined single amino acid (mutation) is present at a certain sequence position but that one of at least two different amino acids can be incorporated with a certain probability at a predefined sequence position during mutagenesis.

"Codon-optimized" means that codons encoding one amino acid residue are replaced by a different codon encoding the same amino acid, but being more frequently used by a given host organism for this particular amino acid. It is understood that such nucleotide sequences that encode a homologous polypeptide may have high sequence variability so that sequence identity between the nucleic acid molecules encoding the same or homologous polypeptides may be low.

The natural coding sequence of a protein sequence, i.e. the respective gene segment of an enzyme, can be used as a starting point for the mutagenesis of the amino acid positions selected in the present invention. For the mutagenesis of the recited amino acid positions, the person skilled in the art has at his disposal the various established standard methods for site-directed mutagenesis (Sambrook, J. et al. (2001) Molecular Cloning: A Laboratory Manual, 3rd Ed., Cold Spring Harbor Laboratory Press, Cold Spring Harbor, N.Y.). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine, cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence (V=adenine, guanine, or cytosine); use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. Another possibility is the use of codons NDT or NDC (wherein D=adenine, guanine, or thymine) as this provides a 1:1 ratio between the number of codons and the encoded amino acids, thus reduces the screening effort, and leads to a balanced set of 12 polar, non-polar, aromatic, non-aromatic, hydrophilic and hydrophobic amino acid residues (Arg, Asn, Asp, Cys, Gly, His, Ile, Leu, Phe, Ser, Tyr, Val (Reetz M T et al., 2008, ChemBioChem, 21; 9(11): 1797-804)).

In certain embodiments, the PeOI or PrOI comprises a deletion of at least 10, 20, 30, 40, 50, or more N- and/or C-terminal amino acid relative to the wildtype peptide or protein sequence.

In various embodiments, the PeOI or PrOI is chosen from the group consisting of MBP, lipase CalB, protease SprP, hydrolase PlaB, hydrolase PlaK, hydrolase PlbF, lipase TesA, Vif, human interferon alpha-1, alpha-2, alpha-8, alpha-16, alpha-21, human interferon beta, human interferon gamma, murine interferon alpha, murine interferon gamma, IFABP, Cas2, affibody protein ZA3, nisin, corticotropin release factor, amyloid-beta peptide, exenatide, Fuzeon/T20, salmon calcitonin, Mab40, Mab42, lipase LipA, SprP, the HIV-1 protein Vif, and human calcitonin.

The PeOI or PrOI may be cloned into a vector. In certain embodiments, the vector is selected from the group consisting of a pSU-vector, pET-vector, a pBAD-vector, a pK184-vector, a pMONO-vector, a pSELECT-vector, pSELECT-Tag-vector, a pVITRO-vector, a pVIVO-vector, a pORF-vector, a pBLAST-vector, a pUNO-vector, a pDUO-vector, a pZERO-vector, a pDeNy-vector, a pDRIVE-vector, a pDRIVE-SEAP-vector, a HaloTag® Fusion-vector, a pTARGET™-vector, a Flexi®-vector, a pDEST-vector, a pHIL-vector, a pPIC-vector, a pMET-vector, a pPink-vector, a pLP-vector, a pTOPO-vector, a pBud-vector, a pCEP-vector, a pCMV-vector, a pDisplay-vector, a pEF-vector, a pFL-vector, a pFRT-vector, a pFastBac-vector, a pGAPZ-vector, a pIZ/V5-vector, a pLenti6-vector, a pMIB-vector, a pOG-vector, a pOpti-vector, a pREP4-vector, a pRSET-vector, a pSCREEN-vector, a pSecTag-vector, a pTEF1-vector, a pTracer-vector, a pTrc-vector, a pUB6-vector, a pVAX1-vector, a pYC2-vector, a pYES2-vector, a pZeo-vector, a pcDNA-vector, a pFLAG-vector, a pTAC-vector, a pT7-vector, a Gateway®-vector, a pQE-vector, a pLEXY-vector, a pRNA-vector, a pPK-vector, a pUMVC-vector, a pLIVE-vector, a pCRUZ-vector, a Duet-vector, and other vectors or derivatives thereof. In preferred embodiments the vector is the pSU-vector.

The vectors of the present invention may be chosen from the group consisting of high, medium and low copy vectors.

The above described vectors may be used for the transformation or transfection of a host cell in order to achieve expression of a peptide or protein which is encoded by an above described nucleic acid molecule and comprised in the vector DNA.

The host cell may be specifically chosen as a host cell capable of expressing the gene. In addition or otherwise, in order to produce a peptide or protein, a fragment of the peptide or protein or a fusion protein of the peptide or protein with another polypeptide, the nucleic acid coding for the peptide or protein can be genetically engineered for expression in a suitable system. Transformation can be performed using standard techniques (Sambrook, J. et al. (2001), supra).

Prokaryotic or eukaryotic host organisms comprising such a vector for recombinant expression of a PeOI or PrOI as described herein form also part of the present invention. Suitable host cells can be prokaryotic cell. In certain embodiments the host cells are selected from the group consisting of gram positive and gram negative bacteria. In some embodiments, the host cell is a gram negative bacterium, such as *E. coli*. In certain embodiments, the host cell is *E. coli*, in particular *E. coli* BL21 (DE3) or other *E. coli* K12 or *E. coli* B834 or *E. coli* DH5α or XL-1 derivatives. In further embodiments, the host cell is selected from the group consisting of *Escherichia coli* (*E. coli*), *Pseudomonas, Serratia marcescens, Salmonella, Shigella* (and other enterobacteriaceae), *Neisseria, Hemophilus, Klebsiella, Proteus, Enterobacter, Helicobacter, Acinetobacter, Moraxella, Helicobacter, Stenotrophomonas, Bdellovibrio, Legionella*, acetic acid bacteria, *Bacillus, Bacilli, Carynebacterium, Clostridium, Listeria, Streptococcus, Staphylococcus*, and *Archaea* cells. Suitable eukaryotic host cells are among others CHO cells, insect cells, fungi, yeast cells, e.g., *Saccharomyces cerevisiae, S. pombe, Pichia pastoris.*

The transformed host cells are cultured under conditions suitable for expression of the nucleotide sequence encoding a peptide or protein of the invention. In certain embodiments, the cells are cultured under conditions suitable for expression of the nucleotide sequence encoding a PeOI or PrOI.

For producing the recombinant PeOI or PrOI, a vector is introduced into a suitable prokaryotic or eukaryotic host organism by means of recombinant DNA technology. For this purpose, the host cell is first transformed with a vector comprising a nucleic acid molecule according to the present invention using established standard methods (Sambrook, J. et al. (2001), supra). The host cell is then cultured under conditions, which allow expression of the heterologous DNA and thus the synthesis of the corresponding polypeptide. Subsequently, the polypeptide is recovered either from the cell.

For expression of the peptides and proteins of the present invention several suitable protocols are known to the skilled person.

Generally, any known culture medium suitable for growth of the selected host may be employed in this method. In various embodiments, the medium is a rich medium or a minimal medium. Also contemplated herein is a method, wherein the steps of growing the cells and expressing the peptide or protein comprise the use of different media. For example, the growth step may be performed using a rich medium, which is replaced by a minimal medium in the expression step. In certain cases, the medium is selected from the group consisting of LB medium, TB medium, 2YT medium, synthetical medium and minimal medium.

In some embodiments, the medium may be supplemented with IPTG, arabinose, tryptophan and/or maltose, and/or the culture temperature may be changed and/or the culture may be exposed to UV light. In various embodiments, the conditions that allow secretion of the recombinant peptide or protein are the same used for the expression of the peptide or protein.

In certain embodiments, the host cell is a prokaryotic cell, such as *E. coli*, in particular *E. coli* BL21 (DE3) and *E. coli* DH5α.

In some embodiments, the entire culture of the host cell, e.g., during growth and expression, is carried out in minimal medium. Minimal medium is advantageous for recombinant peptide or protein expression, as the protein, lipid, carbohydrate, pigment, and impurity content in this medium is reduced and thus circumvents or reduces the need of extensive purification steps.

Furthermore, the inventors found that a supplementation of the refolding buffer with alkaline earth metal salts is advantageous for subjecting the recombinant PeOI or PrOI to fold into a functional three-dimensional conformation. In some embodiments, the final concentration in the refolding buffer is at least 0.01 mM. In certain embodiments, the refolding buffer may be complemented with at least one alkaline earth metal salt selected from the group consisting of a magnesium salt, calcium salt, strontium salt, or barium salt. In some embodiments, the refolding buffer comprises at least 0.01 mM of a calcium salt. The total concentration of at least 0.01 mM earth alkaline metal salt may be achieved by combining several salts from different earth alkaline metals and/or the same earth alkaline metal. If the earth alkaline metal is selected from magnesium salt, calcium salt, strontium salt, or barium salt, the composition may comprise at least 0.01 mM of a single calcium, strontium or barium salt or combinations of several magnesium, calcium, strontium or barium salts, leading to a total concentration of at least 0.01 mM. In particular, a calcium salt concentration of at least 0.01 mM may be achieved by combining several calcium salts leading to a total concentration of at least 0.01 mM. In certain embodiments, the calcium salts are selected from the group consisting of $CaCl_2$, $CaCO_3$, $Ca(OH)_2$, $CaSO_4.2H_2O$, $Ca_3(PO_4)_2$, $Ca(CH_3COO)_2.H_2O$, and $Ca(C_2H_3O_2)_2$. In specific embodiments, the buffer contains at least 0.01 mM $Ca^{2+}$ ions. In various embodiments the concentration of $Ca^{2+}$ in the refolding buffer is in the range of 20-100 mM. In a preferred embodiment, the $Ca^{2+}$ concentration is 20 mM.

In various embodiments, the method also encompasses the purification the recombinant peptide or protein, wherein the recombinant peptide or protein is purified using a method selected from affinity chromatography, ion exchange chromatography, reverse phase chromatography, size exclusion chromatography, and combinations thereof.

In several embodiments, the method may comprise the treatment of the recombinant peptide or protein with a protease suitable for cleavage of a protease cleavage site within the recombinant peptide or protein. In some embodiments, the recombinant peptide or protein is purified prior to proteolytic cleavage using one or more methods disclosed above. Also after cleavage of the recombinant peptide or protein, the method may comprise a further purification step as defined above. Thus, in some embodiments the recombinant peptide or protein is purified, subjected to proteolytic cleavage and the PeOI or PrOI is further purified.

By the introduction of a site-specific protease cleavage site between HlyA or fragments of HlyA and the PeOI (e.g. the protease Factor Xa) or by chemical cleavage, the allocrit and the PeOI or PrOI can be separated and the resulting PrOI or PeOI is produced without any additional/artificial amino acid. Chemical cleavage may be processed by cyanogenbromid, B-bromosuccinimide, N-chlorosuccinimide, BNPS-skatole (3-bromo-3-methyl-2-(o-nitrophenylsulfenyl)indolenine) or $Ni^{2+}$ ions. Such methods are well known in the art.

After the purification and/or secretion of the peptide or protein of the present invention, in particular of the PeOI or PrOI, the peptide or protein may be fused to a moiety that extends the serum half-life of the peptide or protein. Such moieties are well-known in the art and those skilled in the art may resort to routine practice to identify suitable moieties. Exemplary moieties include, but are not limited to an Fc part of an immunoglobulin, a CH3 domain of an immunoglobulin, a CH4 domain of an immunoglobulin, albumin or an albumin fragment, an albumin binding peptide, an albumin binding protein, transferrin, a polyalkylene glycol molecule, hydroxyethyl starch, palmitic acid and other fatty acid molecules. The fusion may be to the N- or C-terminus, but also may be to an amino acid side chain that is amenable to such modification, including cysteine, lysine, serine, threonine, glutamic acid and aspartic acid side chains.

In various other embodiments, cysteine residues in the polypeptide sequence of the peptide or protein of the present invention, e.g., the PeOI or PrOI, may be mutated to other amino acids or deleted, for example to prevent disulphide bridge formation. In other embodiments, the peptide or protein of the invention may include one or more amino acids that are mutated to cysteine residues in order to generate coupling sites for modifications, for example for the conjugation to other compounds, such as polyethylene glycol (PEG), biotin, peptides or proteins, or for the formation of non-naturally occurring disulphide linkages. Thus, the above described method may also comprise the coupling of compounds, such as polyethylene glycol (PEG), biotin, peptides or proteins, or for the formation of non-naturally occurring disulphide linkages.

EXAMPLES

Materials and Methods

Proteins were expressed in *Escherichia coli* BL21 (DE3) (Novagen). All oligonucleotides were purchased from Eurofins MWG. All enzymes were purchased from NEB, Clontech, Invitrogen or Fermentas.

1. In-Fusion HD Cloning 1.1 Linearization of the Vector

The vector was linearized by PCR using oligonucleotides that anneal at the desired positions. For example, the plasmid pSU-HlyA1 was amplified with the oligonucleotides pSUrev_lin_for (5'-TAATATATTAATTTAAATGATAGCAATCTTACT-3') (SEQ ID NO:40) and pSUrev_X_rev (5'-TGCTGATGTGGTCAGG-3) (SEQ ID NO:41). If desired, the oligonucleotides encoded a protease cleavage site, i. e. the oligonucleotide pSUrev_lin_Xa_rev (5'-ACGGCCATCAATTGCTGATGTGGTCAGG-3') (SEQ ID NO:42) encodes a Factor Xa cleavage site (primary sequence: IDGR). PCR products were treated with DpnI to destroy the PCR template. If desired, PCR products were purified with a PCR Purification Kit (Qiagen, Hilden) or by Gel Extraction (Qiagen, Hilden).

1.2. Amplification of the Inserts

Genes of interest were amplified by PCR with oligonucleotides that anneal to the gene of interest and that carry 5' overhangs being complementary to the linearized vector. For instance, the overhang of the forward oligonucleotide (5'-GCAATTGATGGCCGT-3') (SEQ ID NO:43), was complementary to the oligonucleotide pSUrev_lin_Xa_rev, and the overhang of the reverse oligonucleotide (5'-TAAATTAATATATTA-3) (SEQ ID NO:44) was complementary to the oligonucleotide pSUrev_lin_for. If desired, the PCR products were purified with a PCR Purification Kit (Qiagen, Hilden) or by Gel Extraction (Qiagen, Hilden).

1.3. In-Fusion HD Reaction

This reaction was performed in accordance to the manual (ClonTech).

1.4. Transformation

Suitable *E. coli* cells were transformed with the In-Fusion product, grown overnight on agar plates containing the desired selection marker, and single colonies were picked for the preparation of the plasmids. The sequences of all plasmids were verified by sequencing.

2. Insertion or Deletion of Nucleotide(s) by PCR and Subsequent Ligation 2.1. Phosphorylation Oligonucleotides were ordered with a 5'-Phosphate or phosphorylated at their 5' with the T4 Polynucleotide Kinase (NEB) according to the manual.

2.2. Amplification of the Plasmid

For the deletion of nucleotides, plasmids were amplified by PCR at the desired nucleotides with phosphorylated oligonucleotides. For insertions, plasmids were amplified by PCR at the desired nucleotides with 5'-phosphorylated oligonucleotides that carried the nucleotides to be inserted at their 5'. PCR reactions were incubated with DpnI at 37° C. to destroy the template DNA, gel-extracted and 50 ng linearized plasmids were ligated overnight at 4° C. with Ligase (NEB) and the recommended reaction buffer. Ligation samples were used for the transformation of *E. coli*, the plasmids were isolated and the sequences were verified by sequencing.

3. Site-Directed Mutagenesis

Mutagenesis was performed according to the Site-Directed Mutagenesis Protocol of (Agilent).

4. Overexpression of the Genes of Interests

*E. coli* was transformed with the desired plasmid and grown in 2YT medium at 37° C. and shaking. The expression was induced with 1 mM IPTG and the cells were grown for 4 h. Typically, the OD600 of the cultures was ranging between 5 and 8. Cells were harvested by centrifugation and stored at −20° C.

5. Preparation of IBs

Cells were resuspended in resuspension buffer (10 mM Tris-HCl, 120 mM NaCl, 1 mM EDTA, pH 7.3) and broken by three passages through a cell disruptor (2.5 kbar, Constant Systems). Cell lysates were centrifuged for 20 min, 13.500×g, 4° C., the pellet was washed with resuspension buffer supplemented with 0.5% Triton-X-100 and 1 mM DTT. After centrifugation for 20 min, 13.500×g, 4° C., the pellet was washed with resuspension buffer. After centrifugation, the pellet containing the IBs was solubilized/denaturated at 4° C./room temperature in denaturation buffer (10 mM Tris-HCl, 120 mM NaCl, 0.1 mM ETDA, 10% glycerol, 6 M guanidinium-hydrochlorid,/8 M urea pH 7.3). Denaturated IBs were stored at −20° C.

6. Chemical Cleavage with Cyanogen Bromid (CNBr)

Denaturated IBs were supplemented with 0.1 N HCl and 100-fold molar excess of CNBr (Sigma-Aldrich). Reaction was incubated at room temperature.

7. Chemical Cleavage with 3-Bromo-3-methyl-2-(2-nitrophenylthio)-3H-indole (BNPS-Skatole)

IBs were solubilized in 50% $H_2O$ and 50% acetic acid and incubated with BNPS-skatole (dissolved in acetic acid) at room temperature or other temperatures. More details are described in Vestling et al. (1994) RCM 8, 786-790; and Rahali et al. (1999) Journal of protein chemistry 18, 1-12.

8. Chemical Cleavage with N-Chlorosuccinimide (NCS)

IBs were dissolved in 8 M urea, pH 7.3, and mixed with NCS (dissolved in acetic acid). More details are described in Shechter et al. (1976) Biochemistry 15, 5071-5075; and Lischwe et al. (1977) The Journal of biological chemistry 252, 4976-4980.

9. Chemical Cleavage with Trifluoroacetic Acid (TFA)

IBs were dissolved in TFA. DMSO and HCl (37%) were added to start the cleavage reaction. The reaction mixture was incubated at different temperatures. More details are described in Dimarchi et al. (1987) Process for selective peptide bond cleavage, EP0288272A3.

10. Refolding of IBs

Denaturated IBs were diluted to 0.2 mg/mL in denaturation buffer and refolded either while being dialyzed against refolding buffer (10 mM Tris-HCl, 120 mM NaCl, pH 7.3) supplemented with 20 mM $CaCl_2$ or 0.2 mM EDTA or by diluting denaturated IBs immediately in resuspension buffer (supplemented with 20 mM $CaCl_2$ or 0.2 mM EDTA) to 0.2 mg/mL. Components of the refolding buffer might be altered and other buffers (Hepes, CAPS, Bicine, Citrate etc.), pH values ranging from 0-14, salt concentrations and additional supplements might be used. The protein concentration for the refolding might also be altered, for example ranging from 0.01-20 mg/mL. Refolded IBs were centrifuged for 20 min, 50.000×g, 4° C. and the supernatant was used for further experiments.

11. Concentration of Protein Samples

Proteins were concentrated by ultrafiltration (Amicon Filter devices, Millipore) with the desired molecular weight cut-offs (MWCO).

12. Immobilized Metal-Ion Affinity Chromatography (IMAC)

IMACs were performed with FPLC systems (Äkta Systems, GE Healthcare). Refolded proteins, which contained a His-tag, were loaded to an IMAC column equilibrated in IMAC buffer A (10 mM Tris-HCl, 100 mM KCl, 10% glycerol, 10 mM imidazole, pH 7.3) supplemented with either 0.1 mM EDTA or 20 mM $CaCl_2$. Proteins were eluted with a linear gradient from 10 to 500 mM imidazole.

13. Factor Xa Digestion

50 μg proteins were incubated with 1 μg Factor Xa (NEB) either at 4° C., 20° C. or 25° C. and samples were taken at various time points.

14. Size-Exclusion Chromatography (SEC)

Proteins were loaded onto a SEC column (Superdex 75 16/60, Superdex 75 10/300, Superdex 200 16/60, Superdex 200 10/300, GE Healthcare) equilibrated in the corresponding buffer.

15. HPLC

Analytical RP-HPLC was performed with a LiChrospher WP 300 RP-18 end capped column (Merck) at room temperature. Refolded/denaturated IBs were injected and eluted by mixing the aqueous buffer A (0% acetonitrile, 0.1% (v/v) trifluoroacetic acid) with the organic solvent buffer B (100% acetonitrile, 0.1% (v/v) trifluoroacetic acid). Proteins or peptides were eluted with a gradient of 0-100% of buffer B. Chromatograms show the absorbance at 220 nm. The eluent was fractionated, collected and the solvent was evaporated.

16. Fluorescence Spectroscopy with DAUDA 11-(Dansylamino)undecanoic acid (DAUDA, Cayman Chemical) was prepared as a 1 mM stock solution in 50% isopropanol and 50% buffer (20 mM $KH_2PO_4$, 0.25 mM EDTA, pH 7.3) and further diluted to the appropriate concentrations with buffer. 100 nM protein was used in buffer and a 1 mL silica glass cuvette. The fluorescence signal was recorded at a wavelength of 500 nm after excitation at 350 nm using a Fluorolog®-3 (Horiba) (Kim and Frieden (1998) Protein Sci, 7, 1821-1828). The slit width was adjusted to 4.3 nm for both, the excitation and emission, and the signal was integrated for 0.5 s. Fluorescence signals of DAUDA in buffer in the absence of protein was subtracted as background. The corrected and normalized fluorescence signals were plotted against the DAUDA concentration. Data were fitted using the program Prism 5.

17. Binding Assays to Amylose Resin

Refolded HlyA1-MBP was loaded on amylose resin by gravity flow and after extensive washing, protein was eluted with refolding buffer containing 10 mM maltose.

18. Secretion Assays

*E. coli* cells were transformed with plasmid pK184-HlyBD (encoding the ABC transporter HlyB and the membrane fusion protein HlyD to allow the assembly of the Haemolysin A T1SS and the plasmid encoding fusion proteins. pK184 HlyB,D has been previously described by Bakkes et al. (2010) JBC; 285(52):40573-80. Cells were grown in 2×YT medium supplemented with (30 μg/mL) and ampicillin (100 μg/mL) and 5 mM $CaCl_2$ overnight. 50 mL growth medium was inoculated with cells of a start OD600 of 0.1. Cells were grown at 37° C. and agitation and expression was induced with 1 mM IPTG at an OD600 of 0.4-0.6. After 2-6 h, cultures were centrifuged (20 min, 50.000×g, 4° C.) and supernatant samples (16 μL) and cells (ODeq=0.08) were analyzed by SDS-PAGE and Coomassie Brilliant Blue (CBB) staining.

19. Used Vector and Protein Sequences Encoded by the Used Vectors

The below DNA was cloned into the backbone of the pSU plasmid.

| Vector name | PeOI/PrOI | Wildtype protein accession no., version no., date | Construct | Vector sequence encoding SEQ ID NO: | Protein sequence/ SEQ ID NO: |
|---|---|---|---|---|---|
| pIAR_101 | peptide 101 | — | HlyA1-peptide 1 | 5 | 6 |
| pIAR_102 | peptide 102 | — | HlyA1-peptide 2 | 7 | 8 |
| pIAR_103 | peptide 103 | — | HlyA1-peptide 3 | 9 | 10 |
| pIAR_112 | peptide 103 | — | HlyA1R210D-peptide 3 | 11 | 12 |
| pIAR_115 | peptide 103 | — | HlyA1M88A-peptide 3 | 13 | 14 |
| pIAR_201 | Fuzeon ® | ACCESSION 3H00_A VERSION 3H00_A GI:281307071, VRL 19 DEC. 2009 | HlyA1-Fuzeon ® | 15 | 16 |
| pIAR_202 | human corticotropin release factor | ACCESSION AAX18228 VERSION AXX18228.1 GI:6978827, ROD 14 AUG. 2011 | HlyA1-HCRF | 17 | 18 |
| pIAR_207 | IFABP | ACCESSION NP_037200 VERSION NP_37200.1 GI:125973, BCT 03 MAY 2011 | HlyA1-IFABP | 19 | 20 |
| pIAR_212 | beta-amyloid peptide precursor [homo sapiens], 40 amino acids | ACCESSION ABB26265 VERSION ABB26265.2 GI:8176534, 14 JUL. 2000 | HlyA1-Mab40 | 21 | 22 |
| pIAR_213 | MBP | — | HlyA1-MBP | 23 | 24 |
| pIAR_214 | nisin | ACCESSION P13068 VERSION P13068.1 GI:125973, BCT 03 MAY 2011 | HlyA1-nisin | 25 | 26 |
| pIAR_215 | nisin | " | HlyA1-nisin (3 GG repeats) | 27 | 28 |
| pIAR_220 | nisin | " | HlyA1-nisin (2 GG repeats) | 29 | 30 |
| pIAR_221 | nisin | " | HlyA1-nisin (1 GG repeat) | 31 | 32 |
| pIAR_222 | nisin | " | HlyA1-nisin (no GG repeat) | 33 | 34 |
| pIAR_223 | nisin | " | HlyA1-nisin (4 GG repeats without the C-terminal part of HlyA1) | 35 | 36 |
| pIAR_227 | salmon calcitonin | ACCESSION BAA00281 VERSION BAA00281.1 GI:220946, SYN 21 MAY 2003 | HlyA1-Met-salmon calcitonin | | 65 |
| pIAR_228 | human calcitonin | ACCESSION ACB 14881 VERSION ACB14881.1 GI:170320110, SYN 24 MAR. 2008 | HlyA1-Tyr-human calcitonin | | 60 |
| pIAR_229 | beta-amyloid peptide precursor [homo sapiens], 42 amino acids | ACCESSION AAB26265 VERSION AAB26265.2 GI:8176534, 14 JUL. 2000 | HlyA1-Tyr-Mab42 | | 64 |

-continued

| Vector name | PeOI/PrOI | Wildtype protein accession no., version no., date | Construct | Vector sequence encoding SEQ ID NO: | Protein sequence/ SEQ ID NO: |
|---|---|---|---|---|---|
| pIAR_237 | Inhibitor Peptide 1 | Q06455 (MTG8_HUMAN) | HlyA1-Met-Inhibitor Peptide 1 | | 62 |
| pIAR_238 | | artificial sequence | HlyA1-Try-peptide 238 | | 53 |
| pIAR_239 | | artificial sequence | HlyA1-Try-peptide 239 | | 54 |
| pIAR_240 | | artificial sequence | HlyA1-Try-peptide 240 | | 55 |
| pIAR_241 | | artificial sequence | HlyA1-Try-peptide 241 | | 56 |
| pIAR_242 | | artificial sequence | peptide 240 | | 55 |
| pIAR_243 | | artificial sequence | peptide 241 | | 56 |
| pIAR_302 | nisin | ACCESSION P13068 VERSION P13068.1 GI:125973, BCT 03 MAY 2011 " | LipA-nisin | 37 | 38 |

Example 1

Figure 2:
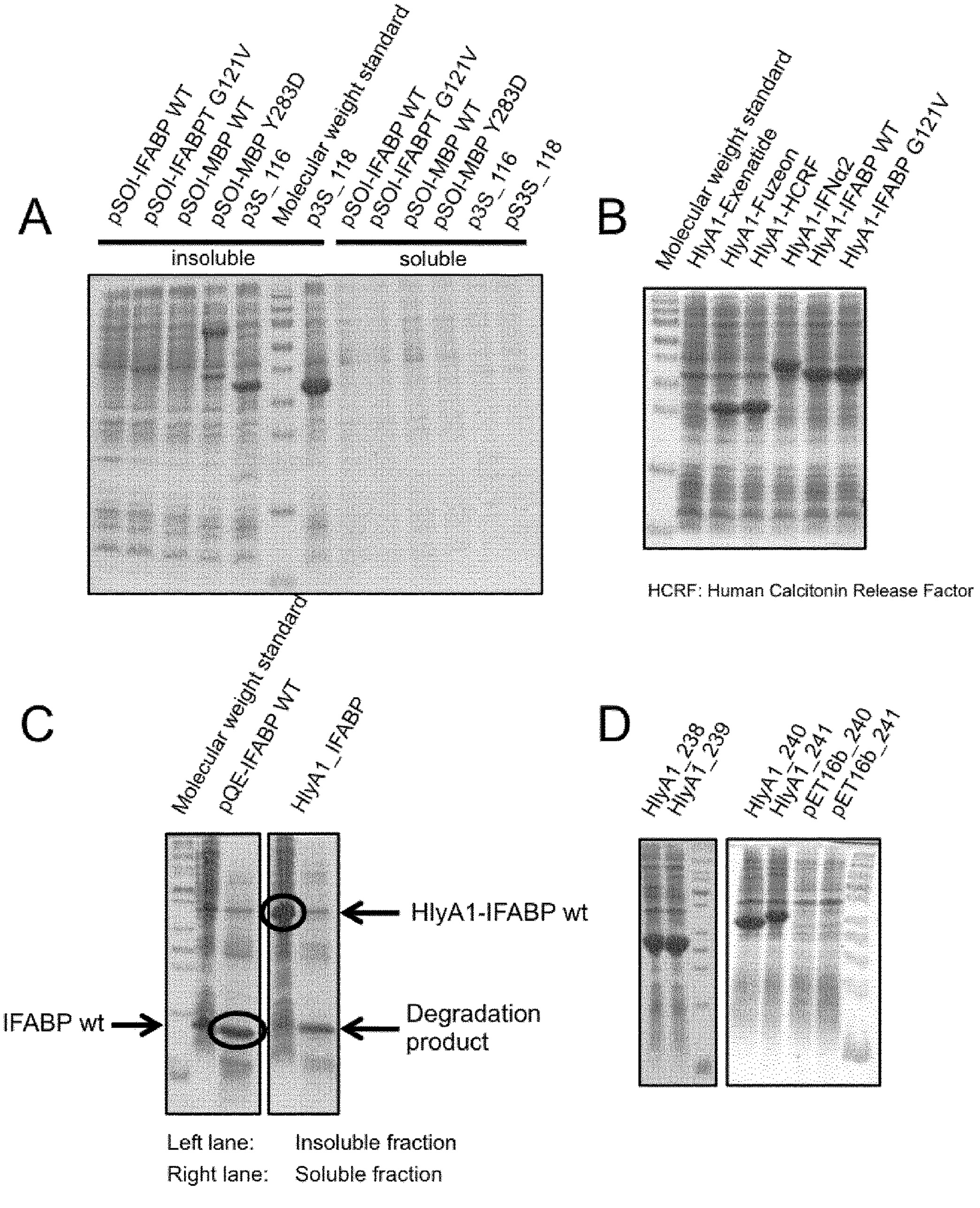
FIG. 2 shows a SDS-PAGE gel (15%) of insoluble and the soluble fractions of cell lysates of IFABP and MBP (and the indicated mutations thereof) fused to the N-terminus of HlyA1/HlyAc (FIG. 2A). Samples were loaded on a SDS-PAGE and stained with Coomassie Brilliant Blue (CBB).

Formation of IBs of PeOI or PrOI that are N-Terminally or C-Terminally Fused to HlyA or Fragments Thereof All indicated PrOI and PeOI fused N-terminal to HlyA or fragments of HlyA (for instance HlyA1, see FIG. 1 for a scheme of some constructs) aggregate in the cells as IBs (FIG. 2). Remarkably, unconjugated IFABP is normally soluble inside cells (see FIG. 2C). These results indicate that HlyA and fragments of HlyA induce the formation of IBs and transfer this characteristic to fused peptides and proteins.

PrOI or PeOI fused C-terminal to HlyA or fragments of HlyA (for instance HlyA1, see FIG. 1 for a schematic view of the constructs) were expressed in *E. coli* (FIG. 2B) and are insoluble inside cells (see exemplary HlyA1-IFABP, FIG. 2C). Thus, HlyA and fragments of HlyA force the aggregation as IBs of PrOI and PeOI fused to its N- and C-terminus.

Fusion proteins of HlyA or fragments thereof and peptide oligomers consisting of two, three, four, five, six, seven, eight, nine, ten or more monomers of one peptide or different peptides are also expressed as insoluble aggregated inside the cells. FIG. 2D shows the expression of peptide 238 (SEQ ID NO: 53) as monomer, trimer (peptide 240 [SEQ ID NO:55]) and pentamer (peptide241 [SEQ ID NO:56]) fused to HlyA1. Without the fusion to HlyA1, the trimeric and pentameric peptides were not produced by the cells (see pET16b_240 and pET16b_241). The oligomeric peptides are either not expressed inside the cells or proteolytically degraded.

Similar expression data were obtained for the following peptides fused to HlyA1: Mab40 (SEQ ID NO:63), Mab42 (SEQ ID NO:64), salmon Calcitonin (SEQ ID NO:65), human Calcitonin (SEQ ID NO:60), inhibitor peptid 1 (SEQ ID NO:62) and others.

Example 2

Purification and Refolding of HlyA and HlyA1

Figure 3:
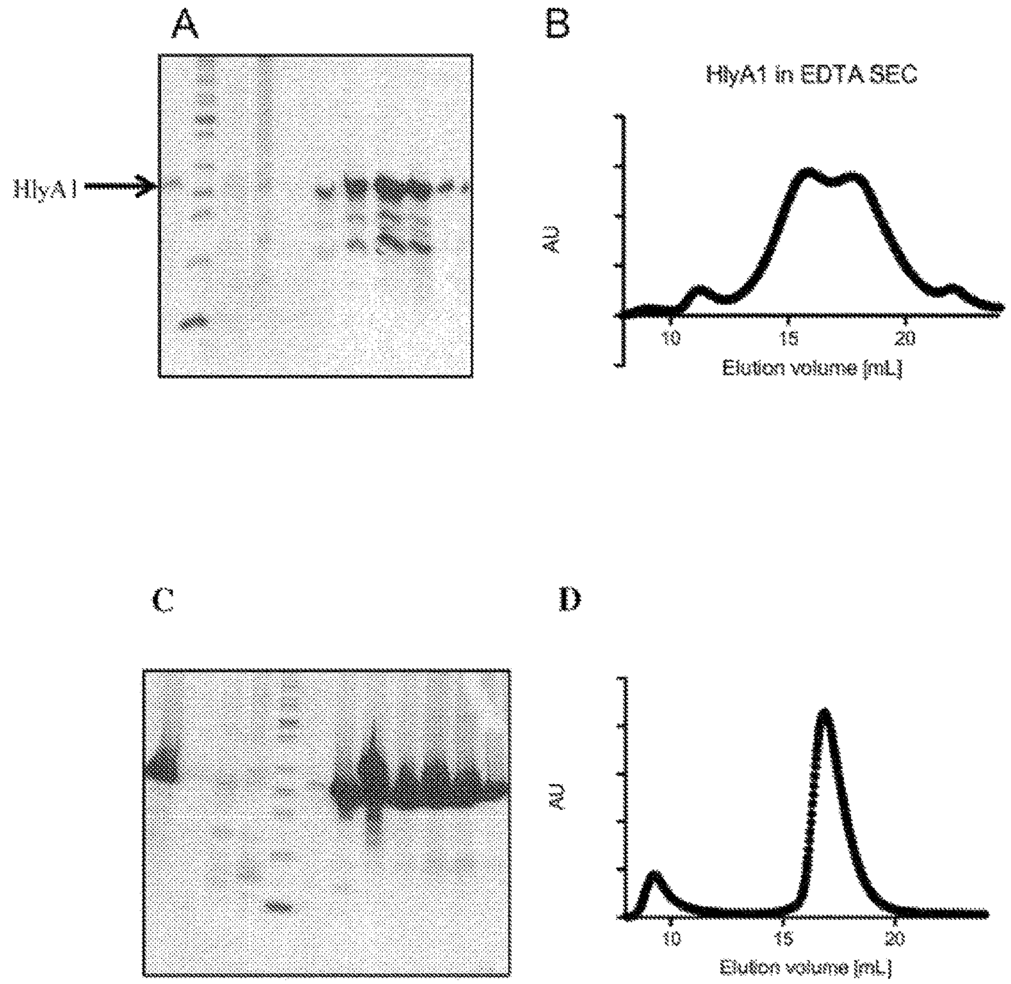
FIG. 3 shows experiments of HlyA1 being refolded in the presence of EDTA or $Ca^{2+}$ and applied to an IMAC and SEC. A: In the presence of $Ca^{2+}$, HlyA1, carrying an N-terminal His6-tag, was loaded to the IMAC (left lane) and bound proteins were eluted with an imidazole gradient. B: SEC analysis (Superdex 75 10/300 column, GE Healthcare) of HlyA1 eluted from the IMAC. C & D: HlyA1 was analyzed by IMAC and SEC in the presence of EDTA.

HlyA and HlyA1 were produced in *E. coli* as IBs. The IBs were refolded in the presence of EDTA or $CaCl_2$, respectively. Refolding efficiencies were about 35% with EDTA and inhomogeneous, instable HlyA or HlyA1 were obtained. FIGS. 3A and B show results for the HlyA fragment HlyA1. In contrast, over 90% of HlyA or HlyA1 were refolded in the presence of $Ca^{2+}$ and proteins were stable and homogeneous (FIGS. 3C and D).

Example 3

Purification and Refolding of HlyA1-Nisin

Figure 4:
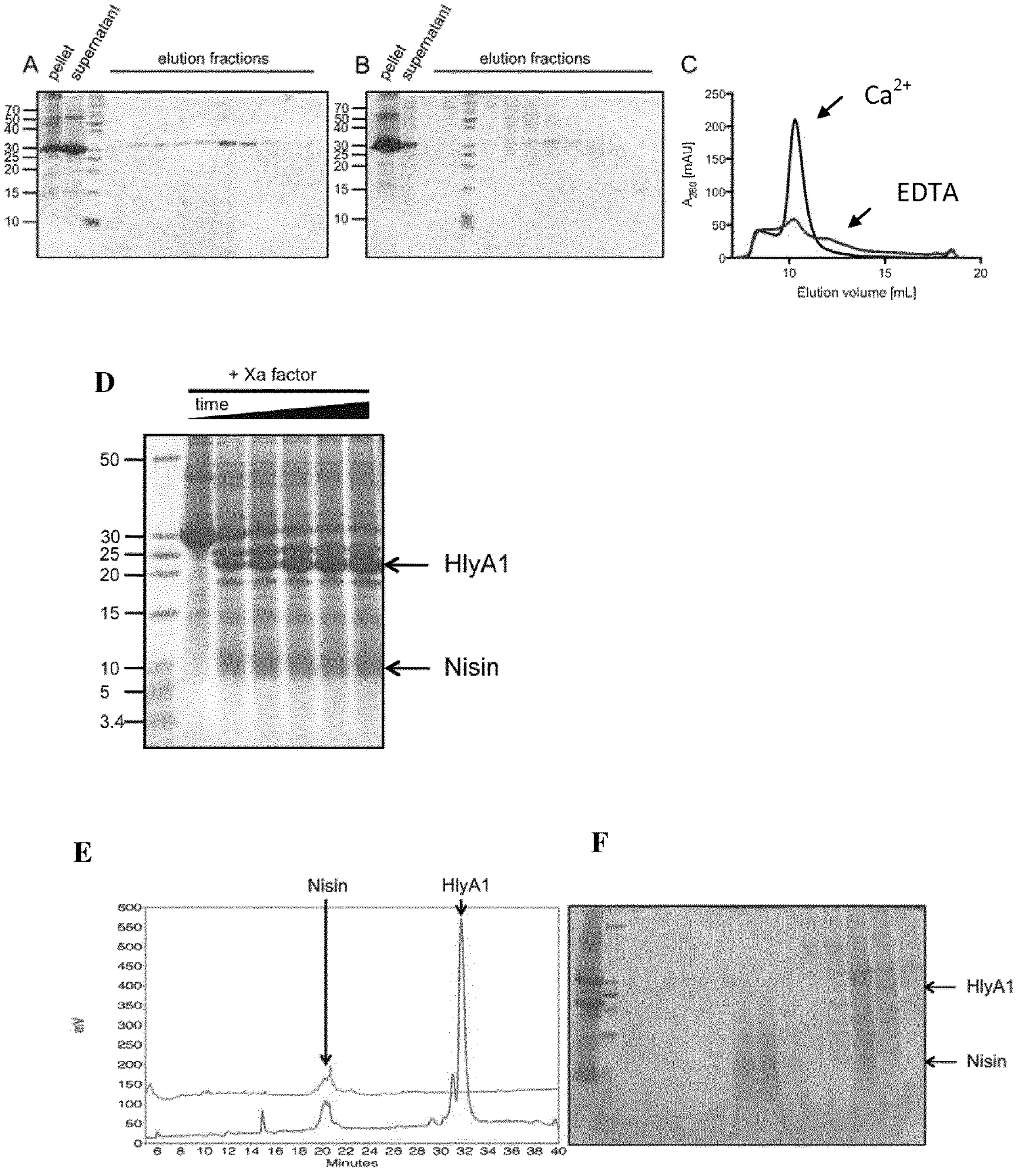
FIG. 4 shows experiments of HlyA1-Nisin being refolded either in the presence of $Ca^{2+}$ or EDTA, concentrated and applied to a SEC. A: Insoluble ("pellet") and soluble ("supernatant") fraction of HlyA1-Nisin after refolding in the presence of $Ca^{2+}$ and elution fractions of SEC analysis. B: Insoluble ("pellet") and soluble ("supernatant") fraction of HlyA1-Nisin after refolding in the presence of EDTA and elution fractions of SEC analysis. C: SEC chromatograms of A and B. D: HlyA1-Nisin was incubated with Factor Xa (NEB), samples of the mixture were taken at various time points (0, 20, 40, 60, 90, 120 min from left to right), loaded on a SDS-PAGE gel and stained with CBB. E: HPLC chromatograms of reference nisin (upper line) and nisin that was produced with the invented technology (lower line). F: SDS-PAGE analysis of HPLC elution fractions. Left lane: Factor Xa reaction after 90 min, other lanes: elution fractions of HPLC. Arrows indicate the positions of Nisin and HlyA1.

From 5 g cells expressing HlyA1-Nisin (encoded by plasmid pIAR_214), about 140 mg crude IBs of HlyA1-Nisin were prepared, denaturated and refolded. In the presence of EDTA, most protein was insoluble and aggregated and only low amounts of inhomogeneous HlyA1-Nisin were produced (FIGS. 4A and C). Refolding with $Ca^{2+}$, in contrast, produced a homogeneous protein species with high purity and in high yields (FIGS. 4B and C). The refolding efficiency was higher than 95% in the presence of $Ca^{2+}$ and below 25% in the presence EDTA.

Subsequent to refolding, Nisin was separated from HlyA1 by site-specific proteolysis with Factor Xa (FIG. 4D). After 90 min, 100 μL of the reaction mixture was purified by HPLC (FIG. 4E). Elution fractions were analyzed by SDS-PAGE analysis (FIG. 4F), Western Blotting and mass spectrometry (data not shown) and the complete Nisin molecule was identified.

Example 4

Purification and Refolding of LipA1-Nisin

Figure 5:
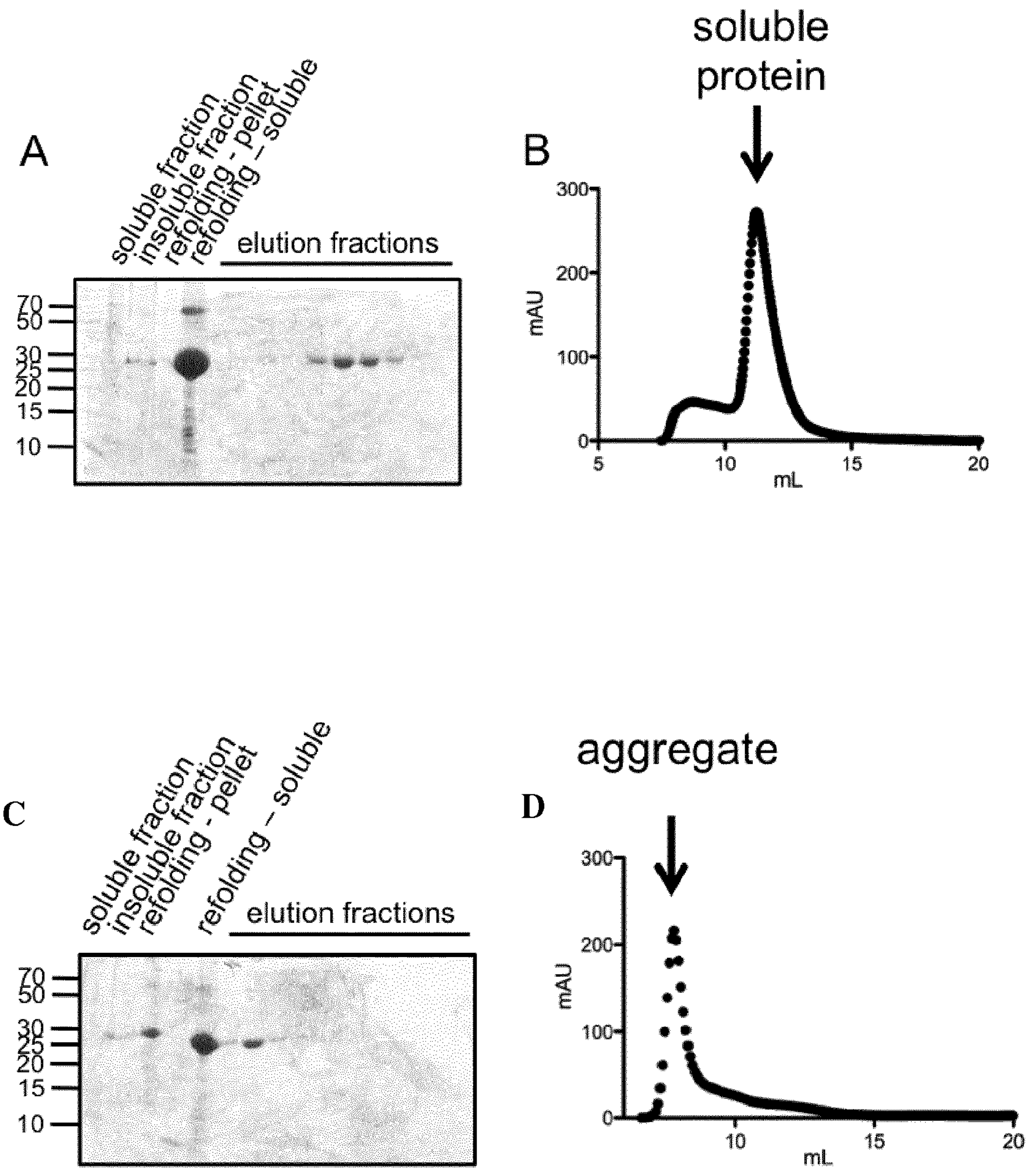
FIG. 5 shows refolding experiments of LipA1-Nisin in the presence of $Ca^{2+}$ and EDTA. LipA1-Nisin was produced as IBs in *E. coli* and isolated IBs were refolded in the presence of $Ca^{2+}$ or EDTA. In the presence of $Ca^{2+}$, pure and soluble LipA1-Nisin was produced in a homogeneous state. In contrast, LipA1-Nisin was aggregated in the presence of EDTA. A and B: SDS-PAGE analysis of SEC elution fractions and the corresponding SEC chromatogram of LipA1-

Lipase A (LipA) is another RTX protein that is secreted by a dedicated T1SS. Comparable construct to HlyA1-Nisin were cloned wherein Nisin is fused to a C-terminal fragment of LipA. This fragment covered the RTX domain and the secretion signal of LipA (encoded on plasmid pIAR_302). Subsequently, LipA1-Nisin was produced in *E. coli* and the formation of IBs was examined. As shown in FIG. 5A, LipA1-Nisin forms IBs. Moreover, refolding of denaturated LipA1-Nisin was analyzed in the presence of $Ca^{2+}$ and EDTA, respectively. SEC analyses of refolded LipA1-Nisin demonstrate that the fusion protein behaves similar to HlyA1-Nisin and that $Ca^{2+}$ induces refolding of LipA1-Nisin into a stable, homogeneous protein (FIG. 5B). In the presence of EDTA, in contrast, LipA1-Nisin is refolded less efficient and the majority of LipA1-Nisin forms aggregates (FIGS. 5C and D). Therefore, HlyA, LipA and likely other members of the RTX protein superfamily might be used to produce PrOI and PeOI as IBs and to refold fusion proteins by the addition of $Ca^{2+}$, other metal ions or specific refolding conditions.

Example 5

Analysis of Different HlyA Fragments and their Integrity to Induce Refolding

HlyA1-Nisin was truncated stepwise by GG repeats from the N-terminus (FIG. 1) to investigate the influence of each GG repeat for the formation of IBs and the refolding. Proteins expressed from the plasmids pIAR_215, pIAR_220, pIAR_221, pIAR_222 were investigated. To examine the influence of the C-terminal part of HlyA1, pIAR_223 was designed. pIAR_223 corresponds to Nisin fused C-terminal to all 4 GG repeats of HlyA1 lacking the C-terminus of HlyA1 (which includes the secretion signal).

Only the protein expressed from plasmid pIAR_222 was expressed in *E. coli* in amounts that were visible in cell lysate samples (FIG. 6A). Nevertheless, IBs of cells expressing proteins encoded by pIAR_215, pIAR_220-223 could be prepared, denatured and refolded with either $Ca^{2+}$ or EDTA. Refolded proteins were concentrated and analyzed by SEC. The cleavage of concentrated proteins with Factor Xa was analyzed. Only plasmids pIAR_220, pIAR_222 and pIAR_223 produced recombinant protein in significant amounts. Therefore, these proteins are considered for the following interpretations.

IBs of proteins encoded from plasmid pIAR_220 (two GG repeats), pIAR_222 (no GG repeat) and pIAR_223 (only four GG repeats, no C-terminal part of HlyA1) were produced. Therefore, the GG repeats and the C-terminal portion of HlyA1 consisting of the secretion signal are potent to induce the formation of IBs.

The protein encoded by pIAR_220 (two GG repeats) was refolded and concentrated more efficient in the presence of $Ca^{2+}$ compared to EDTA (FIGS. 6B and C), whereas the refolding and concentration was comparable efficient for the protein encoded by pIAR_222 (no GG repeat) with both, $Ca^{2+}$ and EDTA. Thus, two GG repeats allow increasing the refolding efficiency in a $Ca^{2+}$-dependent manner. SEC analysis of proteins encoded by pIAR_220 and pIAR_222 supported these results. The protein encoded by pIAR_220 showed a distinct and symmetric signal by SEC analysis only in the presence of $Ca^{2+}$ (FIG. 6C), whereas the chromatograms of SEC analysis with the protein encoded by pIAR_222 are comparable in the presence of EDTA and $Ca^{2+}$ (FIGS. 6D and E) and the protein encoded by pIAR_222 thus did not fold into a soluble, homogenous state. This demonstrates that the GG repeats are essential for the efficient renaturation.

The protein encoded by pIAR_223 (4 GG repeats without the C-terminal part of HlyA1) elutes as a symmetric signal from the SEC only in the presence of $Ca^{2+}$. In contrast, in the presence of EDTA the recombinant protein expressed from pIAR_223 is non-homogenous (FIGS. 6F and G).

Example 6

Purification and Refolding of HlyA1-HCRF

Out of about 5 g cells, about 200 mg crude IBs were purified for HlyA1-HCRF (encoded by plasmid pIAR_202) that were denatured in guanidinium-hydrochlorid and subsequently refolded (FIG. 7A). The refolding of 40 mg HlyA1-HCRF in the presence of EDTA produced about 8.4 mg soluble protein, however, the protein sample was instable and inhomogenous (FIGS. 7C and E). In contrast, refolding in the presence of $Ca^{2+}$ yielded 34 mg soluble and homogeneous protein (corresponding to a refolding rate of about 85%) (FIGS. 7C and D).

Refolded HlyA1-HCRF was digested with Factor Xa (FIG. 7G) and the reaction mixture was purified by HPLC (FIG. 7F). With this strategy, HCRF was cleaved off and separated from HlyA1.

Example 7

Production of IFABP

HlyA1-IFABP (encoded on plasmid pIAR_207) was expressed and from about 6 g cells, 205 mg denatured IBs were prepared. HlyA1-IFABP was refolded (>65%) in the presence of $Ca^{2+}$ and EDTA into a stable, homogenous state (FIG. 8A-D). Despite forcing the aggregation of IFABP into IBs, HlyA1 does not disturb refolding of denaturated IFABP in vitro. With this strategy HlyA1-IFABP was produced in high yields, high purity and a soluble form. Based on SEC analysis, the positive effect of $Ca^{2+}$ was negligible for the renaturation of HlyA1-IFABP, however, the biological activity of HlyA1-IFABP is higher in the presence of $Ca^{2+}$ (FIGS. 8F and G). Therefore, in some embodiments allocrites of T1SS or fragments thereof function as IB-tags and do not interfere with the efficient renaturation of fused PeOI or PrOI. The presence of $Ca^{2+}$ ions increases the bio-activity of the fusion partner, for example, by increasing its stability and solubility by increasing the stability and/or stability of the allocrites or fragments thereof.

IFABP was cleaved from HlyA1 with Factor Xa. 1 µg Factor Xa digested >95% of 50 µg HlyA1-IFABP in 3 h at 20° C. (FIG. 8E). The biological activity of HlyA1-IFABP was examined with 11-(((5-(dimethylamino)-1-naphthalenyl)sulfonyl)amino)-undecanoic acid (DAUDA), a fluorescent fatty acid analogon (FIGS. 8F and G). The $K_D$ for HlyA1-IFABP refolded in $Ca^{2+}$ and EDTA were determined to be 140.8 nM±13.1 nM and 264.3 nM±13.2 nM, respectively. HlyA1-IFABP is biological active demonstrating that the developed technology allows production of active, soluble protein. The activity is comparable to values in the literature for IFABP ($K_D$=20.9 nM±0.6 nM).

Example 8

Production of IFNA2

HlyA1-IFNA2 (encoded by plasmid pIAR_210) was expressed in high levels in *E. coli*. 310 mg denatured IBs were purified from about 5 g cells. Refolding of HlyA1-IFNA2 was performed in the presence of $Ca^{2+}$ or EDTA. ±3-4% of HlyA1-IFNA2 was refolded in the presence of both reagents. SDS-PAGE analyses with or without a reducing reagent (DTT) suggested an oxidized state of HlyA1-IFNA2 after refolding and therefore the formation of disulfide bonds (data not shown). Refolding efficiency was increased to nearly 100% by the addition of 0.5 M arginine. Again, HlyA1 does not interfere with the refolding of IFNA2, and IFNA2 was produced in high yields with the presented invention. Refolded HlyA1-IFNA2 was oxidized as demonstrated by SDS-PAGE analysis in the presence and absence of DTT (FIG. 9A) and biological active (data not shown).

HlyA1-IFNA2 refolded in the presence of arginine and $Ca^{2+}$ was soluble and homogeneous (FIG. 9B). In contrast, two elution signals were observed for HlyA1-IFNA2 refolded with arginine and EDTA (FIG. 9C). Therefore, refolding in the presence of $Ca^{2+}$ increased the homogeneity of HlyA1-IFNA2 compared to refolding in the presence of EDTA.

Example 9

Production of MBP

MBP is well known as solubility-tag for the soluble expression of fused PrOI within *E. coli* (Nallamsetty, S. & Waugh, D. S. A. (2007) Nat Protoc, 2, 383-391). Nevertheless, HlyA1 forces the aggregation of MBP as IBs and HlyA1-MBP IBs (encoded by plasmid pIAR_213) were prepared (FIG. 10). HlyA1-MBP was refolded and concentrated in the presence of $Ca^{2+}$. SEC analysis demonstrated the production of soluble HlyA1-MBP (data not shown). Refolded HlyA1-MBP bound to immobilized amylose demonstrating the biological functionality of refolded MBP (FIG. 10).

Example 10 pIAR_101-103-Refolding and Factor Xa Digestion

Fusion proteins of HlyA1 and peptides 101, 102 and 103 (encoded by plasmids pIAR_101, pIAR_102 and pIAR_103) were expressed in *E. coli* as IBs (FIG. 11A). Out of about 4.5 g cells 72 mg, 92 mg and 108 mg crude IBs were prepared.

IBs were refolded with $Ca^{2+}$ to nearly 100% and proteins were concentrated (compare lanes "pellet" and "refolded peptide 10X", FIG. 11B-D). Fusion proteins were incubated with Factor Xa and the PeOI could be separated from HlyA1. Peptides were purified by HPLC. Peptide 103 was identified by mass spectrometry (data not shown).

Example 11

Purification and Refolding of HlyA1-Fuzeon®

Out of about 4 g cells 130 mg crude IBs of HlyA1-Fuzeon® (encoded by plasmid pIAR_201) were purified, which were denaturated in guanidinium-hydrochlorid and subsequently refolded. The refolding efficiency was ±30% with $Ca^{2+}$ and ±11% with EDTA. SEC analysis demonstrated that HlyA1-Fuzeon® could only be produced in a soluble state in the presence of $Ca^{2+}$ (FIGS. 12A and B). FIG. 12C shows the results of the proteolytic separation of Fuzeon® from HlyA1-Fuzeon® with Factor Xa.

Example 12

Degeneration of an Unspecific Cleavage Site for Factor Xa in HlyA1

Mass spectrometry identified an unspecific cleavage site for Factor Xa in HlyA1 (primary sequence SYGR, aa 207-210). The mutation of wild-type HlyA1 to HlyA1-R210D in plasmid pIAR_112 was constructed with the purpose to disrupt this cleavage site and to increase the cleavage efficiency of Factor Xa on intended cleavage sites between HlyA1 and the PeOI or PrOI. Factor Xa digestion of HlyA1-R210D fused to peptide 103 indicated that no site products of HlyA1-R210D were formed (FIG. 13).

Example 13

Chemical Cleavage of Fusion Proteins

Chemical cleavage of peptide bonds is well known in the literature. The applicability of such approach to separate PrOI or PeOI from the bifunctional tag was investigated. Cyanogen bromid (CNBr), a chemical reagent that cleaves peptide bonds C-terminal to methionine residues, and BNPS-skatole, NCS and TFA, chemical reagents that cleave peptide bonds C-terminal to tryptophane residues, were chosen. The single methionine and tryptophane residues within HlyA1 were mutated to alanine (M88A, W109A) and a methionine or tryptophane was placed N-terminal to the PeOI or PrOI. For example, a methionine was added N-terminal to peptide 103 (protein HlyA1 M88A-Met-Peptide 3, encoded on plasmid pIAR_115). As shown by the SDS-PAGE analysis in FIG. 14, the peptides were successfully cleaved off from HlyA1. A: Peptide 103 was separated from HlyA1 M88A-Met by CNBr. The identity of peptide 103 was confirmed by mass spectrometry (data not shown). B: About 50% of the peptides encoded by pIAR_202 w, pIAR_238, pIAR_239, pIAR_240 and pIAR_241 were cleaved off from HlyA1 by NCS in 3 h. pIAR_240 and pIAR_241 are clearly visible on the coomassie-stained gel (indicated by the arrow), whereas the other peptides were too small to be stained. The species visible at above 50 kDa in the 0 h sample corresponds to the cysteine-bridged dimer of the peptides.

Example 14

HlyA1 Fusion Proteins Expressed Via Fermentation

*E. coli* carrying plasmid pIAR_115 was used for fermentation. When glucose was used as feed during fermentation the expression was repressed. This repression might result from a repression of the lac promoter that regulates the expression of plasmid pIAR_115 by glucose. Therefore, glycerol was tested as feed during fermentation. With this strategy, more than 2.5 kg wet cells were produced from 10 L fermentation broth. Expression levels of HlyA1 M88A-Met-peptide 3 were comparable or even increased to batch cultures (FIG. 15). Out of 440 g cells (wet cell mass), 65 g IBs were prepared. Therefore, the invented technology is up-scalable and titers of IBs are increased by increasing the cell mass and/or the expression levels.

All documents cited herein, are hereby incorporated by reference in their entirety.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A method for production of a recombinant peptide (PeOI) or protein of interest (PrOI), wherein the method comprises:

(a) introducing a nucleic acid molecule encoding a fusion protein comprising at least one PeOI or PrOI, and at least one allocrite of a type 1 secretion system (TISS) or a fragment thereof, into a host cell, wherein the host cell does not express one or more of a heterologous ATP-binding cassette (ABC) transporter of the TISS, a heterologous membrane fusion protein (MFP) of the TISS, and a heterologous outer membrane protein (OMP) of the TISS, and wherein the allocrite of the T1 SS or fragment thereof (i) comprises at least one GG repeat of a consensus sequence that comprises the amino acid sequence set forth in SEQ ID NO:67, (ii) causes expression of the fusion protein in an insoluble, denatured form of inclusion bodies (IB), and (iii) promotes refolding of the insoluble, denatured form of the fusion protein when the fusion protein is contacted with a refolding buffer that comprises at least 0.01 mM of an earth alkaline metal ion;

(b) cultivating the host cell under conditions that allow expression of the fusion protein, wherein the fusion protein is expressed in the insoluble, denatured form of inclusion bodies (IB);

(c) isolating the inclusion bodies (IB) of step (b) from said host cells;

(d) isolating the insoluble, denatured form of the fusion protein from said IB of step (c); and (e) subjecting the insoluble, denatured form of the fusion protein isolated in step (d) to conditions that allow the PeOI or PrOI to refold into a soluble, functional three-dimensional conformation, by contacting the fusion protein with said refolding buffer that comprises at least 0.01 mM of an earth alkaline metal ion.

2. The method according to claim 1, wherein the allocrite of a TISS is selected from the group consisting of HlyA, CyaA, EhxA, LktA, PlLktA, PasA, PvxA, MmxA, LtxA, ApxIA, ApxIIA, ApxIIIA, ApxIVA, Apxl, ApxII, AqxA, VcRtxA, VvRtxA, MbxA, RTX cytotoxin, RtxL1, RtxL2, FrhA, LipA, TliA, PrtA, PrtSM, PrtG, PrtB, PrtC, Apr A, AprX, ZapA, ZapE, Sap, HasA, colicin V, LapA, ORF, RzcA, RtxA, XF2407, XF2759, RzcA, RsaA, Crs, CsxA, CsxB, SlaA, SwmA, S111951, NodO, PlyA, PlyB, FrpA, FrpC.

3. The method of claim 1, wherein the allocrite of a TISS is HlyA comprising the amino acid sequence as set forth in SEQ ID NO:2, a fragment thereof or a polypeptide that has at least 80% sequence identity to the amino acid sequence of SEQ ID NO:2 or the fragment thereof.

4. The method according to claim 3, wherein the fragment of HlyA consists of the amino acid sequence as set forth in SEQ ID NO:4 or a polypeptide that has at least 80% sequence identity to the amino acid sequence of SEQ ID NO:4.

5. The method of claim 1, wherein the host cell is cultivated in an expression medium that comprises 20.0 mM or less of $Ca^{2+}$.

6. The method of claim 1, wherein expression by the host cell of an endogenous ABC transporter gene of the T1SS or activity of a product of the ABC tranporter gene is inhibited or transport is inefficient, wherein expression by the host cell of an endogenous MFP gene of the T1SS or activity of a product of the MFP gene is inhibited or transport is inefficient, and/or wherein expression by the host cell of an endogenous OMP gene of the T1SS or activity of a product of the MFP gene is inhibited or transport is inefficient.

7. The method according to claim 6, wherein the host cell does not express endogenous ABC transporter, endogenous MFP and/or endogenous OMP of the T1SS.

8. The method of claim 1, wherein in step (e) the fusion protein is exposed to a refolding buffer, wherein the refolding buffer comprises at least 0.01 mM of $Ca^{2+}$.

9. The method of claim 1, wherein one or more of:

(I) the host cell is a prokaryotic cell;

(II) the expression of the fusion protein is performed in minimal culture medium;

(III) the fusion protein is purified using a method selected from affinity chromatography, ion exchange chromatography, reverse phase chromatography, size exclusion chromatography, and combinations thereof;

(IV) the method comprises the additional step (e) of contacting the fusion protein with a protease suitable for cleavage of the fusion protein to yield the allocrite and the peptide or PrOI as separate molecules;

(V) the method comprises the additional step (e) of cleaving the fusion protein by chemical treatment to yield the allocrite and the PeOI or PrOI as separate molecules; or (VI) the method comprises a step (e) as defined in (IV) or (V) followed by purification of the PeOI or PrOI.

10. The method according to claim 1, wherein the at least one PeOI or PrOI is selected from the group consisting of Nisin having the amino acid sequence set forth in one of SEQ ID NOS: 26, 28, 30, 32, 34, 36 or 38, human corticotropin-releasing factor (HCRF) having the amino acid sequence set forth in SEQ ID NO: 18, intestinal fatty acid-binding protein (IFABP) having the amino acid sequence set forth in SEQ ID NO: 20, interferon alpha 2(IFNA2), maltose binding protein (MBP) having the amino acid sequence set forth in SEQ ID NO: 24, peptide 101 having the amino acid sequence set forth in SEQ ID NO: 6, peptide 102 having the amino acid sequence set forth in SEQ ID NO: 8, peptide 103 having the amino acid sequence set forth in SEQ ID NO: 10, M-beta amyloid 40 (MAB-40), Mab-42 having the amino acid sequence set forth in SEQ ID NO: 64, enfuvirtide having the amino acid sequence set forth in SEQ ID NO: 16, salmon calcitonin having the amino acid sequence set forth in SEQ ID NO: 65, human calcitonin having the amino acid sequence set forth in SEQ ID NO: 60, inhibitor peptide 1 having the amino acid sequence set forth in SEQ ID NO: 62, inhibitor peptide 238 having the amino acid sequence set forth in SEQ ID NO: 53, inhibitor peptide 239 having the amino acid sequence set forth in SEQ ID NO: 54, inhibitor peptide 240 having the amino acid sequence set forth in SEQ ID NO: 55, and inhibitor peptide 241 having the amino acid sequence set forth in SEQ ID NO: 56.

11. The method according to claim 1, wherein the nucleic acid molecule encoding the fusion protein further comprises a regulatory nucleotide sequence that modulates expression of the fusion protein.

12. A method for production of a recombinant peptide (PeOI) or protein of interest (PrOI), wherein the method comprises:

(a) introducing a nucleic acid molecule encoding a fusion protein comprising at least one PeOI or PrOI, and at least one allocrite of a type 1 secretion system (TISS) or a fragment thereof, into a host cell, wherein the host cell does not express a heterologous ATP-binding cassette (ABC) transporter of the TISS, a heterologous membrane fusion protein (MFP) of the TISS, and a heterologous outer membrane protein (OMP) of the TISS, and wherein the allocrite of the T1SS or fragment thereof (i) comprises at least one GG repeat of a consensus sequence that comprises the amino acid sequence set forth in SEQ ID NO:67, (ii) causes expression of the fusion protein in an insoluble, denatured form of inclusion bodies (IB), and (iii) promotes refolding of the insoluble, denatured form of the fusion protein when the fusion protein is contacted with a refolding buffer that comprises at least 0.01 mM of an earth alkaline metal ion;

(b) cultivating the host cell under conditions that allow expression of the fusion protein, wherein the fusion protein is expressed in the insoluble, denatured form of inclusion bodies (IB);

(c) isolating the inclusion bodies (IB) of step (b) from said host cells; and (d) isolating the insoluble, denatured form of the fusion protein from said IB of step (c); and (e) subjecting the insoluble, denatured form of the fusion protein isolated in step (d) to conditions that allow the PeOI or PrOI to refold into a functional three-dimensional conformation, by contacting the fusion protein with said refolding buffer that comprises at least 0.01 mM of an earth alkaline metal ion.

13. The method of claim 1 wherein the earth alkali metal ion is selected from the group consisting of $Ca^{2+}$, $Sr^{2+}$, and $Ba^{2+}$.

14. The method of claim 12 wherein the earth alkali metal ion is selected from the group consisting of $Ca^{2+}$, $Sr^{2+}$, and $Ba^{2+}$.

* * * * *

SEQUENCE LISTING

<160> NUMBER OF SEQ ID NOS: 68

<210> SEQ ID NO 1
<211> LENGTH: 3075
<212> TYPE: DNA
<213> ORGANISM: Escherichia coli

<400> SEQUENCE: 1

```
atgacaacaa taaccactgc acaaattaaa agcacactgc agtctgcaaa gcaatccgct      60
gcaaataaat tgcactcagc aggacaaagc acgaaagatg cattaaaaaa agcagcagag     120
caaacccgca atgcgggaaa cagactcatt ttacttatcc ctaaagatta taaaggacag     180
ggttcaagcc ttaatgacct tgtcaggacg gcagatgaac tgggaattga agtccagtat     240
gatgaaaaga atggcacggc gattactaaa caggtgttcg gcacagcaga gaaactcatt     300
ggcctcaccg aacggggagt gactatcttt gcaccacaat tagacaaatt actgcaaaag     360
tatcaaaaag caggtaatat attaggtggc ggtgctgaaa atatcggtga taacttagga     420
aaggcaggcg gtatattgtc aacgtttcaa aatttcctgg gtactgcact ttcctcaatg     480
aaaatagacg aactgataaa gaaacaaaaa tctggtggca atgtcagttc ttctgagatg     540
gcagaagcga gtattgagct aatcaatcaa cttgtggata cagttgccag ccttaataat     600
aatgttaact cattttctca acaactcaat actctgggaa gtgtattatc caatacaaag     660
cacctgaacg gtgttggtaa taagttacag aatttaccta atcttgataa tatcggtgca     720
gggttagata ctgtatcggg tattttatct gcgatttcag caagcttcat tctgagcaat     780
gcagatgcag ataccagaac taaagctgca gcaggtgttg aattaacaac gaaagtactg     840
ggtaatgttg gaaaaggtat ttctcaatat attatcgcac agcgcgctgc acaggggtta     900
tctacatctg ctgctgctgc cggtttaatt gcttctgctg tgacactagc aattagtccc     960
ctctcattcc tgtccattgc cgataagttt aaacgtgcca ataaaataga ggagtattca    1020
caacgattca aaaaacttgg atacgatggt gacagtttac ttgctgcttt ccacaaagaa    1080
acaggggcta ttgatgcatc attaacaacg ataagcactg tactggcttc agtatcttca    1140
ggtattagtg ctgctgcaac gacatctctg gttggtgcac cggtaagcgc gctggtaggc    1200
gctgttacgg ggataatttc aggtatcctt gaggcttcaa agcaggcaat gtttgaacat    1260
gttgccagta aaatggctga tgttattgct gaatgggaga aaaaacacgg caaaaattac    1320
tttgaaaatg gatatgatgc ccgccatgct gcatttttag aagataactt taaaatatta    1380
tctcagtata ataaagagta ttctgttgaa agatcagtcc tcattaccca gcaacattgg    1440
gatacgctga taggtgagtt agctggtgtc accagaaatg gagacaaaac actcagtggt    1500
aaaagttata ttgactatta tgaagaagga aaacgtctgg agaaaaaacc ggatgaattc    1560
cagaagcaag tctttgaccc attgaaagga aatattgacc tttctgacag caaatcttct    1620
acgttattga aatttgttac gccattatta actcccggtg aggaaattcg tgaaaggagg    1680
```

-continued

```
cagtccggaa aatatgaata tattaccgag ttattagtca agggtgttga taaatggacg   1740

gtgaaggggg ttcaggacaa gggggctgta tatgattact ctaacctgat tcagcatgca   1800

tcagtcggta ataaccagta tcgggaaatc cgtattgagt cacacctggg agacggggat   1860

gataaggtct ttttatctgc cggctcagcc aatatctacg caggtaaagg acatgatgtt   1920

gtttattatg ataaaacaga cactggttat ctgaccattg atggcacaaa agcaaccgaa   1980

gcgggtaatt acacggtaac acgtgtactt ggtggcgatg ttaaggtttt acaggaagtt   2040

gtgaaggagc aggaggtttc agtcggaaaa agaactgaaa aaacgcaata tcggagttat   2100

gaattcactc atatcaatgg taaaaattta acagagactg ataacttata ttccgtggaa   2160

gaacttattg ggaccacgcg tgccgacaag ttttttggca gtaaatttac tgatatcttc   2220

catggcgcgg atggtgatga ccttatagaa ggaaatgatg ggaatgaccg cttatatggt   2280

gataaaggta atgacacact gagtggtgga aacggagatg accagctcta tggcggtgat   2340

ggtaacgata agttgattgg gggagcaggt aataattacc tgaacggcgg agatggagat   2400

gatgagcttc aggttcaggg aaattctctt gcaaaaaatg tattattcgg tggaaaaggt   2460

aatgacaagc tgtacggcag tgagggggca gatctgcttg atggtggaga gggggatgat   2520

ctcctgaaag gcggatatgg taatgatatt tatcgttatc tgtcaggata tggtcatcat   2580

attattgatg atgatggggg gaaagaggat aaactcagtt tggctgatat tgatttccgg   2640

gatgtggcct tcaagcgaga aggtaatgac ctcatcatgt ataaagctga aggtaatgtt   2700

ctttccattg gtcataaaaa tggtattaca ttcaggaact ggtttgaaaa agagtcaggt   2760

gatatctcta atcaccagat agagcagatt tttgataaaa gtggccggat aatcacacct   2820

gattccctta aaaaggcact tgagtatcaa cagcgtaata ataaggcaag ttatgtgtat   2880

gggaatgatg cattagccta tggaagtcag ggtgatctta atccattaat taatgaaatc   2940

agcaaaatca tttcagctgc aggtagcttc gatgttaaag aggaaagaac tgcagcttct   3000

ttattgcagt tgtccggtaa tgccagtgat ttttcatatg gacggaactc aataaccctg   3060

accacatcag cataa                                                   3075
```

<210> SEQ ID NO 2
<211> LENGTH: 1024
<212> TYPE: PRT
<213> ORGANISM: Escherichia coli

<400> SEQUENCE: 2

```
Met Thr Thr Ile Thr Thr Ala Gln Ile Lys Ser Thr Leu Gln Ser Ala
1               5                   10                  15

Lys Gln Ser Ala Ala Asn Lys Leu His Ser Ala Gly Gln Ser Thr Lys
            20                  25                  30

Asp Ala Leu Lys Lys Ala Ala Glu Gln Thr Arg Asn Ala Gly Asn Arg
        35                  40                  45

Leu Ile Leu Leu Ile Pro Lys Asp Tyr Lys Gly Gln Gly Ser Ser Leu
    50                  55                  60

Asn Asp Leu Val Arg Thr Ala Asp Glu Leu Gly Ile Glu Val Gln Tyr
65                  70                  75                  80

Asp Glu Lys Asn Gly Thr Ala Ile Thr Lys Gln Val Phe Gly Thr Ala
                85                  90                  95

Glu Lys Leu Ile Gly Leu Thr Glu Arg Gly Val Thr Ile Phe Ala Pro
            100                 105                 110

Gln Leu Asp Lys Leu Leu Gln Lys Tyr Gln Lys Ala Gly Asn Ile Leu
```

-continued

```
        115                 120                 125

Gly Gly Gly Ala Glu Asn Ile Gly Asp Asn Leu Gly Lys Ala Gly Gly
    130                 135                 140

Ile Leu Ser Thr Phe Gln Asn Phe Leu Gly Thr Ala Leu Ser Ser Met
145                 150                 155                 160

Lys Ile Asp Glu Leu Ile Lys Lys Gln Lys Ser Gly Gly Asn Val Ser
                165                 170                 175

Ser Ser Glu Met Ala Glu Ala Ser Ile Glu Leu Ile Asn Gln Leu Val
            180                 185                 190

Asp Thr Val Ala Ser Leu Asn Asn Asn Val Asn Ser Phe Ser Gln Gln
        195                 200                 205

Leu Asn Thr Leu Gly Ser Val Leu Ser Asn Thr Lys His Leu Asn Gly
    210                 215                 220

Val Gly Asn Lys Leu Gln Asn Leu Pro Asn Leu Asp Asn Ile Gly Ala
225                 230                 235                 240

Gly Leu Asp Thr Val Ser Gly Ile Leu Ser Ala Ile Ser Ala Ser Phe
                245                 250                 255

Ile Leu Ser Asn Ala Asp Ala Asp Thr Arg Thr Lys Ala Ala Ala Gly
            260                 265                 270

Val Glu Leu Thr Thr Lys Val Leu Gly Asn Val Gly Lys Gly Ile Ser
        275                 280                 285

Gln Tyr Ile Ile Ala Gln Arg Ala Ala Gln Gly Leu Ser Thr Ser Ala
    290                 295                 300

Ala Ala Ala Gly Leu Ile Ala Ser Ala Val Thr Leu Ala Ile Ser Pro
305                 310                 315                 320

Leu Ser Phe Leu Ser Ile Ala Asp Lys Phe Lys Arg Ala Asn Lys Ile
                325                 330                 335

Glu Glu Tyr Ser Gln Arg Phe Lys Lys Leu Gly Tyr Asp Gly Asp Ser
            340                 345                 350

Leu Leu Ala Ala Phe His Lys Glu Thr Gly Ala Ile Asp Ala Ser Leu
        355                 360                 365

Thr Thr Ile Ser Thr Val Leu Ala Ser Val Ser Ser Gly Ile Ser Ala
    370                 375                 380

Ala Ala Thr Thr Ser Leu Val Gly Ala Pro Val Ser Ala Leu Val Gly
385                 390                 395                 400

Ala Val Thr Gly Ile Ile Ser Gly Ile Leu Glu Ala Ser Lys Gln Ala
                405                 410                 415

Met Phe Glu His Val Ala Ser Lys Met Ala Asp Val Ile Ala Glu Trp
            420                 425                 430

Glu Lys Lys His Gly Lys Asn Tyr Phe Glu Asn Gly Tyr Asp Ala Arg
        435                 440                 445

His Ala Ala Phe Leu Glu Asp Asn Phe Lys Ile Leu Ser Gln Tyr Asn
    450                 455                 460

Lys Glu Tyr Ser Val Glu Arg Ser Val Leu Ile Thr Gln Gln His Trp
465                 470                 475                 480

Asp Thr Leu Ile Gly Glu Leu Ala Gly Val Thr Arg Asn Gly Asp Lys
                485                 490                 495

Thr Leu Ser Gly Lys Ser Tyr Ile Asp Tyr Tyr Glu Glu Gly Lys Arg
            500                 505                 510

Leu Glu Lys Lys Pro Asp Glu Phe Gln Lys Gln Val Phe Asp Pro Leu
        515                 520                 525

Lys Gly Asn Ile Asp Leu Ser Asp Ser Lys Ser Ser Thr Leu Leu Lys
    530                 535                 540
```

-continued

```
Phe Val Thr Pro Leu Leu Thr Pro Gly Glu Glu Ile Arg Glu Arg Arg
545                 550                 555                 560

Gln Ser Gly Lys Tyr Glu Tyr Ile Thr Glu Leu Leu Val Lys Gly Val
                565                 570                 575

Asp Lys Trp Thr Val Lys Gly Val Gln Asp Lys Gly Ala Val Tyr Asp
            580                 585                 590

Tyr Ser Asn Leu Ile Gln His Ala Ser Val Gly Asn Asn Gln Tyr Arg
        595                 600                 605

Glu Ile Arg Ile Glu Ser His Leu Gly Asp Gly Asp Asp Lys Val Phe
    610                 615                 620

Leu Ser Ala Gly Ser Ala Asn Ile Tyr Ala Gly Lys Gly His Asp Val
625                 630                 635                 640

Val Tyr Tyr Asp Lys Thr Asp Thr Gly Tyr Leu Thr Ile Asp Gly Thr
                645                 650                 655

Lys Ala Thr Glu Ala Gly Asn Tyr Thr Val Thr Arg Val Leu Gly Gly
            660                 665                 670

Asp Val Lys Val Leu Gln Glu Val Val Lys Glu Gln Glu Val Ser Val
        675                 680                 685

Gly Lys Arg Thr Glu Lys Thr Gln Tyr Arg Ser Tyr Glu Phe Thr His
    690                 695                 700

Ile Asn Gly Lys Asn Leu Thr Glu Thr Asp Asn Leu Tyr Ser Val Glu
705                 710                 715                 720

Glu Leu Ile Gly Thr Thr Arg Ala Asp Lys Phe Phe Gly Ser Lys Phe
                725                 730                 735

Thr Asp Ile Phe His Gly Ala Asp Gly Asp Asp Leu Ile Glu Gly Asn
            740                 745                 750

Asp Gly Asn Asp Arg Leu Tyr Gly Asp Lys Gly Asn Asp Thr Leu Ser
        755                 760                 765

Gly Gly Asn Gly Asp Asp Gln Leu Tyr Gly Gly Asp Gly Asn Asp Lys
    770                 775                 780

Leu Ile Gly Gly Ala Gly Asn Asn Tyr Leu Asn Gly Gly Asp Gly Asp
785                 790                 795                 800

Asp Glu Leu Gln Val Gln Gly Asn Ser Leu Ala Lys Asn Val Leu Phe
                805                 810                 815

Gly Gly Lys Gly Asn Asp Lys Leu Tyr Gly Ser Glu Gly Ala Asp Leu
            820                 825                 830

Leu Asp Gly Gly Glu Gly Asp Asp Leu Leu Lys Gly Gly Tyr Gly Asn
        835                 840                 845

Asp Ile Tyr Arg Tyr Leu Ser Gly Tyr Gly His His Ile Ile Asp Asp
    850                 855                 860

Asp Gly Gly Lys Glu Asp Lys Leu Ser Leu Ala Asp Ile Asp Phe Arg
865                 870                 875                 880

Asp Val Ala Phe Lys Arg Glu Gly Asn Asp Leu Ile Met Tyr Lys Ala
                885                 890                 895

Glu Gly Asn Val Leu Ser Ile Gly His Lys Asn Gly Ile Thr Phe Arg
            900                 905                 910

Asn Trp Phe Glu Lys Glu Ser Gly Asp Ile Ser Asn His Gln Ile Glu
        915                 920                 925

Gln Ile Phe Asp Lys Ser Gly Arg Ile Ile Thr Pro Asp Ser Leu Lys
    930                 935                 940

Lys Ala Leu Glu Tyr Gln Gln Arg Asn Asn Lys Ala Ser Tyr Val Tyr
945                 950                 955                 960
```

-continued

```
Gly Asn Asp Ala Leu Ala Tyr Gly Ser Gln Gly Asp Leu Asn Pro Leu
                965                 970                 975

Ile Asn Glu Ile Ser Lys Ile Ile Ser Ala Ala Gly Ser Phe Asp Val
            980                 985                 990

Lys Glu Glu Arg Thr Ala Ala Ser  Leu Leu Gln Leu Ser  Gly Asn Ala
        995                 1000                 1005

Ser Asp  Phe Ser Tyr Gly Arg  Asn Ser Ile Thr Leu  Thr Thr Ser
    1010                 1015                 1020

Ala


<210> SEQ ID NO 3
<211> LENGTH: 654
<212> TYPE: DNA
<213> ORGANISM: Artificial Sequence
<220> FEATURE:
<223> OTHER INFORMATION: fragment of HlyA

<400> SEQUENCE: 3

ggaaattctc ttgcaaaaaa tgtattattc ggtggaaaag gtaatgacaa gctgtacggc     60

agtgaggggg cagatctgct tgatggtgga gagggggatg atctcctgaa aggcggatat    120

ggtaatgata tttatcgtta tctgtcagga tatggtcatc atattattga tgatgatggg    180

gggaaagagg ataaactcag tttggctgat attgatttcc gggatgtggc cttcaagcga    240

gaaggtaatg acctcatcat gtataaagct gaaggtaatg ttctttccat tggtcataaa    300

aatggtatta cattcaggaa ctggtttgaa aaagagtcag gtgatatctc taatcaccag    360

atagagcaga tttttgataa aagtggccgg ataatcacac ctgattccct taaaaaggca    420

cttgagtatc aacagcgtaa taataaggca agttatgtgt atgggaatga tgcattagcc    480

tatggaagtc agggtgatct taatccatta attaatgaaa tcagcaaaat catttcagct    540

gcaggtagct tcgatgttaa agaggaaaga actgcagctt ctttattgca gttgtccggt    600

aatgccagtg atttttcata tggacggaac tcaataaccc tgaccacatc agca          654


<210> SEQ ID NO 4
<211> LENGTH: 218
<212> TYPE: PRT
<213> ORGANISM: Artificial Sequence
<220> FEATURE:
<223> OTHER INFORMATION: fragment of HlyA

<400> SEQUENCE: 4

Gly Asn Ser Leu Ala Lys Asn Val Leu Phe Gly Gly Lys Gly Asn Asp
1               5                   10                  15

Lys Leu Tyr Gly Ser Glu Gly Ala Asp Leu Leu Asp Gly Gly Glu Gly
            20                  25                  30

Asp Asp Leu Leu Lys Gly Gly Tyr Gly Asn Asp Ile Tyr Arg Tyr Leu
        35                  40                  45

Ser Gly Tyr Gly His His Ile Ile Asp Asp Asp Gly Gly Lys Glu Asp
    50                  55                  60

Lys Leu Ser Leu Ala Asp Ile Asp Phe Arg Asp Val Ala Phe Lys Arg
65                  70                  75                  80

Glu Gly Asn Asp Leu Ile Met Tyr Lys Ala Glu Gly Asn Val Leu Ser
                85                  90                  95

Ile Gly His Lys Asn Gly Ile Thr Phe Arg Asn Trp Phe Glu Lys Glu
            100                 105                 110

Ser Gly Asp Ile Ser Asn His Gln Ile Glu Gln Ile Phe Asp Lys Ser
        115                 120                 125
```

```
Gly Arg Ile Ile Thr Pro Asp Ser Leu Lys Lys Ala Leu Glu Tyr Gln
    130                 135                 140

Gln Arg Asn Asn Lys Ala Ser Tyr Val Tyr Gly Asn Asp Ala Leu Ala
145                 150                 155                 160

Tyr Gly Ser Gln Gly Asp Leu Asn Pro Leu Ile Asn Glu Ile Ser Lys
                165                 170                 175

Ile Ile Ser Ala Ala Gly Ser Phe Asp Val Lys Glu Glu Arg Thr Ala
            180                 185                 190

Ala Ser Leu Leu Gln Leu Ser Gly Asn Ala Ser Asp Phe Ser Tyr Gly
        195                 200                 205

Arg Asn Ser Ile Thr Leu Thr Thr Ser Ala
    210                 215


<210> SEQ ID NO 5
<211> LENGTH: 21
<212> TYPE: DNA
<213> ORGANISM: Artificial Sequence
<220> FEATURE:
<223> OTHER INFORMATION: fusion of E. coli HlyA fragment with synthetic
      peptide

<400> SEQUENCE: 5

ggccgtggtg atagcccggg c                                                21


<210> SEQ ID NO 6
<211> LENGTH: 7
<212> TYPE: PRT
<213> ORGANISM: Artificial Sequence
<220> FEATURE:
<223> OTHER INFORMATION: fusion of E. coli HlyA fragment with synthetic
      peptide

<400> SEQUENCE: 6

Gly Arg Gly Asp Ser Pro Gly
1               5


<210> SEQ ID NO 7
<211> LENGTH: 66
<212> TYPE: DNA
<213> ORGANISM: Artificial Sequence
<220> FEATURE:
<223> OTHER INFORMATION: fusion of E. coli HlyA fragment with synthetic
      peptide

<400> SEQUENCE: 7

ggcagctctg cagcagcagc tgcagcagca gcaagtggtc cgggcggtta tggtccggaa     60

aaccag                                                                 66


<210> SEQ ID NO 8
<211> LENGTH: 22
<212> TYPE: PRT
<213> ORGANISM: Artificial Sequence
<220> FEATURE:
<223> OTHER INFORMATION: fusion of E. coli HlyA fragment with synthetic
      peptide

<400> SEQUENCE: 8

Gly Ser Ser Ala Ala Ala Ala Ala Ala Ala Ala Ser Gly Pro Gly Gly
1               5                   10                  15

Tyr Gly Pro Glu Asn Gln
            20
```

-continued

<210> SEQ ID NO 9
<211> LENGTH: 54
<212> TYPE: DNA
<213> ORGANISM: Artificial Sequence
<220> FEATURE:
<223> OTHER INFORMATION: fusion of E. coli HlyA fragment with synthetic peptide

<400> SEQUENCE: 9
gcagcagcag ctgcagcagc agcaagcggt tatggtccgg aaaaccagta cggc 54

<210> SEQ ID NO 10
<211> LENGTH: 18
<212> TYPE: PRT
<213> ORGANISM: Artificial Sequence
<220> FEATURE:
<223> OTHER INFORMATION: fusion of E. coli HlyA fragment with synthetic peptide

<400> SEQUENCE: 10

Ala Ala Ala Ala Ala Ala Ala Ala Ser Gly Tyr Gly Pro Glu Asn Gln
1 5 10 15

Tyr Gly

<210> SEQ ID NO 11
<211> LENGTH: 729
<212> TYPE: DNA
<213> ORGANISM: Artificial Sequence
<220> FEATURE:
<223> OTHER INFORMATION: fusion of E. coli HlyA mutant with synthetic peptide

<400> SEQUENCE: 11
atgggaaatt ctcttgcaaa aaatgtatta ttcggtggaa aaggtaatga caagctgtac 60
ggcagtgagg gggcagatct gcttgatggt ggagaggggg atgatctcct gaaaggcgga 120
tatggtaatg atatttatcg ttatctgtca ggatatggtc atcatattat tgatgatgat 180
ggggggaaag aggataaact cagtttggct gatattgatt tccgggatgt ggccttcaag 240
cgagaaggta atgacctcat catgtataaa gctgaaggta atgttctttc cattggtcat 300
aaaaatggta ttacattcag gaactggttt gaaaaagagt caggtgatat ctctaatcac 360
cagatagagc agatttttga taaaagtggc cggataatca cacctgattc ccttaaaaag 420
gcacttgagt atcaacagcg taataataag gcaagttatg tgtatgggaa tgatgcatta 480
gcctatggaa gtcagggtga tcttaatcca ttaattaatg aaatcagcaa aatcatttca 540
gctgcaggta gcttcgatgt taaagaggaa agaactgcag cttctttatt gcagttgtcc 600
ggtaatgcca gtgatttttc atatggagac aactcaataa ccctgaccac atcagcaatt 660
gatggccgta tggcagcagc agctgcagca gcagcaagcg gttatggtcc ggaaaaccag 720
tacggctaa 729

<210> SEQ ID NO 12
<211> LENGTH: 242
<212> TYPE: PRT
<213> ORGANISM: Artificial Sequence
<220> FEATURE:
<223> OTHER INFORMATION: fusion of E. coli HlyA mutant with synthetic peptide

<400> SEQUENCE: 12

Met Gly Asn Ser Leu Ala Lys Asn Val Leu Phe Gly Gly Lys Gly Asn
1 5 10 15

-continued

```
Asp Lys Leu Tyr Gly Ser Glu Gly Ala Asp Leu Leu Asp Gly Gly Glu
            20                  25                  30

Gly Asp Asp Leu Leu Lys Gly Gly Tyr Gly Asn Asp Ile Tyr Arg Tyr
        35                  40                  45

Leu Ser Gly Tyr Gly His His Ile Ile Asp Asp Asp Gly Gly Lys Glu
    50                  55                  60

Asp Lys Leu Ser Leu Ala Asp Ile Asp Phe Arg Asp Val Ala Phe Lys
65                  70                  75                  80

Arg Glu Gly Asn Asp Leu Ile Met Tyr Lys Ala Glu Gly Asn Val Leu
                85                  90                  95

Ser Ile Gly His Lys Asn Gly Ile Thr Phe Arg Asn Trp Phe Glu Lys
            100                 105                 110

Glu Ser Gly Asp Ile Ser Asn His Gln Ile Glu Gln Ile Phe Asp Lys
        115                 120                 125

Ser Gly Arg Ile Ile Thr Pro Asp Ser Leu Lys Lys Ala Leu Glu Tyr
    130                 135                 140

Gln Gln Arg Asn Asn Lys Ala Ser Tyr Val Tyr Gly Asn Asp Ala Leu
145                 150                 155                 160

Ala Tyr Gly Ser Gln Gly Asp Leu Asn Pro Leu Ile Asn Glu Ile Ser
                165                 170                 175

Lys Ile Ile Ser Ala Ala Gly Ser Phe Asp Val Lys Glu Glu Arg Thr
            180                 185                 190

Ala Ala Ser Leu Leu Gln Leu Ser Gly Asn Ala Ser Asp Phe Ser Tyr
        195                 200                 205

Gly Asp Asn Ser Ile Thr Leu Thr Thr Ser Ala Ile Asp Gly Arg Met
    210                 215                 220

Ala Ala Ala Ala Ala Ala Ala Ala Ser Gly Tyr Gly Pro Glu Asn Gln
225                 230                 235                 240

Tyr Gly
```

<210> SEQ ID NO 13
<211> LENGTH: 729
<212> TYPE: DNA
<213> ORGANISM: Artificial Sequence
<220> FEATURE:
<223> OTHER INFORMATION: fusion of E. coli HlyA mutant with synthetic peptide

<400> SEQUENCE: 13

```
atgggaaatt ctcttgcaaa aaatgtatta ttcggtggaa aaggtaatga caagctgtac      60

ggcagtgagg gggcagatct gcttgatggt ggagaggggg atgatctcct gaaaggcgga     120

tatggtaatg atatttatcg ttatctgtca ggatatggtc atcatattat tgatgatgat     180

ggggggaaag aggataaact cagtttggct gatattgatt tccgggatgt ggccttcaag     240

cgagaaggta atgacctcat cgcgtataaa gctgaaggta atgttctttc cattggtcat     300

aaaaatggta ttacattcag gaactggttt gaaaaagagt caggtgatat ctctaatcac     360

cagatagagc agatttttga taaaagtggc cggataatca cacctgattc ccttaaaaag     420

gcacttgagt atcaacagcg taataataag gcaagttatg tgtatgggaa tgatgcatta     480

gcctatggaa gtcagggtga tcttaatcca ttaattaatg aaatcagcaa aatcatttca     540

gctgcaggta gcttcgatgt taaagaggaa agaactgcag cttctttatt gcagttgtcc     600

ggtaatgcca gtgatttttc atatggacgg aactcaataa ccctgaccac atcagcaatt     660

gatggccgta tggcagcagc agctgcagca gcagcaagcg gttatggtcc ggaaaaccag     720
```

tacggctaa 729

<210> SEQ ID NO 14
<211> LENGTH: 242
<212> TYPE: PRT
<213> ORGANISM: Artificial Sequence
<220> FEATURE:
<223> OTHER INFORMATION: fusion of E. coli HlyA mutant with synthetic peptide

<400> SEQUENCE: 14

```
Met Gly Asn Ser Leu Ala Lys Asn Val Leu Phe Gly Gly Lys Gly Asn
1               5                   10                  15

Asp Lys Leu Tyr Gly Ser Glu Gly Ala Asp Leu Leu Asp Gly Gly Glu
            20                  25                  30

Gly Asp Asp Leu Leu Lys Gly Gly Tyr Gly Asn Asp Ile Tyr Arg Tyr
        35                  40                  45

Leu Ser Gly Tyr Gly His His Ile Ile Asp Asp Asp Gly Gly Lys Glu
    50                  55                  60

Asp Lys Leu Ser Leu Ala Asp Ile Asp Phe Arg Asp Val Ala Phe Lys
65                  70                  75                  80

Arg Glu Gly Asn Asp Leu Ile Ala Tyr Lys Ala Glu Gly Asn Val Leu
                85                  90                  95

Ser Ile Gly His Lys Asn Gly Ile Thr Phe Arg Asn Trp Phe Glu Lys
            100                 105                 110

Glu Ser Gly Asp Ile Ser Asn His Gln Ile Glu Gln Ile Phe Asp Lys
        115                 120                 125

Ser Gly Arg Ile Ile Thr Pro Asp Ser Leu Lys Lys Ala Leu Glu Tyr
    130                 135                 140

Gln Gln Arg Asn Asn Lys Ala Ser Tyr Val Tyr Gly Asn Asp Ala Leu
145                 150                 155                 160

Ala Tyr Gly Ser Gln Gly Asp Leu Asn Pro Leu Ile Asn Glu Ile Ser
                165                 170                 175

Lys Ile Ile Ser Ala Ala Gly Ser Phe Asp Val Lys Glu Glu Arg Thr
            180                 185                 190

Ala Ala Ser Leu Leu Gln Leu Ser Gly Asn Ala Ser Asp Phe Ser Tyr
        195                 200                 205

Gly Arg Asn Ser Ile Thr Leu Thr Thr Ser Ala Ile Asp Gly Arg Met
    210                 215                 220

Ala Ala Ala Ala Ala Ala Ala Ala Ser Gly Tyr Gly Pro Glu Asn Gln
225                 230                 235                 240

Tyr Gly
```

<210> SEQ ID NO 15
<211> LENGTH: 768
<212> TYPE: DNA
<213> ORGANISM: Artificial Sequence
<220> FEATURE:
<223> OTHER INFORMATION: fusion of FUZEON (enfuvirtide) with E. coli HlyA fragment

<400> SEQUENCE: 15

```
atgtatacca gcctgattca ttctctgatc gaagaaagtc agaaccagca agagaaaaac     60

gaacaagaac tgctggaact ggataaatgg gcgagcctgt ggaactggtt tggaaattct    120

cttgcaaaaa atgtattatt cggtggaaaa ggtaatgaca agctgtacgg cagtgagggg    180

gcagatctgc ttgatggtgg agagggggat gatctcctga aaggcggata tggtaatgat    240
```

-continued

```
atttatcgtt atctgtcagg atatggtcat catattattg atgatgatgg ggggaaagag    300

gataaactca gtttggctga tattgatttc cgggatgtgg ccttcaagcg agaaggtaat    360

gacctcatca tgtataaagc tgaaggtaat gttctttcca ttggtcataa aaatggtatt    420

acattcagga actggtttga aaaagagtca ggtgatatct ctaatcacca gatagagcag    480

atttttgata aaagtggccg gataatcaca cctgattccc ttaaaaaggc acttgagtat    540

caacagcgta ataataaggc aagttatgtg tatgggaatg atgcattagc ctatggaagt    600

cagggtgatc ttaatccatt aattaatgaa atcagcaaaa tcatttcagc tgcaggtagc    660

ttcgatgtta aagaggaaag aactgcagct tctttattgc agttgtccgg taatgccagt    720

gatttttcat atggacggaa ctcaataacc ctgaccacat cagcataa                 768
```

<210> SEQ ID NO 16
<211> LENGTH: 255
<212> TYPE: PRT
<213> ORGANISM: Artificial Sequence
<220> FEATURE:
<223> OTHER INFORMATION: fusion of FUZEON (enfuvirtide) with E. coli
      HlyA fragment

<400> SEQUENCE: 16

```
Met Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp Phe Gly Asn Ser Leu Ala Lys Asn Val Leu Phe Gly
        35                  40                  45

Gly Lys Gly Asn Asp Lys Leu Tyr Gly Ser Glu Gly Ala Asp Leu Leu
    50                  55                  60

Asp Gly Gly Glu Gly Asp Asp Leu Leu Lys Gly Gly Tyr Gly Asn Asp
65                  70                  75                  80

Ile Tyr Arg Tyr Leu Ser Gly Tyr Gly His His Ile Ile Asp Asp Asp
                85                  90                  95

Gly Gly Lys Glu Asp Lys Leu Ser Leu Ala Asp Ile Asp Phe Arg Asp
            100                 105                 110

Val Ala Phe Lys Arg Glu Gly Asn Asp Leu Ile Met Tyr Lys Ala Glu
        115                 120                 125

Gly Asn Val Leu Ser Ile Gly His Lys Asn Gly Ile Thr Phe Arg Asn
    130                 135                 140

Trp Phe Glu Lys Glu Ser Gly Asp Ile Ser Asn His Gln Ile Glu Gln
145                 150                 155                 160

Ile Phe Asp Lys Ser Gly Arg Ile Ile Thr Pro Asp Ser Leu Lys Lys
                165                 170                 175

Ala Leu Glu Tyr Gln Gln Arg Asn Asn Lys Ala Ser Tyr Val Tyr Gly
            180                 185                 190

Asn Asp Ala Leu Ala Tyr Gly Ser Gln Gly Asp Leu Asn Pro Leu Ile
        195                 200                 205

Asn Glu Ile Ser Lys Ile Ile Ser Ala Ala Gly Ser Phe Asp Val Lys
    210                 215                 220

Glu Glu Arg Thr Ala Ala Ser Leu Leu Gln Leu Ser Gly Asn Ala Ser
225                 230                 235                 240

Asp Phe Ser Tyr Gly Arg Asn Ser Ile Thr Leu Thr Thr Ser Ala
                245                 250                 255
```

<210> SEQ ID NO 17

```
<211> LENGTH: 783
<212> TYPE: DNA
<213> ORGANISM: Artificial Sequence
<220> FEATURE:
<223> OTHER INFORMATION: fusion of human HCRF with E. coli HlyA fragment

<400> SEQUENCE: 17

atgagcgaag aaccgccgat ttctctggat ctgacctttc atctgctgcg tgaagtgctg     60

gaaatggcac gtgcagaaca gctggcacag caggcgcaca gcaaccgtaa actgatggaa    120

attatcggaa attctcttgc aaaaaatgta ttattcggtg gaaaaggtaa tgacaagctg    180

tacggcagtg agggggcaga tctgcttgat ggtggagagg gggatgatct cctgaaaggc    240

ggatatggta atgatattta tcgttatctg tcaggatatg gtcatcatat tattgatgat    300

gatgggggga aagaggataa actcagtttg gctgatattg atttccggga tgtggccttc    360

aagcgagaag gtaatgacct catcatgtat aaagctgaag gtaatgttct ttccattggt    420

cataaaaatg gtattacatt caggaactgg tttgaaaaag agtcaggtga tatctctaat    480

caccagatag agcagatttt tgataaaagt ggccggataa tcacacctga ttcccttaaa    540

aaggcacttg agtatcaaca gcgtaataat aaggcaagtt atgtgtatgg gaatgatgca    600

ttagcctatg gaagtcaggg tgatcttaat ccattaatta atgaaatcag caaaatcatt    660

tcagctgcag gtagcttcga tgttaaagag gaaagaactg cagcttcttt attgcagttg    720

tccggtaatg ccagtgattt ttcatatgga cggaactcaa taaccctgac cacatcagca    780

taa                                                                  783


<210> SEQ ID NO 18
<211> LENGTH: 260
<212> TYPE: PRT
<213> ORGANISM: Artificial Sequence
<220> FEATURE:
<223> OTHER INFORMATION: fusion of human HCRF with E. coli HlyA fragment

<400> SEQUENCE: 18

Met Ser Glu Glu Pro Pro Ile Ser Leu Asp Leu Thr Phe His Leu Leu
1               5                   10                  15

Arg Glu Val Leu Glu Met Ala Arg Ala Glu Gln Leu Ala Gln Gln Ala
            20                  25                  30

His Ser Asn Arg Lys Leu Met Glu Ile Ile Gly Asn Ser Leu Ala Lys
        35                  40                  45

Asn Val Leu Phe Gly Gly Lys Gly Asn Asp Lys Leu Tyr Gly Ser Glu
    50                  55                  60

Gly Ala Asp Leu Leu Asp Gly Gly Glu Gly Asp Asp Leu Leu Lys Gly
65                  70                  75                  80

Gly Tyr Gly Asn Asp Ile Tyr Arg Tyr Leu Ser Gly Tyr Gly His His
                85                  90                  95

Ile Ile Asp Asp Asp Gly Gly Lys Glu Asp Lys Leu Ser Leu Ala Asp
            100                 105                 110

Ile Asp Phe Arg Asp Val Ala Phe Lys Arg Glu Gly Asn Asp Leu Ile
        115                 120                 125

Met Tyr Lys Ala Glu Gly Asn Val Leu Ser Ile Gly His Lys Asn Gly
    130                 135                 140

Ile Thr Phe Arg Asn Trp Phe Glu Lys Glu Ser Gly Asp Ile Ser Asn
145                 150                 155                 160

His Gln Ile Glu Gln Ile Phe Asp Lys Ser Gly Arg Ile Ile Thr Pro
                165                 170                 175
```

-continued

```
Asp Ser Leu Lys Lys Ala Leu Glu Tyr Gln Gln Arg Asn Asn Lys Ala
            180                 185                 190

Ser Tyr Val Tyr Gly Asn Asp Ala Leu Ala Tyr Gly Ser Gln Gly Asp
        195                 200                 205

Leu Asn Pro Leu Ile Asn Glu Ile Ser Lys Ile Ile Ser Ala Ala Gly
    210                 215                 220

Ser Phe Asp Val Lys Glu Glu Arg Thr Ala Ala Ser Leu Leu Gln Leu
225                 230                 235                 240

Ser Gly Asn Ala Ser Asp Phe Ser Tyr Gly Arg Asn Ser Ile Thr Leu
                245                 250                 255

Thr Thr Ser Ala
            260


<210> SEQ ID NO 19
<211> LENGTH: 1065
<212> TYPE: DNA
<213> ORGANISM: Artificial Sequence
<220> FEATURE:
<223> OTHER INFORMATION: fusion of human IFABP with E. coli HlyA
      fragment

<400> SEQUENCE: 19

atggcatttg atggcacttg gaaagtagac cggaatgaga actatgaaaa gttcatggag     60

aaaatgggca ttaacgtggt gaagaggaag cttggagctc atgacaactt gaaactgacg    120

atcacacagg aaggaaataa attcacagtc aaagaatcaa gcaacttccg aaacattgat    180

gttgtgtttg aactcggcgt cgactttgcc tatagtctag cagatggaac agaactcact    240

gggacctgga ccatggaggg aaataaactt gttggaaaat tcaaacgtgt agacaatgga    300

aaggagctga ttgctgtccg agagatttct ggtaacgaac taatccaaac ctacacatat    360

gaaggagtgg aggccaagcg gatctttaag aaggaaattg atggccgtgg aaattctctt    420

gcaaaaaatg tattattcgg tggaaaaggt aatgacaagc tgtacggcag tgagggggca    480

gatctgcttg atggtggaga gggggatgat ctcctgaaag gcggatatgg taatgatatt    540

tatcgttatc tgtcaggata tggtcatcat attattgatg atgatggggg gaaagaggat    600

aaactcagtt tggctgatat tgatttccgg gatgtggcct tcaagcgaga aggtaatgac    660

ctcatcatgt ataaagctga aggtaatgtt ctttccattg gtcataaaaa tggtattaca    720

ttcaggaact ggtttgaaaa agagtcaggt gatatctcta atcaccagat agagcagatt    780

tttgataaaa gtggccggat aatcacacct gattccctta aaaaggcact tgagtatcaa    840

cagcgtaata ataaggcaag ttatgtgtat gggaatgatg cattagccta tggaagtcag    900

ggtgatctta atccattaat taatgaaatc agcaaaatca tttcagctgc aggtagcttc    960

gatgttaaag aggaaagaac tgcagcttct ttattgcagt tgtccggtaa tgccagtgat   1020

ttttcatatg gacggaactc aataaccctg accacatcag cataa                   1065


<210> SEQ ID NO 20
<211> LENGTH: 354
<212> TYPE: PRT
<213> ORGANISM: Artificial Sequence
<220> FEATURE:
<223> OTHER INFORMATION: fusion of human IFABP with E. coli HlyA
      fragment

<400> SEQUENCE: 20

Met Ala Phe Asp Gly Thr Trp Lys Val Asp Arg Asn Glu Asn Tyr Glu
1               5                   10                  15
```

-continued

```
Lys Phe Met Glu Lys Met Gly Ile Asn Val Val Lys Arg Lys Leu Gly
            20                  25                  30

Ala His Asp Asn Leu Lys Leu Thr Ile Thr Gln Glu Gly Asn Lys Phe
        35                  40                  45

Thr Val Lys Glu Ser Ser Asn Phe Arg Asn Ile Asp Val Val Phe Glu
    50                  55                  60

Leu Gly Val Asp Phe Ala Tyr Ser Leu Ala Asp Gly Thr Glu Leu Thr
65                  70                  75                  80

Gly Thr Trp Thr Met Glu Gly Asn Lys Leu Val Gly Lys Phe Lys Arg
                85                  90                  95

Val Asp Asn Gly Lys Glu Leu Ile Ala Val Arg Glu Ile Ser Gly Asn
            100                 105                 110

Glu Leu Ile Gln Thr Tyr Thr Tyr Glu Gly Val Glu Ala Lys Arg Ile
        115                 120                 125

Phe Lys Lys Glu Ile Asp Gly Arg Gly Asn Ser Leu Ala Lys Asn Val
    130                 135                 140

Leu Phe Gly Gly Lys Gly Asn Asp Lys Leu Tyr Gly Ser Glu Gly Ala
145                 150                 155                 160

Asp Leu Leu Asp Gly Gly Glu Gly Asp Asp Leu Leu Lys Gly Gly Tyr
                165                 170                 175

Gly Asn Asp Ile Tyr Arg Tyr Leu Ser Gly Tyr Gly His His Ile Ile
            180                 185                 190

Asp Asp Asp Gly Gly Lys Glu Asp Lys Leu Ser Leu Ala Asp Ile Asp
        195                 200                 205

Phe Arg Asp Val Ala Phe Lys Arg Glu Gly Asn Asp Leu Ile Met Tyr
    210                 215                 220

Lys Ala Glu Gly Asn Val Leu Ser Ile Gly His Lys Asn Gly Ile Thr
225                 230                 235                 240

Phe Arg Asn Trp Phe Glu Lys Glu Ser Gly Asp Ile Ser Asn His Gln
                245                 250                 255

Ile Glu Gln Ile Phe Asp Lys Ser Gly Arg Ile Ile Thr Pro Asp Ser
            260                 265                 270

Leu Lys Lys Ala Leu Glu Tyr Gln Gln Arg Asn Asn Lys Ala Ser Tyr
        275                 280                 285

Val Tyr Gly Asn Asp Ala Leu Ala Tyr Gly Ser Gln Gly Asp Leu Asn
    290                 295                 300

Pro Leu Ile Asn Glu Ile Ser Lys Ile Ile Ser Ala Ala Gly Ser Phe
305                 310                 315                 320

Asp Val Lys Glu Glu Arg Thr Ala Ala Ser Leu Leu Gln Leu Ser Gly
                325                 330                 335

Asn Ala Ser Asp Phe Ser Tyr Gly Arg Asn Ser Ile Thr Leu Thr Thr
            340                 345                 350

Ser Ala


<210> SEQ ID NO 21
<211> LENGTH: 780
<212> TYPE: DNA
<213> ORGANISM: Artificial Sequence
<220> FEATURE:
<223> OTHER INFORMATION: fusion of human Mab40 with E. coli HlyA
      fragment

<400> SEQUENCE: 21

atggatgcgg aatttcgcca tgatagcggc tatgaagtgc atcatcagaa actggtgttt      60

tttgcggaag atgtgggcag caacaaaggc gcgattattg gcctgatggt gggcggcgtg     120
```

```
gtgggaaatt ctcttgcaaa aaatgtatta ttcggtggaa aaggtaatga caagctgtac    180

ggcagtgagg gggcagatct gcttgatggt ggagaggggg atgatctcct gaaaggcgga    240

tatggtaatg atatttatcg ttatctgtca ggatatggtc atcatattat tgatgatgat    300

ggggggaaag aggataaact cagtttggct gatattgatt tccgggatgt ggccttcaag    360

cgagaaggta atgacctcat catgtataaa gctgaaggta atgttctttc cattggtcat    420

aaaaatggta ttacattcag gaactggttt gaaaaagagt caggtgatat ctctaatcac    480

cagatagagc agatttttga taaaagtggc cggataatca cacctgattc ccttaaaaag    540

gcacttgagt atcaacagcg taataataag gcaagttatg tgtatgggaa tgatgcatta    600

gcctatggaa gtcagggtga tcttaatcca ttaattaatg aaatcagcaa aatcatttca    660

gctgcaggta gcttcgatgt taaagaggaa agaactgcag cttctttatt gcagttgtcc    720

ggtaatgcca gtgatttttc atatggacgg aactcaataa ccctgaccac atcagcataa    780


<210> SEQ ID NO 22
<211> LENGTH: 259
<212> TYPE: PRT
<213> ORGANISM: Artificial Sequence
<220> FEATURE:
<223> OTHER INFORMATION: fusion of human Mab40 with E. coli HlyA
      fragment

<400> SEQUENCE: 22

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Gly Asn Ser Leu Ala Lys Asn
        35                  40                  45

Val Leu Phe Gly Gly Lys Gly Asn Asp Lys Leu Tyr Gly Ser Glu Gly
    50                  55                  60

Ala Asp Leu Leu Asp Gly Gly Glu Gly Asp Asp Leu Leu Lys Gly Gly
65                  70                  75                  80

Tyr Gly Asn Asp Ile Tyr Arg Tyr Leu Ser Gly Tyr Gly His His Ile
                85                  90                  95

Ile Asp Asp Asp Gly Gly Lys Glu Asp Lys Leu Ser Leu Ala Asp Ile
            100                 105                 110

Asp Phe Arg Asp Val Ala Phe Lys Arg Glu Gly Asn Asp Leu Ile Met
        115                 120                 125

Tyr Lys Ala Glu Gly Asn Val Leu Ser Ile Gly His Lys Asn Gly Ile
    130                 135                 140

Thr Phe Arg Asn Trp Phe Glu Lys Glu Ser Gly Asp Ile Ser Asn His
145                 150                 155                 160

Gln Ile Glu Gln Ile Phe Asp Lys Ser Gly Arg Ile Ile Thr Pro Asp
                165                 170                 175

Ser Leu Lys Lys Ala Leu Glu Tyr Gln Gln Arg Asn Asn Lys Ala Ser
            180                 185                 190

Tyr Val Tyr Gly Asn Asp Ala Leu Ala Tyr Gly Ser Gln Gly Asp Leu
        195                 200                 205

Asn Pro Leu Ile Asn Glu Ile Ser Lys Ile Ile Ser Ala Ala Gly Ser
    210                 215                 220

Phe Asp Val Lys Glu Glu Arg Thr Ala Ala Ser Leu Leu Gln Leu Ser
225                 230                 235                 240
```

```
Gly Asn Ala Ser Asp Phe Ser Tyr Gly Arg Asn Ser Ile Thr Leu Thr
                245                 250                 255

Thr Ser Ala
```

<210> SEQ ID NO 23
<211> LENGTH: 1782
<212> TYPE: DNA
<213> ORGANISM: Artificial
<220> FEATURE:
<223> OTHER INFORMATION: Expression construct

<400> SEQUENCE: 23

```
atgaaaatcg aagaaggtaa actggtaatc tggattaacg gcgataaagg ctataacggt     60

ctcgctgaag tcggtaagaa attcgagaaa gataccggaa ttaaagtcac cgttgagcat    120

ccggataaac tggaagagaa attcccacag gttgcggcaa ctggcgatgg ccctgacatt    180

atcttctggg cacacgaccg ctttggtggc tacgctcaat ctggcctgtt ggctgaaatc    240

accccggaca aagcgttcca ggacaagctg tatccgttta cctgggatgc cgtacgttac    300

aacggcaagc tgattgctta cccgatcgct gttgaagcgt tatcgctgat ttataacaaa    360

gatctgctgc cgaacccgcc aaaaacctgg gaagagatcc cggcgctgga taaagaactg    420

aaagcgaaag gtaagagcgc gctgatgttc aacctgcaag aaccgtactt cacctggccg    480

ctgattgctg ctgacggggg ttatgcgttc aagtatgaaa acggcaagta cgacattaaa    540

gacgtgggcg tggataacgc tggcgcgaaa gcgggtctga ccttcctggt tgacctgatt    600

aaaaacaaac acatgaatgc agacaccgat tactccatcg cagaagctgc ctttaataaa    660

ggcgaaacag cgatgaccat caacggcccg tgggcatggt ccaacatcga caccagcaaa    720

gtgaattatg gtgtaacggt actgccgacc ttcaagggtc aaccatccaa accgttcgtt    780

ggcgtgctga gcgcaggtat taacgccgcc agtccgaaca aagagctggc gaaagagttc    840

ctcgaaaact atctgctgac tgatgaaggt ctggaagcgg ttaataaaga caaaccgctg    900

ggtgccgtag cgctgaagtc ttacgaggaa gagttggcga aagatccacg tattgccgcc    960

accatggaaa acgcccagaa aggtgaaatc atgccgaaca tcccgcagat gtccgctttc   1020

tggtatgccg tgcgtactgc ggtgatcaac gccgccagcg gtcgtcagac tgtcgatgaa   1080

gccctgaaag acgcgcagac tcgtatcacc aagattgatg gccgtggaaa ttctcttgca   1140

aaaaatgtat tattcggtgg aaaaggtaat gacaagctgt acggcagtga gggggcagat   1200

ctgcttgatg gtggagaggg ggatgatctc ctgaaaggcg gatatggtaa tgatatttat   1260

cgttatctgt caggatatgg tcatcatatt attgatgatg atgggggggaa agaggataaa   1320

ctcagtttgg ctgatattga tttccgggat gtggccttca agcgagaagg taatgacctc   1380

atcatgtata aagctgaagg taatgttctt tccattggtc ataaaaatgg tattacattc   1440

aggaactggt ttgaaaaaga gtcaggtgat atctctaatc accagataga gcagattttt   1500

gataaaagtg gccggataat cacacctgat tcccttaaaa aggcacttga gtatcaacag   1560

cgtaataata aggcaagtta tgtgtatggg aatgatgcat tagcctatgg aagtcagggt   1620

gatcttaatc cattaattaa tgaaatcagc aaaatcattt cagctgcagg tagcttcgat   1680

gttaaagagg aaagaactgc agcttcttta ttgcagttgt ccggtaatgc cagtgatttt   1740

tcatatggac ggaactcaat aaccctgacc acatcagcat aa                      1782
```

<210> SEQ ID NO 24
<211> LENGTH: 593
<212> TYPE: PRT

<213> ORGANISM: Artificial
<220> FEATURE:
<223> OTHER INFORMATION: MBP-HlyA1 fusion

<400> SEQUENCE: 24

Met Lys Ile Glu Glu Gly Lys Leu Val Ile Trp Ile Asn Gly Asp Lys
1 5 10 15

Gly Tyr Asn Gly Leu Ala Glu Val Gly Lys Lys Phe Glu Lys Asp Thr
20 25 30

Gly Ile Lys Val Thr Val Glu His Pro Asp Lys Leu Glu Glu Lys Phe
35 40 45

Pro Gln Val Ala Ala Thr Gly Asp Gly Pro Asp Ile Ile Phe Trp Ala
50 55 60

His Asp Arg Phe Gly Gly Tyr Ala Gln Ser Gly Leu Leu Ala Glu Ile
65 70 75 80

Thr Pro Asp Lys Ala Phe Gln Asp Lys Leu Tyr Pro Phe Thr Trp Asp
85 90 95

Ala Val Arg Tyr Asn Gly Lys Leu Ile Ala Tyr Pro Ile Ala Val Glu
100 105 110

Ala Leu Ser Leu Ile Tyr Asn Lys Asp Leu Leu Pro Asn Pro Pro Lys
115 120 125

Thr Trp Glu Glu Ile Pro Ala Leu Asp Lys Glu Leu Lys Ala Lys Gly
130 135 140

Lys Ser Ala Leu Met Phe Asn Leu Gln Glu Pro Tyr Phe Thr Trp Pro
145 150 155 160

Leu Ile Ala Ala Asp Gly Gly Tyr Ala Phe Lys Tyr Glu Asn Gly Lys
165 170 175

Tyr Asp Ile Lys Asp Val Gly Val Asp Asn Ala Gly Ala Lys Ala Gly
180 185 190

Leu Thr Phe Leu Val Asp Leu Ile Lys Asn Lys His Met Asn Ala Asp
195 200 205

Thr Asp Tyr Ser Ile Ala Glu Ala Ala Phe Asn Lys Gly Glu Thr Ala
210 215 220

Met Thr Ile Asn Gly Pro Trp Ala Trp Ser Asn Ile Asp Thr Ser Lys
225 230 235 240

Val Asn Tyr Gly Val Thr Val Leu Pro Thr Phe Lys Gly Gln Pro Ser
245 250 255

Lys Pro Phe Val Gly Val Leu Ser Ala Gly Ile Asn Ala Ala Ser Pro
260 265 270

Asn Lys Glu Leu Ala Lys Glu Phe Leu Glu Asn Tyr Leu Leu Thr Asp
275 280 285

Glu Gly Leu Glu Ala Val Asn Lys Asp Lys Pro Leu Gly Ala Val Ala
290 295 300

Leu Lys Ser Tyr Glu Glu Glu Leu Ala Lys Asp Pro Arg Ile Ala Ala
305 310 315 320

Thr Met Glu Asn Ala Gln Lys Gly Glu Ile Met Pro Asn Ile Pro Gln
325 330 335

Met Ser Ala Phe Trp Tyr Ala Val Arg Thr Ala Val Ile Asn Ala Ala
340 345 350

Ser Gly Arg Gln Thr Val Asp Glu Ala Leu Lys Asp Ala Gln Thr Arg
355 360 365

Ile Thr Lys Ile Asp Gly Arg Gly Asn Ser Leu Ala Lys Asn Val Leu
370 375 380

Phe Gly Gly Lys Gly Asn Asp Lys Leu Tyr Gly Ser Glu Gly Ala Asp

-continued

```
385                 390                 395                 400

Leu Leu Asp Gly Gly Glu Gly Asp Asp Leu Leu Lys Gly Gly Tyr Gly
                405                 410                 415

Asn Asp Ile Tyr Arg Tyr Leu Ser Gly Tyr Gly His His Ile Ile Asp
            420                 425                 430

Asp Asp Gly Gly Lys Glu Asp Lys Leu Ser Leu Ala Asp Ile Asp Phe
        435                 440                 445

Arg Asp Val Ala Phe Lys Arg Glu Gly Asn Asp Leu Ile Met Tyr Lys
    450                 455                 460

Ala Glu Gly Asn Val Leu Ser Ile Gly His Lys Asn Gly Ile Thr Phe
465                 470                 475                 480

Arg Asn Trp Phe Glu Lys Glu Ser Gly Asp Ile Ser Asn His Gln Ile
                485                 490                 495

Glu Gln Ile Phe Asp Lys Ser Gly Arg Ile Ile Thr Pro Asp Ser Leu
            500                 505                 510

Lys Lys Ala Leu Glu Tyr Gln Gln Arg Asn Asn Lys Ala Ser Tyr Val
        515                 520                 525

Tyr Gly Asn Asp Ala Leu Ala Tyr Gly Ser Gln Gly Asp Leu Asn Pro
    530                 535                 540

Leu Ile Asn Glu Ile Ser Lys Ile Ile Ser Ala Ala Gly Ser Phe Asp
545                 550                 555                 560

Val Lys Glu Glu Arg Thr Ala Ala Ser Leu Leu Gln Leu Ser Gly Asn
                565                 570                 575

Ala Ser Asp Phe Ser Tyr Gly Arg Asn Ser Ile Thr Leu Thr Thr Ser
            580                 585                 590

Ala
```

<210> SEQ ID NO 25
<211> LENGTH: 828
<212> TYPE: DNA
<213> ORGANISM: Artificial Sequence
<220> FEATURE:
<223> OTHER INFORMATION: expression construct

<400> SEQUENCE: 25

```
atgagtacaa aagattttaa cttggatttg gtatctgttt cgaagaaaga ttcaggtgca     60

tcaccacgca ttacaagtat ttcgctatgt acacccggtt gtaaaacagg agctctgatg    120

ggttgtaaca tgaaaacagc aacttgtcat tgtagtattc acgtaagcaa aggaaattct    180

cttgcaaaaa atgtattatt cggtggaaaa ggtaatgaca agctgtacgg cagtgagggg    240

gcagatctgc ttgatggtgg agagggggat gatctcctga aaggcggata tggtaatgat    300

atttatcgtt atctgtcagg atatggtcat catattattg atgatgatgg ggggaaagag    360

gataaactca gtttggctga tattgatttc cgggatgtgg ccttcaagcg agaaggtaat    420

gacctcatca tgtataaagc tgaaggtaat gttctttcca ttggtcataa aaatggtatt    480

acattcagga actggtttga aaaagagtca ggtgatatct ctaatcacca gatagagcag    540

atttttgata aaagtggccg gataatcaca cctgattccc ttaaaaaggc acttgagtat    600

caacagcgta ataataaggc aagttatgtg tatgggaatg atgcattagc ctatggaagt    660

cagggtgatc ttaatccatt aattaatgaa atcagcaaaa tcatttcagc tgcaggtagc    720

ttcgatgtta aagaggaaag aactgcagct tctttattgc agttgtccgg taatgccagt    780

gatttttcat atggacggaa ctcaataacc ctgaccacat cagcataa                 828
```

<210> SEQ ID NO 26
<211> LENGTH: 275
<212> TYPE: PRT
<213> ORGANISM: Artificial Sequence
<220> FEATURE:
<223> OTHER INFORMATION: HlyA1-nisin fusion

<400> SEQUENCE: 26

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys Gly Asn Ser Leu Ala Lys Asn
    50                  55                  60

Val Leu Phe Gly Gly Lys Gly Asn Asp Lys Leu Tyr Gly Ser Glu Gly
65                  70                  75                  80

Ala Asp Leu Leu Asp Gly Gly Glu Gly Asp Asp Leu Leu Lys Gly Gly
                85                  90                  95

Tyr Gly Asn Asp Ile Tyr Arg Tyr Leu Ser Gly Tyr Gly His His Ile
            100                 105                 110

Ile Asp Asp Asp Gly Gly Lys Glu Asp Lys Leu Ser Leu Ala Asp Ile
        115                 120                 125

Asp Phe Arg Asp Val Ala Phe Lys Arg Glu Gly Asn Asp Leu Ile Met
    130                 135                 140

Tyr Lys Ala Glu Gly Asn Val Leu Ser Ile Gly His Lys Asn Gly Ile
145                 150                 155                 160

Thr Phe Arg Asn Trp Phe Glu Lys Glu Ser Gly Asp Ile Ser Asn His
                165                 170                 175

Gln Ile Glu Gln Ile Phe Asp Lys Ser Gly Arg Ile Ile Thr Pro Asp
            180                 185                 190

Ser Leu Lys Lys Ala Leu Glu Tyr Gln Gln Arg Asn Asn Lys Ala Ser
        195                 200                 205

Tyr Val Tyr Gly Asn Asp Ala Leu Ala Tyr Gly Ser Gln Gly Asp Leu
    210                 215                 220

Asn Pro Leu Ile Asn Glu Ile Ser Lys Ile Ile Ser Ala Ala Gly Ser
225                 230                 235                 240

Phe Asp Val Lys Glu Glu Arg Thr Ala Ala Ser Leu Leu Gln Leu Ser
                245                 250                 255

Gly Asn Ala Ser Asp Phe Ser Tyr Gly Arg Asn Ser Ile Thr Leu Thr
            260                 265                 270

Thr Ser Ala
        275
```

<210> SEQ ID NO 27
<211> LENGTH: 786
<212> TYPE: DNA
<213> ORGANISM: Artificial Sequence
<220> FEATURE:
<223> OTHER INFORMATION: expression construct

<400> SEQUENCE: 27

```
atgtacggca gtgagggggc agatctgctt gatggtggag agggggatga tctcctgaaa      60

ggcggatatg gtaatgatat ttatcgttat ctgtcaggat atggtcatca tattattgat     120

gatgatgggg ggaaagagga taaactcagt ttggctgata ttgatttccg ggatgtggcc     180
```

```
ttcaagcgag aaggtaatga cctcatcatg tataaagctg aaggtaatgt tctttccatt      240
ggtcataaaa atggtattac attcaggaac tggtttgaaa aagagtcagg tgatatctct      300
aatcaccaga tagagcagat ttttgataaa agtggccgga taatcacacc tgattccctt      360
aaaaaggcac ttgagtatca acagcgtaat aataaggcaa gttatgtgta tgggaatgat      420
gcattagcct atggaagtca gggtgatctt aatccattaa ttaatgaaat cagcaaaatc      480
atttcagctg caggtagctt cgatgttaaa gaggaaagaa ctgcagcttc tttattgcag      540
ttgtccggta atgccagtga tttttcatat ggacggaact caataaccct gaccacatca      600
gcaattgatg gccgtagtac aaaagatttt aacttggatt tggtatctgt ttcgaagaaa      660
gattcaggtg catcaccacg cattacaagt atttcgctat gtacacccgg ttgtaaaaca      720
ggagctctga tgggttgtaa catgaaaaca gcaacttgtc attgtagtat tcacgtaagc      780
aaataa                                                                 786
```

<210> SEQ ID NO 28
<211> LENGTH: 261
<212> TYPE: PRT
<213> ORGANISM: Artificial Sequence
<220> FEATURE:
<223> OTHER INFORMATION: HlyA1-nisin fusion

<400> SEQUENCE: 28

```
Met Tyr Gly Ser Glu Gly Ala Asp Leu Leu Asp Gly Gly Glu Gly Asp
1               5                   10                  15

Asp Leu Leu Lys Gly Gly Tyr Gly Asn Asp Ile Tyr Arg Tyr Leu Ser
            20                  25                  30

Gly Tyr Gly His His Ile Ile Asp Asp Asp Gly Gly Lys Glu Asp Lys
        35                  40                  45

Leu Ser Leu Ala Asp Ile Asp Phe Arg Asp Val Ala Phe Lys Arg Glu
    50                  55                  60

Gly Asn Asp Leu Ile Met Tyr Lys Ala Glu Gly Asn Val Leu Ser Ile
65                  70                  75                  80

Gly His Lys Asn Gly Ile Thr Phe Arg Asn Trp Phe Glu Lys Glu Ser
                85                  90                  95

Gly Asp Ile Ser Asn His Gln Ile Glu Gln Ile Phe Asp Lys Ser Gly
            100                 105                 110

Arg Ile Ile Thr Pro Asp Ser Leu Lys Lys Ala Leu Glu Tyr Gln Gln
        115                 120                 125

Arg Asn Asn Lys Ala Ser Tyr Val Tyr Gly Asn Asp Ala Leu Ala Tyr
    130                 135                 140

Gly Ser Gln Gly Asp Leu Asn Pro Leu Ile Asn Glu Ile Ser Lys Ile
145                 150                 155                 160

Ile Ser Ala Ala Gly Ser Phe Asp Val Lys Glu Glu Arg Thr Ala Ala
                165                 170                 175

Ser Leu Leu Gln Leu Ser Gly Asn Ala Ser Asp Phe Ser Tyr Gly Arg
            180                 185                 190

Asn Ser Ile Thr Leu Thr Thr Ser Ala Ile Asp Gly Arg Ser Thr Lys
        195                 200                 205

Asp Phe Asn Leu Asp Leu Val Ser Val Ser Lys Lys Asp Ser Gly Ala
    210                 215                 220

Ser Pro Arg Ile Thr Ser Ile Ser Leu Cys Thr Pro Gly Cys Lys Thr
225                 230                 235                 240

Gly Ala Leu Met Gly Cys Asn Met Lys Thr Ala Thr Cys His Cys Ser
                245                 250                 255
```

```
Ile His Val Ser Lys
            260


<210> SEQ ID NO 29
<211> LENGTH: 735
<212> TYPE: DNA
<213> ORGANISM: Artificial Sequence
<220> FEATURE:
<223> OTHER INFORMATION: expression construct

<400> SEQUENCE: 29

atgctgaaag gcggatatgg taatgatatt tatcgttatc tgtcaggata tggtcatcat      60

attattgatg atgatggggg gaaagaggat aaactcagtt tggctgatat tgatttccgg     120

gatgtggcct tcaagcgaga aggtaatgac ctcatcatgt ataaagctga aggtaatgtt     180

ctttccattg gtcataaaaa tggtattaca ttcaggaact ggtttgaaaa agagtcaggt     240

gatatctcta atcaccagat agagcagatt tttgataaaa gtggccggat aatcacacct     300

gattccctta aaaaggcact tgagtatcaa cagcgtaata ataaggcaag ttatgtgtat     360

gggaatgatg cattagccta tggaagtcag ggtgatctta atccattaat taatgaaatc     420

agcaaaatca tttcagctgc aggtagcttc gatgttaaag aggaaagaac tgcagcttct     480

ttattgcagt tgtccggtaa tgccagtgat tttcatatgg gacggaactc aataaccctg     540

accacatcag caattgatgg ccgtagtaca aaagatttta acttggattt ggtatctgtt     600

tcgaagaaag attcaggtgc atcaccacgc attacaagta tttcgctatg tacacccggt     660

tgtaaaacag gagctctgat gggttgtaac atgaaaacag caacttgtca ttgtagtatt     720

cacgtaagca aataa                                                      735


<210> SEQ ID NO 30
<211> LENGTH: 244
<212> TYPE: PRT
<213> ORGANISM: Artificial Sequence
<220> FEATURE:
<223> OTHER INFORMATION: HlyA1-nisin fusion

<400> SEQUENCE: 30

Met Leu Lys Gly Gly Tyr Gly Asn Asp Ile Tyr Arg Tyr Leu Ser Gly
1               5                   10                  15

Tyr Gly His His Ile Ile Asp Asp Asp Gly Gly Lys Glu Asp Lys Leu
            20                  25                  30

Ser Leu Ala Asp Ile Asp Phe Arg Asp Val Ala Phe Lys Arg Glu Gly
        35                  40                  45

Asn Asp Leu Ile Met Tyr Lys Ala Glu Gly Asn Val Leu Ser Ile Gly
    50                  55                  60

His Lys Asn Gly Ile Thr Phe Arg Asn Trp Phe Glu Lys Glu Ser Gly
65                  70                  75                  80

Asp Ile Ser Asn His Gln Ile Glu Gln Ile Phe Asp Lys Ser Gly Arg
                85                  90                  95

Ile Ile Thr Pro Asp Ser Leu Lys Lys Ala Leu Glu Tyr Gln Gln Arg
            100                 105                 110

Asn Asn Lys Ala Ser Tyr Val Tyr Gly Asn Asp Ala Leu Ala Tyr Gly
        115                 120                 125

Ser Gln Gly Asp Leu Asn Pro Leu Ile Asn Glu Ile Ser Lys Ile Ile
    130                 135                 140

Ser Ala Ala Gly Ser Phe Asp Val Lys Glu Glu Arg Thr Ala Ala Ser
145                 150                 155                 160
```

Leu Leu Gln Leu Ser Gly Asn Ala Ser Asp Phe Ser Tyr Gly Arg Asn
165 170 175

Ser Ile Thr Leu Thr Thr Ser Ala Ile Asp Gly Arg Ser Thr Lys Asp
180 185 190

Phe Asn Leu Asp Leu Val Ser Val Ser Lys Lys Asp Ser Gly Ala Ser
195 200 205

Pro Arg Ile Thr Ser Ile Ser Leu Cys Thr Pro Gly Cys Lys Thr Gly
210 215 220

Ala Leu Met Gly Cys Asn Met Lys Thr Ala Thr Cys His Cys Ser Ile
225 230 235 240

His Val Ser Lys

<210> SEQ ID NO 31
<211> LENGTH: 693
<212> TYPE: DNA
<213> ORGANISM: Artificial Sequence
<220> FEATURE:
<223> OTHER INFORMATION: expression construct

<400> SEQUENCE: 31
atgggatatg gtcatcatat tattgatgat gatgggggga aagaggataa actcagtttg 60
gctgatattg atttccggga tgtggccttc aagcgagaag gtaatgacct catcatgtat 120
aaagctgaag gtaatgttct ttccattggt cataaaaatg gtattacatt caggaactgg 180
tttgaaaaag agtcaggtga tatctctaat caccagatag agcagatttt tgataaaagt 240
ggccggataa tcacacctga ttcccttaaa aaggcacttg agtatcaaca gcgtaataat 300
aaggcaagtt atgtgtatgg gaatgatgca ttagcctatg gaagtcaggg tgatcttaat 360
ccattaatta atgaaatcag caaaatcatt tcagctgcag gtagcttcga tgttaaagag 420
gaaagaactg cagcttcttt attgcagttg tccggtaatg ccagtgattt ttcatatgga 480
cggaactcaa taaccctgac cacatcagca attgatggcc gtagtacaaa agattttaac 540
ttggatttgg tatctgtttc gaagaaagat tcaggtgcat caccacgcat tacaagtatt 600
tcgctatgta cacccggttg taaaacagga gctctgatgg gttgtaacat gaaaacagca 660
acttgtcatt gtagtattca cgtaagcaaa taa 693

<210> SEQ ID NO 32
<211> LENGTH: 230
<212> TYPE: PRT
<213> ORGANISM: Artificial Sequence
<220> FEATURE:
<223> OTHER INFORMATION: HlyA1-nisin fusion

<400> SEQUENCE: 32

Met Gly Tyr Gly His His Ile Ile Asp Asp Asp Gly Gly Lys Glu Asp
1 5 10 15

Lys Leu Ser Leu Ala Asp Ile Asp Phe Arg Asp Val Ala Phe Lys Arg
20 25 30

Glu Gly Asn Asp Leu Ile Met Tyr Lys Ala Glu Gly Asn Val Leu Ser
35 40 45

Ile Gly His Lys Asn Gly Ile Thr Phe Arg Asn Trp Phe Glu Lys Glu
50 55 60

Ser Gly Asp Ile Ser Asn His Gln Ile Glu Gln Ile Phe Asp Lys Ser
65 70 75 80

Gly Arg Ile Ile Thr Pro Asp Ser Leu Lys Lys Ala Leu Glu Tyr Gln
85 90 95

```
Gln Arg Asn Asn Lys Ala Ser Tyr Val Tyr Gly Asn Asp Ala Leu Ala
            100                 105                 110

Tyr Gly Ser Gln Gly Asp Leu Asn Pro Leu Ile Asn Glu Ile Ser Lys
        115                 120                 125

Ile Ile Ser Ala Ala Gly Ser Phe Asp Val Lys Glu Glu Arg Thr Ala
    130                 135                 140

Ala Ser Leu Leu Gln Leu Ser Gly Asn Ala Ser Asp Phe Ser Tyr Gly
145                 150                 155                 160

Arg Asn Ser Ile Thr Leu Thr Thr Ser Ala Ile Asp Gly Arg Ser Thr
                165                 170                 175

Lys Asp Phe Asn Leu Asp Leu Val Ser Val Ser Lys Lys Asp Ser Gly
            180                 185                 190

Ala Ser Pro Arg Ile Thr Ser Ile Ser Leu Cys Thr Pro Gly Cys Lys
        195                 200                 205

Thr Gly Ala Leu Met Gly Cys Asn Met Lys Thr Ala Thr Cys His Cys
    210                 215                 220

Ser Ile His Val Ser Lys
225                 230


<210> SEQ ID NO 33
<211> LENGTH: 642
<212> TYPE: DNA
<213> ORGANISM: Artificial Sequence
<220> FEATURE:
<223> OTHER INFORMATION: expression construct

<400> SEQUENCE: 33

atgagtttgg ctgatattga tttccgggat gtggccttca agcgagaagg taatgacctc     60

atcatgtata aagctgaagg taatgttctt tccattggtc ataaaaatgg tattacattc    120

aggaactggt ttgaaaaaga gtcaggtgat atctctaatc accagataga gcagattttt    180

gataaaagtg gccggataat cacacctgat tcccttaaaa aggcacttga gtatcaacag    240

cgtaataata aggcaagtta tgtgtatggg aatgatgcat tagcctatgg aagtcagggt    300

gatcttaatc cattaattaa tgaaatcagc aaaatcattt cagctgcagg tagcttcgat    360

gttaaagagg aaagaactgc agcttcttta ttgcagttgt ccggtaatgc cagtgatttt    420

tcatatggac ggaactcaat aaccctgacc acatcagcaa ttgatggccg tagtacaaaa    480

gattttaact tggatttggt atctgtttcg aagaaagatt caggtgcatc accacgcatt    540

acaagtattt cgctatgtac acccggttgt aaaacaggag ctctgatggg ttgtaacatg    600

aaaacagcaa cttgtcattg tagtattcac gtaagcaaat aa                       642


<210> SEQ ID NO 34
<211> LENGTH: 213
<212> TYPE: PRT
<213> ORGANISM: Artificial Sequence
<220> FEATURE:
<223> OTHER INFORMATION: HlyA1-nisin fusion

<400> SEQUENCE: 34

Met Ser Leu Ala Asp Ile Asp Phe Arg Asp Val Ala Phe Lys Arg Glu
1               5                   10                  15

Gly Asn Asp Leu Ile Met Tyr Lys Ala Glu Gly Asn Val Leu Ser Ile
            20                  25                  30

Gly His Lys Asn Gly Ile Thr Phe Arg Asn Trp Phe Glu Lys Glu Ser
        35                  40                  45
```

```
Gly Asp Ile Ser Asn His Gln Ile Glu Gln Ile Phe Asp Lys Ser Gly
    50                  55                  60

Arg Ile Ile Thr Pro Asp Ser Leu Lys Lys Ala Leu Glu Tyr Gln Gln
65                  70                  75                  80

Arg Asn Asn Lys Ala Ser Tyr Val Tyr Gly Asn Asp Ala Leu Ala Tyr
                85                  90                  95

Gly Ser Gln Gly Asp Leu Asn Pro Leu Ile Asn Glu Ile Ser Lys Ile
            100                 105                 110

Ile Ser Ala Ala Gly Ser Phe Asp Val Lys Glu Glu Arg Thr Ala Ala
        115                 120                 125

Ser Leu Leu Gln Leu Ser Gly Asn Ala Ser Asp Phe Ser Tyr Gly Arg
    130                 135                 140

Asn Ser Ile Thr Leu Thr Thr Ser Ala Ile Asp Gly Arg Ser Thr Lys
145                 150                 155                 160

Asp Phe Asn Leu Asp Leu Val Ser Val Ser Lys Lys Asp Ser Gly Ala
                165                 170                 175

Ser Pro Arg Ile Thr Ser Ile Ser Leu Cys Thr Pro Gly Cys Lys Thr
            180                 185                 190

Gly Ala Leu Met Gly Cys Asn Met Lys Thr Ala Thr Cys His Cys Ser
        195                 200                 205

Ile His Val Ser Lys
    210
```

<210> SEQ ID NO 35
<211> LENGTH: 384
<212> TYPE: DNA
<213> ORGANISM: Artificial Sequence
<220> FEATURE:
<223> OTHER INFORMATION: expression construct

<400> SEQUENCE: 35

```
atgggaaatt ctcttgcaaa aaatgtatta ttcggtggaa aaggtaatga caagctgtac      60

ggcagtgagg gggcagatct gcttgatggt ggagaggggg atgatctcct gaaaggcgga     120

tatggtaatg atatttatcg ttatctgtca ggatatggtc atcatattat tgatgatgat     180

ggggggaaag aggataaact cattgatggc cgtagtacaa aagattttaa cttggatttg     240

gtatctgttt cgaagaaaga ttcaggtgca tcaccacgca ttacaagtat ttcgctatgt     300

acacccggtt gtaaaacagg agctctgatg ggttgtaaca tgaaaacagc aacttgtcat     360

tgtagtattc acgtaagcaa ataa                                            384
```

<210> SEQ ID NO 36
<211> LENGTH: 127
<212> TYPE: PRT
<213> ORGANISM: Artificial Sequence
<220> FEATURE:
<223> OTHER INFORMATION: HlyA1-nisin fusion

<400> SEQUENCE: 36

```
Met Gly Asn Ser Leu Ala Lys Asn Val Leu Phe Gly Gly Lys Gly Asn
1               5                   10                  15

Asp Lys Leu Tyr Gly Ser Glu Gly Ala Asp Leu Leu Asp Gly Gly Glu
            20                  25                  30

Gly Asp Asp Leu Leu Lys Gly Gly Tyr Gly Asn Asp Ile Tyr Arg Tyr
        35                  40                  45

Leu Ser Gly Tyr Gly His His Ile Ile Asp Asp Asp Gly Gly Lys Glu
    50                  55                  60
```

```
Asp Lys Leu Ile Asp Gly Arg Ser Thr Lys Asp Phe Asn Leu Asp Leu
65                  70                  75                  80

Val Ser Val Ser Lys Lys Asp Ser Gly Ala Ser Pro Arg Ile Thr Ser
                85                  90                  95

Ile Ser Leu Cys Thr Pro Gly Cys Lys Thr Gly Ala Leu Met Gly Cys
            100                 105                 110

Asn Met Lys Thr Ala Thr Cys His Cys Ser Ile His Val Ser Lys
        115                 120                 125


<210> SEQ ID NO 37
<211> LENGTH: 909
<212> TYPE: DNA
<213> ORGANISM: Artificial Sequence
<220> FEATURE:
<223> OTHER INFORMATION: expression construct

<400> SEQUENCE: 37

atgatcggca gcgacggcaa tgatttgatc aagggcggca aaggcaatga ctatctcgag      60

ggccgcgacg gcgacgatat cttccgcgac gccggcggct ataacctgat cgccggcggc     120

aaaggccaca atatcttcga tacccagcag gcgttgaaga ataccgaggt cgcctacgac     180

ggcaacacgc tttacctgcg cgacgccaag ggcggcatta cgctggcaga cgacatcagc     240

accctgcgca gcaaagaaac ctcctggctt atcttcaaca aagaagtgga tcatcaggta     300

accgccgccg gattgaaatc ggactcaggc ctcaaagcct atgccgccgc caccggcggc     360

gacggcgatg acgtcctgca ggctcgcagc cacgacgcct ggctgttcgg caacgccggc     420

aacgacacgc tgatcggcca cgccggcggc aacctgacct tcgtcggcgg cagcggcgat     480

gacatcctga agggcgtcgg caacggcaac accttcctgt tcagcggcga tttcggccgc     540

gaccagctgt atggcttcaa cgccagcgat aaactggtgt ttatcggcac cgaaggtgcc     600

agcggcaata tccgcgacta cgccacgcag caaaacgacg atctggtgct ggccttcggc     660

cacagccagg tcacgctgat cggcgtctcg ctcgatcaca tcagcaccga tcaggtggtg     720

ttggccattg atggccgtag tacaaaagat tttaacttgg atttggtatc tgtttcgaag     780

aaagattcag gtgcatcacc acgcattaca agtatttcgc tatgtacacc cggttgtaaa     840

acaggagctc tgatgggttg taacatgaaa acagcaactt gtcattgtag tattcacgta     900

agcaaataa                                                             909


<210> SEQ ID NO 38
<211> LENGTH: 302
<212> TYPE: PRT
<213> ORGANISM: Artificial Sequence
<220> FEATURE:
<223> OTHER INFORMATION: LipA-nisin fusion

<400> SEQUENCE: 38

Met Ile Gly Ser Asp Gly Asn Asp Leu Ile Lys Gly Gly Lys Gly Asn
1               5                   10                  15

Asp Tyr Leu Glu Gly Arg Asp Gly Asp Asp Ile Phe Arg Asp Ala Gly
            20                  25                  30

Gly Tyr Asn Leu Ile Ala Gly Gly Lys Gly His Asn Ile Phe Asp Thr
        35                  40                  45

Gln Gln Ala Leu Lys Asn Thr Glu Val Ala Tyr Asp Gly Asn Thr Leu
    50                  55                  60

Tyr Leu Arg Asp Ala Lys Gly Gly Ile Thr Leu Ala Asp Asp Ile Ser
65                  70                  75                  80
```

```
Thr Leu Arg Ser Lys Glu Thr Ser Trp Leu Ile Phe Asn Lys Glu Val
                85                  90                  95

Asp His Gln Val Thr Ala Ala Gly Leu Lys Ser Asp Ser Gly Leu Lys
            100                 105                 110

Ala Tyr Ala Ala Ala Thr Gly Gly Asp Gly Asp Asp Val Leu Gln Ala
        115                 120                 125

Arg Ser His Asp Ala Trp Leu Phe Gly Asn Ala Gly Asn Asp Thr Leu
    130                 135                 140

Ile Gly His Ala Gly Gly Asn Leu Thr Phe Val Gly Gly Ser Gly Asp
145                 150                 155                 160

Asp Ile Leu Lys Gly Val Gly Asn Gly Asn Thr Phe Leu Phe Ser Gly
                165                 170                 175

Asp Phe Gly Arg Asp Gln Leu Tyr Gly Phe Asn Ala Ser Asp Lys Leu
            180                 185                 190

Val Phe Ile Gly Thr Glu Gly Ala Ser Gly Asn Ile Arg Asp Tyr Ala
        195                 200                 205

Thr Gln Gln Asn Asp Asp Leu Val Leu Ala Phe Gly His Ser Gln Val
    210                 215                 220

Thr Leu Ile Gly Val Ser Leu Asp His Ile Ser Thr Asp Gln Val Val
225                 230                 235                 240

Leu Ala Ile Asp Gly Arg Ser Thr Lys Asp Phe Asn Leu Asp Leu Val
                245                 250                 255

Ser Val Ser Lys Lys Asp Ser Gly Ala Ser Pro Arg Ile Thr Ser Ile
            260                 265                 270

Ser Leu Cys Thr Pro Gly Cys Lys Thr Gly Ala Leu Met Gly Cys Asn
        275                 280                 285

Met Lys Thr Ala Thr Cys His Cys Ser Ile His Val Ser Lys
    290                 295                 300
```

<210> SEQ ID NO 39
<211> LENGTH: 522
<212> TYPE: DNA
<213> ORGANISM: Artificial
<220> FEATURE:
<223> OTHER INFORMATION: 3 prime Fragment of HlyC plus gap

<400> SEQUENCE: 39

```
gaatataaac aaaccattag agattcttgg gcatgtatcc tggctatggg ccagttctcc     60

actacacaga aactggccag tatctttgtt tgcaataaat gtattacccg caatacaggc    120

taaccaatat gttttattaa cccgggatga ttaccctgtc gcgtattgta gttgggctaa    180

tttaagttta gaaaatgaaa ttaaatatct taatgatgtt acctcattag ttgcagaaga    240

ctggacttca ggtgatcgta aatggttcat tgactggatt gctcctttcg gggataacgg    300

tgccctgtac aaatatatgc gaaaaaaatt ccctgatgaa ctattcagag ccatcagggt    360

ggatcccaaa actcatgttg gtaaagtatc agaatttcat ggaggtaaaa ttgataaaca    420

gttagcgaat aaaattttta aacaatatca ccacgagtta ataactgaag taaaaagaaa    480

gtcagatttt aatttttcat taactggtta agaggtaatt aa                       522
```

<210> SEQ ID NO 40
<211> LENGTH: 33
<212> TYPE: DNA
<213> ORGANISM: Artificial Sequence
<220> FEATURE:
<223> OTHER INFORMATION: pSUrev_lin_for primer sequence

<400> SEQUENCE: 40
taatatatta atttaaatga tagcaatctt act 33

<210> SEQ ID NO 41
<211> LENGTH: 16
<212> TYPE: DNA
<213> ORGANISM: Artificial Sequence
<220> FEATURE:
<223> OTHER INFORMATION: pSUrev_X_rev primer sequence

<400> SEQUENCE: 41
tgctgatgtg gtcagg 16

<210> SEQ ID NO 42
<211> LENGTH: 28
<212> TYPE: DNA
<213> ORGANISM: Artificial Sequence
<220> FEATURE:
<223> OTHER INFORMATION: pSUrev_lin_Xa_rev primer sequence

<400> SEQUENCE: 42
acggccatca attgctgatg tggtcagg 28

<210> SEQ ID NO 43
<211> LENGTH: 15
<212> TYPE: DNA
<213> ORGANISM: Artificial Sequence
<220> FEATURE:
<223> OTHER INFORMATION: forward nucleotide overhang complementary to
pSUrev_lin_Xa_rev primer

<400> SEQUENCE: 43
gcaattgatg gccgt 15

<210> SEQ ID NO 44
<211> LENGTH: 15
<212> TYPE: DNA
<213> ORGANISM: Artificial Sequence
<220> FEATURE:
<223> OTHER INFORMATION: reverse nucleotide overhang complementary to
pSUrev_lin_for primer

<400> SEQUENCE: 44
taaattaata tatta 15

<210> SEQ ID NO 45
<211> LENGTH: 25
<212> TYPE: PRT
<213> ORGANISM: Artificial Sequence
<220> FEATURE:
<223> OTHER INFORMATION: synthetic peptide

<400> SEQUENCE: 45

```
Asp Tyr Lys Asp Asp Asp Asp Lys Met Ala Ser Met Thr Gly Gly Gln
1               5                   10                  15

Gln Met Gly His His His His His His
            20                  25
```

<210> SEQ ID NO 46
<211> LENGTH: 36
<212> TYPE: PRT
<213> ORGANISM: Artificial Sequence
<220> FEATURE:
<223> OTHER INFORMATION: synthetic peptide

<400> SEQUENCE: 46

-continued

```
Met Gly Ser Ser Ala Ala Ala Ala Ala Ala Ala Ala Ser Gly Pro Gly
1               5                   10                  15

Gly Tyr Gly Pro Glu Asn Gln Gly Pro Ser Gly Pro Gly Gly Tyr Gly
            20                  25                  30

Pro Gly Gly Pro
        35


<210> SEQ ID NO 47
<211> LENGTH: 22
<212> TYPE: PRT
<213> ORGANISM: Artificial Sequence
<220> FEATURE:
<223> OTHER INFORMATION: synthetic peptide

<400> SEQUENCE: 47

Glu Asn Arg Glu Val Pro Pro Gly Phe Thr Ala Leu Ile Lys Thr Leu
1               5                   10                  15

Arg Lys Cys Lys Ile Ile
            20


<210> SEQ ID NO 48
<211> LENGTH: 25
<212> TYPE: PRT
<213> ORGANISM: Artificial Sequence
<220> FEATURE:
<223> OTHER INFORMATION: synthetic peptide

<400> SEQUENCE: 48

Asn Leu Val Ser Gly Leu Ile Glu Ala Arg Lys Tyr Leu Glu Trp Leu
1               5                   10                  15

His Arg Lys Leu Lys Asn Cys Lys Val
            20                  25


<210> SEQ ID NO 49
<211> LENGTH: 26
<212> TYPE: PRT
<213> ORGANISM: Artificial Sequence
<220> FEATURE:
<223> OTHER INFORMATION: synthetic peptide

<400> SEQUENCE: 49

His His His His His His Ile Glu Gly Arg Ala Met Ser Ile Leu Lys
1               5                   10                  15

Ser Pro Ile Asp Glu Arg Ser Ile Leu Lys
            20                  25


<210> SEQ ID NO 50
<211> LENGTH: 37
<212> TYPE: PRT
<213> ORGANISM: Artificial Sequence
<220> FEATURE:
<223> OTHER INFORMATION: synthetic peptide

<400> SEQUENCE: 50

His His His His His His Ile Glu Gly Arg Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Pro Gly
        35


<210> SEQ ID NO 51
<211> LENGTH: 25
```

<212> TYPE: PRT
<213> ORGANISM: Artificial Sequence
<220> FEATURE:
<223> OTHER INFORMATION: synthetic peptide

<400> SEQUENCE: 51

His His His His His His Ile Glu Gly Arg Gly Ala Pro Gly Ala Pro
1 5 10 15

Gly Ser Gln Gly Ala Pro Gly Leu Gln
20 25

<210> SEQ ID NO 52
<211> LENGTH: 48
<212> TYPE: PRT
<213> ORGANISM: Artificial Sequence
<220> FEATURE:
<223> OTHER INFORMATION: synthetic peptide

<400> SEQUENCE: 52

Gly Gly Gly Arg Gly Asp Met Gly Ser Ser Ala Ala Ala Ala Ala Ala
1 5 10 15

Ala Ala Ser Gly Pro Gly Gly Tyr Gly Pro Glu Asn Gln Gly Pro Ser
20 25 30

Gly Pro Gly Gly Tyr Gly Pro Gly Gly Pro Arg Gly Asp Gly Gly Gly
35 40 45

<210> SEQ ID NO 53
<211> LENGTH: 16
<212> TYPE: PRT
<213> ORGANISM: Artificial Sequence
<220> FEATURE:
<223> OTHER INFORMATION: synthetic peptide 238

<400> SEQUENCE: 53

His Met Ile Ser Thr Met Asn Ala Ala Ser Arg Arg Gly Ser Gly Cys
1 5 10 15

<210> SEQ ID NO 54
<211> LENGTH: 16
<212> TYPE: PRT
<213> ORGANISM: Artificial Sequence
<220> FEATURE:
<223> OTHER INFORMATION: synthetic peptide 239

<400> SEQUENCE: 54

Cys Gly Ser Gly His Met Ile Ser Thr Met Asn Ala Ala Ser Arg Arg
1 5 10 15

<210> SEQ ID NO 55
<211> LENGTH: 48
<212> TYPE: PRT
<213> ORGANISM: Artificial Sequence
<220> FEATURE:
<223> OTHER INFORMATION: synthetic peptide 240

<400> SEQUENCE: 55

His Met Ile Ser Thr Met Asn Ala Ala Ser Arg Arg Ser Gly Ser Gly
1 5 10 15

His Met Ile Ser Thr Met Asn Ala Ala Ser Arg Arg Ser Gly Ser Gly
20 25 30

His Met Ile Ser Thr Met Asn Ala Ala Ser Arg Arg Gly Ser Gly Cys
35 40 45

<210> SEQ ID NO 56

-continued

<211> LENGTH: 80
<212> TYPE: PRT
<213> ORGANISM: Artificial Sequence
<220> FEATURE:
<223> OTHER INFORMATION: synthetic peptide 241

<400> SEQUENCE: 56

```
His Met Ile Ser Thr Met Asn Ala Ala Ser Arg Arg Ser Gly Ser Gly
1               5                   10                  15

His Met Ile Ser Thr Met Asn Ala Ala Ser Arg Arg Ser Gly Ser Gly
            20                  25                  30

His Met Ile Ser Thr Met Asn Ala Ala Ser Arg Arg Ser Gly Ser Gly
        35                  40                  45

His Met Ile Ser Thr Met Asn Ala Ala Ser Arg Arg Ser Gly Ser Gly
    50                  55                  60

His Met Ile Ser Thr Met Asn Ala Ala Ser Arg Arg Gly Ser Gly Cys
65                  70                  75                  80
```

<210> SEQ ID NO 57
<211> LENGTH: 68
<212> TYPE: PRT
<213> ORGANISM: Artificial Sequence
<220> FEATURE:
<223> OTHER INFORMATION: synthetic peptide 242

<400> SEQUENCE: 57

```
Met Gly His His His His His His His His His His Ser Ser Gly His
1               5                   10                  15

Ile Glu Gly Arg His Met Ile Ser Thr Met Asn Ala Ala Ser Arg Arg
            20                  25                  30

Ser Gly Ser Gly His Met Ile Ser Thr Met Asn Ala Ala Ser Arg Arg
        35                  40                  45

Ser Gly Ser Gly His Met Ile Ser Thr Met Asn Ala Ala Ser Arg Arg
    50                  55                  60

Gly Ser Gly Cys
65
```

<210> SEQ ID NO 58
<211> LENGTH: 100
<212> TYPE: PRT
<213> ORGANISM: Artificial Sequence
<220> FEATURE:
<223> OTHER INFORMATION: synthetic peptide 243

<400> SEQUENCE: 58

```
Met Gly His His His His His His His His His His Ser Ser Gly His
1               5                   10                  15

Ile Glu Gly Arg His Met Ile Ser Thr Met Asn Ala Ala Ser Arg Arg
            20                  25                  30

Ser Gly Ser Gly His Met Ile Ser Thr Met Asn Ala Ala Ser Arg Arg
        35                  40                  45

Ser Gly Ser Gly His Met Ile Ser Thr Met Asn Ala Ala Ser Arg Arg
    50                  55                  60

Ser Gly Ser Gly His Met Ile Ser Thr Met Asn Ala Ala Ser Arg Arg
65                  70                  75                  80

Ser Gly Ser Gly His Met Ile Ser Thr Met Asn Ala Ala Ser Arg Arg
                85                  90                  95

Gly Ser Gly Cys
            100
```

<210> SEQ ID NO 59
<211> LENGTH: 42
<212> TYPE: PRT
<213> ORGANISM: Homo sapiens

<400> SEQUENCE: 59

Met Ser Glu Glu Pro Pro Ile Ser Leu Asp Leu Thr Phe His Leu Leu
1 5 10 15

Arg Glu Val Leu Glu Met Ala Arg Ala Glu Gln Leu Ala Gln Gln Ala
20 25 30

His Ser Asn Arg Lys Leu Met Glu Ile Ile
35 40

<210> SEQ ID NO 60
<211> LENGTH: 33
<212> TYPE: PRT
<213> ORGANISM: Homo sapiens

<400> SEQUENCE: 60

Met Cys Gly Asn Leu Ser Thr Cys Met Leu Gly Thr Tyr Thr Gln Asp
1 5 10 15

Phe Asn Lys Phe His Thr Phe Pro Gln Thr Ala Ile Gly Val Gly Ala
20 25 30

Pro

<210> SEQ ID NO 61
<211> LENGTH: 37
<212> TYPE: PRT
<213> ORGANISM: Artificial Sequence
<220> FEATURE:
<223> OTHER INFORMATION: Fuzeon

<400> SEQUENCE: 61

Met Tyr Thr Ser Leu Ile His Ser Leu Ile Glu Glu Ser Gln Asn Gln
1 5 10 15

Gln Glu Lys Asn Glu Gln Glu Leu Leu Glu Leu Asp Lys Trp Ala Ser
20 25 30

Leu Trp Asn Trp Phe
35

<210> SEQ ID NO 62
<211> LENGTH: 18
<212> TYPE: PRT
<213> ORGANISM: Artificial Sequence
<220> FEATURE:
<223> OTHER INFORMATION: inhibitor peptide 1

<400> SEQUENCE: 62

Val Leu Arg Arg Cys Gln Glu Ala Asp Arg Glu Glu Leu Asn Tyr Trp
1 5 10 15

Ile Arg

<210> SEQ ID NO 63
<211> LENGTH: 40
<212> TYPE: PRT
<213> ORGANISM: Artificial Sequence
<220> FEATURE:
<223> OTHER INFORMATION: Mab40

<400> SEQUENCE: 63

Asp Ala Glu Phe Arg His Asp Ser Gly Tyr Glu Val His His Gln Lys
1 5 10 15

```
Leu Val Phe Phe Ala Glu Asp Val Gly Ser Asn Lys Gly Ala Ile Ile
            20                  25                  30

Gly Leu Met Val Gly Gly Val Val
        35                  40


<210> SEQ ID NO 64
<211> LENGTH: 42
<212> TYPE: PRT
<213> ORGANISM: Artificial Sequence
<220> FEATURE:
<223> OTHER INFORMATION: Mab42

<400> SEQUENCE: 64

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40


<210> SEQ ID NO 65
<211> LENGTH: 22
<212> TYPE: PRT
<213> ORGANISM: Artificial Sequence
<220> FEATURE:
<223> OTHER INFORMATION: nisin leader sequence

<400> SEQUENCE: 65

Ser Thr Lys Asp Phe Asn Leu Asp Leu Val Ser Val Ser Lys Lys Asp
1               5                   10                  15

Ser Gly Ala Ser Pro Arg
            20


<210> SEQ ID NO 66
<211> LENGTH: 33
<212> TYPE: PRT
<213> ORGANISM: Oncorhynchus mykiss

<400> SEQUENCE: 66

Met Cys Ser Asn Leu Ser Thr Cys Val Leu Gly Lys Leu Ser Gln Glu
1               5                   10                  15

Leu His Lys Leu Gln Thr Tyr Pro Arg Thr Asn Thr Gly Ser Gly Thr
            20                  25                  30

Pro


<210> SEQ ID NO 67
<211> LENGTH: 9
<212> TYPE: PRT
<213> ORGANISM: Artificial Sequence
<220> FEATURE:
<223> OTHER INFORMATION: GG repeat with the consensus sequence
<220> FEATURE:
<221> NAME/KEY: VARIANT
<222> LOCATION: 3,5,7,9
<223> OTHER INFORMATION: Xaa = any amino acid
<220> FEATURE:
<221> NAME/KEY: MOD_RES
<222> LOCATION: 8
<223> OTHER INFORMATION: Xaa = Phe, Ile, Met, Pro, Val, or Trp

<400> SEQUENCE: 67

Gly Gly Xaa Gly Xaa Asp Xaa Xaa Xaa
1               5
```

-continued

```
<210> SEQ ID NO 68
<211> LENGTH: 4
<212> TYPE: PRT
<213> ORGANISM: Artificial Sequence
<220> FEATURE:
<223> OTHER INFORMATION: Ni2 plus ions cleave C-terminal to the this
      tetrapeptide.
<220> FEATURE:
<221> NAME/KEY: VARIANT
<222> LOCATION: 1
<223> OTHER INFORMATION: Xaa = Ser or Thr
<220> FEATURE:
<221> NAME/KEY: VARIANT
<222> LOCATION: 2
<223> OTHER INFORMATION: Xaa = Any amino acid except Proline
<220> FEATURE:
<221> NAME/KEY: VARIANT
<222> LOCATION: 4
<223> OTHER INFORMATION: Xaa = any amino acid

<400> SEQUENCE: 68

Xaa Xaa His Xaa
1
```